United States Patent
Beshore et al.

(10) Patent No.: US 8,653,079 B2
(45) Date of Patent: Feb. 18, 2014

(54) PYRAZOLO [4,3-C] CINNOLIN-3-ONE M1 RECEPTOR POSITIVE ALLOSTERIC MODULATORS

(71) Applicants: Douglas C. Beshore, Lower Gwynedd, PA (US); Scott D. Kuduk, Harleysville, PA (US)

(72) Inventors: Douglas C. Beshore, Lower Gwynedd, PA (US); Scott D. Kuduk, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/710,513

(22) Filed: Dec. 11, 2012

(65) Prior Publication Data
US 2013/0102599 A1 Apr. 25, 2013

Related U.S. Application Data

(66) Division of application No. 13/201,575, filed on Aug. 15, 2011, now Pat. No. 8,486,946, Substitute for application No. 61/208,331, filed on Feb. 23, 2009.

(51) Int. Cl.
*A61K 31/50* (2006.01)
*A61K 31/501* (2006.01)
*C07D 491/00* (2006.01)

(52) U.S. Cl.
USPC .................. 514/252.06; 514/252.05; 544/344; 544/345

(58) Field of Classification Search
USPC .......... 514/252.26, 252.05, 252.06; 544/234, 544/344, 345
See application file for complete search history.

(56) References Cited

U.S. PATENT DOCUMENTS

| 4,591,589 A | 5/1986 | Gasc et al. |
| 4,690,930 A | 9/1987 | Takada et al. |
| 2006/0148819 A1 | 7/2006 | Hennequin et al. |

FOREIGN PATENT DOCUMENTS

WO WO2004073639 9/2004

OTHER PUBLICATIONS

R. M. Eglen et al., "Therapeutic Opportunities from Muscarinic Receptor Research", 2001, pp. 409-414, vol. 22, No. 8, Trends in Pharmacological Sciences.

A. Fisher, Therapeutic Strategies in Alzheimer's Disease: M1 Muscarinic Agonists, 2000, pp. 101-112, vol. 84, Jpn. J. Pharmacol.
T. A. Spalding et al., "Discovery of an Ectopic Activation Site on the M1 Muscarinic Receptor", 2002, pp. 1297-1302, Molecular Pharmacology.
S. Lazareno et al., "Analogs of WIN 62.577 Define a Second Allosteric Site on Muscarinic Receptors", 2002, pp. 1492-1505, vol. 62, Molecular Pharmacology.
S. Lazareno et al., "Allosteric Interactions of Staurosporine and Other Indolocarbazoles with N-[methyl-3-H] Scopolamine and Acetylcholine at Muscarinic Receptor Subtypes: Identification of a Second Allosteric Site",2000, pp. 194-207, vol. 58, Molecular Pharmacology.
M. P. Caulfield, "Muscarinic Receptors-Characterization, Coupling and Function", 1993, pp. 319-379, vol. 58, Pharma. Ther.
N. J. M. Birdsall et al., "Multiple Allosteric Sites on Muscarinic Receptors", 2001, pp. 2517-2524, vol. 68, Life Sciences.
A. Christopoulos et al., "Allosteric Binding Sites on Cell-Surface Receptors: Novel Targets for Drug Discovery", 2002, pp. 198-210, Natural Reviews, Drug Discovery.
H. Brauner-Osborne et al., "Pharmacology of Muscarinic Acetylcholine Receptor Subtypes (m1-m5): High Throughput Assays in Mammalian Cells". 1996, vol. 295, pp. 93-102, E. Journal of Pharmacology.

*Primary Examiner* — Paul V. Ward
(74) *Attorney, Agent, or Firm* — Sylvia A. Ayler; John C. Todaro

(57) ABSTRACT

The present invention is directed to pyrazolo[4,3-c]cinnolin-3-one compounds of formula (I)

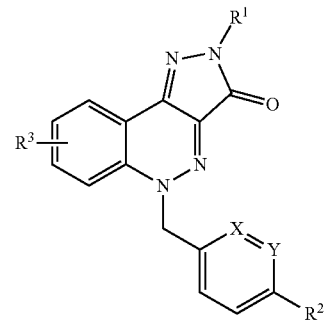

which are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

13 Claims, No Drawings

PYRAZOLO [4,3-C] CINNOLIN-3-ONE M1 RECEPTOR POSITIVE ALLOSTERIC MODULATORS

CROSS REFERENCE TO RELATED APPLICATIONS

This application is a divisional application of U.S. Ser. No. 13/201,575, filed Aug. 15, 2011, which claims the benefit under 35 U.S.C. 119(e) of U.S. Provisional Application No. 61/208,331, filed Feb. 23, 2009.

FIELD OF THE INVENTION

The invention is directed to a class of pyrazolo[4,3-c]cinnolin-3-one compounds, their salts, pharmaceutical compositions comprising them and their use in therapy of the human body. In particular, the invention is directed to a class of pyrazolo[4,3-c]cinnolin-3-one compounds which are muscarinic M1 receptor positive allosteric modulators, and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, *TRENDS in Pharmacological Sciences,* 2001, 22:8, 409-414. In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, *Jpn J Pharmacol,* 2000, 84:101-112.

However, M1 ligands which have been developed and studied for Alzheimer's Disease have produced side effects common to other muscarinic receptor ligands, such as sweating, nausea and diarrhea. See Spalding et al, *Mol Pharmacol,* 2002, 61:6, 1297-1302.

The muscarinic receptors are known to contain one or more allosteric sites, which may alter the affinity with which muscarinic ligands bind to the primary binding or orthosteric sites. See, e.g., S. Lazareno et al, *Mol Pharmacol,* 2002, 62:6, 1491-1505; S. Lazareno et al, *Mol Pharmacol,* 2000, 58, 194-207.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is directed to novel pyrazolo[4,3-c] cinnolin-3-one compounds of generic formula (I)

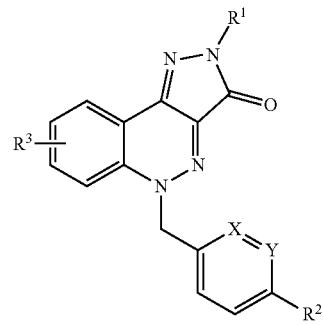

or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to pyrazole [4,3-c]cinnolin-3-one compounds of general formula (I)

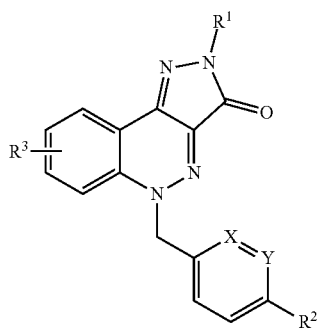

(I)

and pharmaceutically acceptable salts thereof, wherein
—X═Y— is selected from the group consisting of:
(1) —CH═CH—,
(2) —CH═N—, or
(3) —N═CH—
$R^1$ is selected from the group consisting of
(1) aryl,
(2) a heteroaryl group which is a cyclic or polycyclic group, having from five to twelve ring atoms, said ring atoms selected from C, O, N or S, at least one of which is O, N or S,
(3) a heterocyclic group, which is a non-aromatic cyclic or polycyclic group having from three to twelve ring atoms selected from C, O, N or S, at least one of which is O, N or S,
(4) —$C_{1-6}$ alkyl,
(5) —$C_{3-8}$ cycloalkyl,
(6) —$C_{2-6}$ alkenyl
wherein said aryl, heteroaryl, heterocyclic, alkyl, alkenyl and cycloalkyl $R^1$ moiety is optionally substituted with one or more
(a) halogen,
(b) hydroxy,
(c) —O—$C_{1-6}$ alkyl,
(d) —$C_{1-6}$ alkyl, and
(e) cyano;
$R^2$ is selected from the group consisting of
(1) aryl,
(2) a heteroaryl group which is a cyclic or polycyclic group, having from five to twelve ring atoms, said ring atoms selected from C, O, N or S, at least one of which is O, N or S, or
(3) halogen,
wherein said aryl or heteroaryl $R^2$ moiety is optionally substituted with one or more
(a) halogen,
(b) hydroxy,
(c) —O—$C_{1-6}$ alkyl,
(d) —$C_{1-6}$ alkyl,
(e) —CN,
(f) —$NR^A R^B$,
(g) —NH(C═O)—$C_{1-6}$ alkyl,
wherein $R^A$ and $R^B$ are selected from the group consisting of
(i) hydrogen, or
(ii) —$C_{1-6}$ alkyl,
or $R^A$ and $R^B$ are linked together with the nitrogen to which they are both attached to form a 2-6 membered carbocyclic ring, wherein one or two of the ring carbon atoms is replaced by a nitrogen, oxygen or sulfur;

$R^3$ is optionally present at one or more of the fused phenyl ring carbons, and each $R^3$ is selected from the group consisting of
(1) —$C_{1-6}$ alkyl,
(2) halogen,
(3) cyano, and
(4) —O—$C_{1-6}$ alkyl,
wherein any alkyl $R^3$ moiety is optionally substituted with one or more halo.

In particular embodiments of the compounds of formula (I), $R^1$ is aryl (suitably, phenyl), which is optionally substituted by one or more
(a) halogen (for example fluoro, chloro or bromo),
(b) hydroxy,
(c) —O—$C_{1-6}$ alkyl,
(d) —$C_{1-6}$ alkyl (for example, methyl or ethyl), and
(e) cyano.

In particular embodiments of the compounds of formula (I), —X═Y— is —CH═CH—. In other embodiments, X—Y is —CH═N— or —N═CH—.

In particular embodiments of the compounds of formula (I), $R^1$ is heteroaryl (suitably, pyridyl), which is optionally substituted by one or more
(a) halogen (for example fluoro, chloro or bromo),
(b) hydroxy,
(c) —O—$C_{1-6}$ alkyl,
(d) —$C_{1-6}$ alkyl (for example, methyl or ethyl), and
(e) cyano.

In other embodiments of the compounds of formula (I), $R^1$ is heterocyclic (as defined above), which is optionally substituted by one or more
(a) hydroxy, or
(b) —$C_{1-6}$ alkyl (for example, methyl or ethyl).

Suitable $R^1$ heterocyclic groups include morpholine, tetrahydropyran, piperidine, thiane, thiane S-oxide and thiane S-dioxide.

In other embodiments of the compounds of formula (I), $R^1$ is cycloalkyl, alkyl or alkenyl, each of which are optionally substituted by one or more
(a) hydroxy, or
(b) halogen.

In particular embodiments of the compounds of formula (I), $R^2$ is phenyl, which is optionally substituted with one or more
(a) halogen,
(b) hydroxy,
(c) —O—$C_{1-6}$ alkyl,
(d) —$C_{1-6}$ alkyl,
(e) —CN,
(f) —$NR^A R^B$,
(g) —NH(C═O)—$C_{1-6}$ alkyl,
wherein $R^A$ and $R^B$ are selected from the group consisting of
(i) hydrogen, or
(ii) —$C_{1-6}$ alkyl,
or $R^A$ and $R^B$ are linked together with the nitrogen to which they are both attached to form a 2-6 membered carbocyclic ring, wherein one or two of the ring carbon atoms is replaced by a nitrogen, oxygen or sulfur, In other embodiments of the compounds of formula (I), $R^2$ is heteroaryl, which is optionally substituted with one or more
(a) halogen,
(b) hydroxy,
(c) —O—$C_{1-6}$ alkyl,
(d) —$C_{1-6}$ alkyl,
(e) —CN,
(f) —$NR^A R^B$,
(g) —NH(C═O)—$C_{1-6}$ alkyl, wherein $R^A$ and $R^B$ are selected from the group consisting of
(i) hydrogen, or
(ii) —$C_{1-6}$ alkyl,
or $R^A$ and $R^B$ are linked together with the nitrogen to which they are both attached to form a 2-6 membered carbocyclic ring, wherein one or two of the ring carbon atoms is replaced by a nitrogen, oxygen or sulfur.

Suitable $R^2$ heteroaryl groups have 5 or 6 ring atoms.

For example, one subgroup of $R^2$ heteroaryl groups have 5 ring atoms. Exemplary $R^2$ heteroaryl groups in this embodiment are and pyrazole, imidazole and thiazole.

Another subgroup of $R^2$ heteroaryl groups have 6 ring atoms. Exemplary $R^2$ heteroaryl groups in this embodiment are pyridine and pyrimidine.

In other embodiments of the compounds of formula (I), $R^2$ is halogen.

In particular embodiments of the compounds of formula (I), $R^3$ is absent.

In one embodiment, the invention is directed to methods of treating a patient (preferably a human) for diseases in which the M1 receptor is involved, such as Alzheimer's Disease, cognitive impairment, schizophrenia, pain disorders and sleep disorders, by administering to the patient a therapeutically effective amount of a compound of general formula (I).

The invention is also directed to the use of a compound of formula (I) for treating diseases or disorders in which the M1 receptor is involved, such as Alzheimer's disease, cognitive impairment, schizophrenia, pain disorders and sleep disorders.

The invention is also directed to medicaments or pharmaceutical compositions for treating diseases or disorders in which the M1 receptor is involved, such as Alzheimer's disease, cognitive impairment, schizophrenia, pain disorders and sleep disorders, which comprise a compound of formula (I), or a pharmaceutically acceptable salt thereof, and a pharmaceutically acceptable carrier.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, comprising combining a compound of formula (I) with one or more pharmaceutically acceptable carriers.

Within the genus of compounds of formula (I), there is a sub-genus of compounds of formula (II):

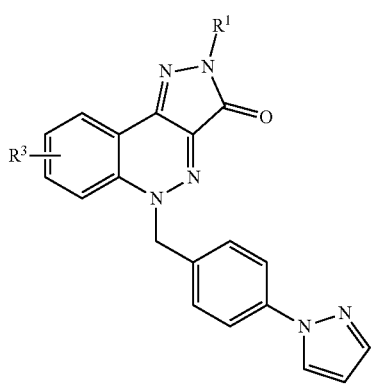

(II)

and pharmaceutically acceptable salts thereof, wherein $R^2$ and $R^3$ are as described above.

In particular embodiments of the compounds of formula (II), $R^1$ is aryl (suitably, phenyl), which is optionally substituted by one or more
(a) halogen (for example fluoro, chloro or bromo),
(b) hydroxy,
(c) —O—$C_{1-6}$ alkyl,
(d) —$C_{1-6}$ alkyl (for example, methyl or ethyl), and
(e) cyano.

In particular embodiments of the compounds of formula (II), $R^1$ is heteroaryl (suitably, pyridyl), which is optionally substituted by one or more
(a) halogen (for example fluoro, chloro or bromo),
(b) hydroxy,
(c) —O—$C_{1-6}$ alkyl,
(d) —$C_{1-6}$ alkyl (for example, methyl or ethyl), and
(e) cyano.

In other embodiments of the compounds of formula (II), $R^1$ is heterocyclic (as defined above, which is optionally substituted by one or more
(a) hydroxy, or
(b) —$C_{1-6}$ alkyl (for example, methyl or ethyl).

Suitable $R^1$ heterocyclic groups include morpholine, tetrahydropyran, piperidine, thiane, thiane S-oxide and thiane S-dioxide.

In other embodiments of the compounds of formula (II), $R^1$ is cycloalkyl, alkyl or alkenyl, each of which are optionally substituted by one or more
(a) hydroxy, or
(b) halogen.

In particular embodiments of the compounds of formula (I), $R^2$ is phenyl, which is optionally substituted with one or more
(a) halogen,
(b) hydroxy,
(c) —O—$C_{1-6}$ alkyl,
(d) —$C_{1-6}$ alkyl,
(e) —CN,
(f) —$NR^A R^B$,
(g) —NH(C=O)—$C_{1-6}$ alkyl,
wherein $R^A$ and $R^B$ are selected from the group consisting of
(i) hydrogen, or
(ii) —$C_{1-6}$ alkyl,
or $R^A$ and $R^B$ are linked together with the nitrogen to which they are both attached to form a 2-6 membered carbocyclic ring, wherein one or two of the ring carbon atoms is replaced by a nitrogen, oxygen or sulfur, In other embodiments of the compounds of formula (I), $R^2$ is heteroaryl, which is optionally substituted with one or more
(a) halogen,
(b) hydroxy,
(c) —O—$C_{1-6}$ alkyl,
(d) —$C_{1-6}$ alkyl,
(e) —CN,
(f) —$NR^A R^B$,
(h) —NH(C=O)—$C_{1-6}$ alkyl,
wherein $R^A$ and $R^B$ are selected from the group consisting of
(i) hydrogen, or
(ii) —$C_{1-6}$ alkyl,
or $R^A$ and $R^B$ are linked together with the nitrogen to which they are both attached to form a 2-6 membered carbocyclic ring, wherein one or two of the ring carbon atoms is replaced by a nitrogen, oxygen or sulfur.

Suitable R² heteroaryl groups have 5 or 6 ring atoms.

For example, one subgroup of R² heteroaryl groups have 5 ring atoms. Exemplary R² heteroaryl groups in this embodiment are and pyrazole, imidazole and thiazole.

Another subgroup of R² heteroaryl groups have 6 ring atoms. Exemplary R² heteroaryl groups in this embodiment are pyridine and pyrimidine.

In other embodiments of the compounds of formula (I), R² is halogen.

In particular embodiments of the compounds of formula (II), R³ is absent.

In other embodiments of the compounds of formula (II), R³ is halogen (suitably fluoro, chloro or bromo) and is present at one of the fused phenyl carbon atoms.

In other embodiments, R³ is halogen (suitably fluoro, chloro or bromo) and is present at the position shown in (IIA) below:

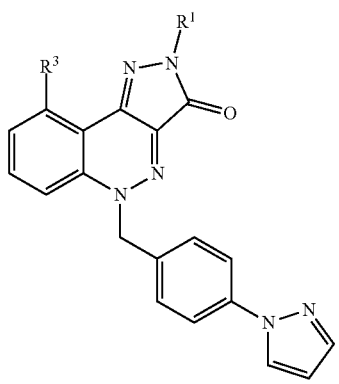

(IIA)

In another sub-genus within the genus of compounds of formula (I), there are compounds of formula (III):

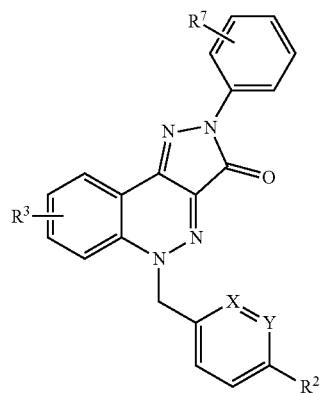

(III)

and pharmaceutically acceptable salts thereof, wherein R⁷ is optionally present at one or more of the phenyl ring carbon atoms, and each R⁷ is selected from the group consisting of
(1) halogen,
(2) hydroxy,
(3) —O—$C_{1-6}$ alkyl,
(4) —$C_{1-6}$ alkyl, and
(5) cyano.

In particular embodiments of the compounds of formula (III), —X═Y— is —CH═CH—. In other embodiments, —X═Y— is —CH═N— or —N═CH—.

In particular embodiments of the compounds of formula (III), R³ is absent.

In particular embodiments of the compounds of formula (III), R² is phenyl, which is optionally substituted with one or more
(a) halogen,
(b) hydroxy,
(c) —O—$C_{1-6}$ alkyl,
(d) —$C_{1-6}$ alkyl,
(e) —CN,
(f) —NR$^A$R$^B$,
(g) —N(C═O)—NR$^A$R$^B$,
wherein R$^A$ and R$^B$ are selected from the group consisting of
(i) hydrogen, or
(ii) —$C_{1-6}$ alkyl,
or R$^A$ and R$^B$ are linked together with the nitrogen to which they are both attached to form a 2-6 membered carbocyclic ring, wherein one or two of the ring carbon atoms is replaced by a nitrogen, oxygen or sulfur, In other embodiments of the compounds of formula (III), R² is heteroaryl, which is optionally substituted with one or more
(a) halogen,
(b) hydroxy,
(c) —O—$C_{1-6}$ alkyl,
(d) —$C_{1-6}$ alkyl,
(e) —CN,
(f) —NR$^A$R$^B$,
(g) —NH(C═O)—$C_{1-6}$ alkyl,
wherein R$^A$ and R$^B$ are selected from the group consisting of
(i) hydrogen, or
(ii) —$C_{1-6}$ alkyl,
or R$^A$ and R$^B$ are linked together with the nitrogen to which they are both attached to form a 2-6 membered carbocyclic ring, wherein one or two of the ring carbon atoms is replaced by a nitrogen, oxygen or sulfur.

Suitable R² heteroaryl groups have 5 or 6 ring atoms.

For example, one subgroup of R² heteroaryl groups have 5 ring atoms. Exemplary R² heteroaryl groups in this embodiment are and pyrazole, imidazole and thiazole.

Another subgroup of R² heteroaryl groups have 6 ring atoms. Exemplary R² heteroaryl groups in this embodiment are pyridine and pyrimidine.

In other embodiments of the compounds of formula (III), R² is halogen.

In other embodiments of the compounds of formula (III), R³ is halogen (suitably fluoro, chloro or bromo) and is present at one of the fused phenyl carbon atoms.

In particular embodiments, the compounds of formula (III) are compounds of formula (IIIA)

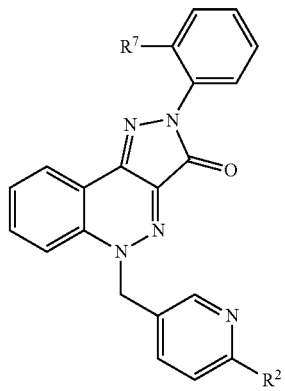

(IIIA)

or pharmaceutically acceptable salts thereof.

In other embodiments, the compounds of formula (III) are compounds of formula (IIIB)

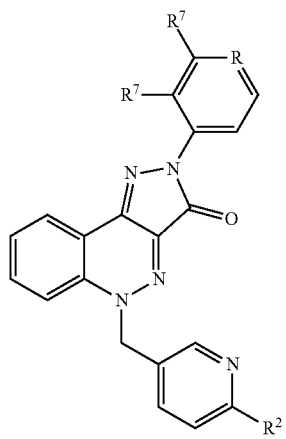

(IIIB)

or pharmaceutically acceptable salts thereof.

In another sub-genus within the genus of compounds of formula (I), there are compounds of formula (IV):

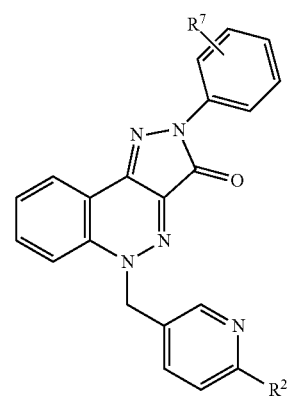

(IV)

and pharmaceutically acceptable salts thereof, wherein $R^7$ is optionally present at one or more of the phenyl ring carbon atoms, and each $R^7$ is selected from the group consisting of
  (1) halogen,
  (2) hydroxy,
  (3) —O—$C_{1-6}$ alkyl,
  (4) —$C_{1-6}$ alkyl, and
  (5) cyano.

In particular embodiments of the compounds of formula (IV), $R^2$ is phenyl, which is optionally substituted with one or more
  (a) halogen,
  (b) hydroxy,
  (c) —O—$C_{1-6}$ alkyl,
  (d) —$C_{1-6}$ alkyl,
  (e) —CN,
  (f) —$NR^A R^B$,
  (g) —NH(C=O)—$C_{1-6}$ alkyl,
  wherein $R^A$ and $R^B$ are selected from the group consisting of
    (i) hydrogen, or
    (ii) —$C_{1-6}$ alkyl,
    or $R^A$ and $R^B$ are linked together with the nitrogen to which they are both attached to form a 2-6 membered carbocyclic ring, wherein one or two of the ring carbon atoms is replaced by a nitrogen, oxygen or sulfur, In other embodiments of the compounds of formula (IV), $R^2$ is heteroaryl, which is optionally substituted with one or more
  (a) halogen,
  (b) hydroxy,
  (c) —O—$C_{1-6}$ alkyl,
  (d) —$C_{1-6}$ alkyl,
  (e) —CN,
  (f) —$NR^A R^B$,
  (g) —NH(C=O)—$C_{1-6}$ alkyl,
  wherein $R^A$ and $R^B$ are selected from the group consisting of
    (i) hydrogen, or
    (ii) —$C_{1-6}$ alkyl,
    or $R^A$ and $R^B$ are linked together with the nitrogen to which they are both attached to form a 2-6 membered carbocyclic ring, wherein one or two of the ring carbon atoms is replaced by a nitrogen, oxygen or sulfur.

Suitable $R^2$ heteroaryl groups have 5 or 6 ring atoms.

For example, one subgroup of $R^2$ heteroaryl groups have 5 ring atoms. Exemplary $R^2$ heteroaryl groups in this embodiment are and pyrazole, imidazole and thiazole.

Another subgroup of $R^2$ heteroaryl groups have 6 ring atoms. Exemplary $R^2$ heteroaryl groups in this embodiment are pyridine and pyrimidine.

In other embodiments of the compounds of formula (IV), $R^2$ is halogen.

In another sub-genus within the genus of compounds of formula (I), there are compounds of formula (V)

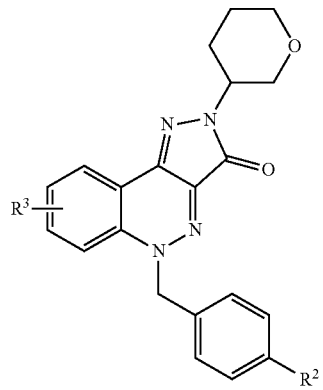

(V)

and pharmaceutically acceptable salts thereof.

Specific embodiments of formula (I) are described herein as Examples 1-96, such as 2-(2-Fluorophenyl)-5-{[4-(1H-pyrazol-1-yl)phenyl]methyl}-2,5-dihydro-3H-pyrazolo[4,3-c]cinnolin-3-one;

2-(2,3-Dihydroxypropyl)-5-[4-(1H-pyrazol-1-yl)benzyl]-2,5-dihydro-3H-pyrazolo[4,3-c]cinnolin-3-one;

2-(2-Bromo-6-fluorophenyl)-5-{[4-(1H-pyrazol-1-yl)phenyl]methyl}-2,5-dihydro-3H-pyrazolo[4,3-c]cinnolin-3-one;

3-Fluoro-2-(3-oxo-5-{[4-(1H-pyrazol-1-yl)phenyl]methyl}-3,5-dihydro-2H-pyrazolo[4,3-c]cinnolin-2-yl)benzonitrile;

9-Fluoro-2-(2-fluorophenyl)-5-{[4-(1H-pyrazol-1-yl)phenyl]methyl}-2,5-dihydro-3H-pyrazolo[4,3-c]cinnolin-3-one;

9-Fluoro-2-(2-fluorophenyl)-5-{[4-(1H-imidazol-1-yl)phenyl]methyl}-2,5-dihydro-3H-pyrazolo[4,3-c]cinnolin-3-one;

2-(2-Fluorophenyl)-5-[(4-iodophenyl)methyl]-2,5-dihydro-3H-pyrazolo[4,3-c]cinnolin-3-one;

2-(2-Fluorophenyl)-5-{[4-(1,3-thiazol-4-yl)phenyl]methyl}-2,5-dihydro-3H-pyrazolo[4,3-c]cinnolin-3-one;

5-[(5-Bromopyridin-2-yl)methyl]-2-(2-methylphenyl)-2,5-dihydro-3H-pyrazolo[4,3-c]cinnolin-3-one;

5-[(6-Bromopyridin-3-yl)methyl]-2-(2-methylphenyl)-2,5-dihydro-3H-pyrazolo[4,3-c]cinnolin-3-one;

5-{[6-(1H-Imidazol-1-yl)pyridine-3-yl]methyl}-2-(2-methylphenyl)-2,5-dihydro-3H-pyrazolo[4,3-c]cinnolin-3-one;

2-(2-Methylphenyl)-5-{[6-(1H-pyrazol-1-yl)pyridine-3-yl]methyl}-2,5-dihydro-3H-pyrazolo[4,3-c]cinnolin-3-one;

2-(2-Methylphenyl)-5-{[6-(1-methyl-1H-pyrazol-4-yl)pyridine-3-yl]methyl}-2,5-dihydro-3H-pyrazolo[4,3-c]cinnolin-3-one;

2-(2-Fluoro-3-methylpyridin-4-yl)-5-{[4-(1H-pyrazol-1-yl)phenyl]methyl}-2,5-dihydro-3H-pyrazolo[4,3-c]cinnolin-3-one;

(±)-5-[4-(1H-pyrazol-1-yl)benzyl]-2-(tetrahydro-2H-pyran-3-yl)-2,5-dihydro-3H-pyrazolo[4,3-c]cinnolin-3-one;

(+)-5-[4-(1H-pyrazol-1-yl)benzyl]-2-(tetrahydro-2H-pyran-3-yl)-2,5-dihydro-3H-pyrazolo[4,3-c]cinnolin-3-one;

(−)-5-[4-(1H-pyrazol-1-yl)benzyl]-2-(tetrahydro-2H-pyran-3-yl)-2,5-dihydro-3H-pyrazolo[4,3-c]cinnolin-3-one;

2-(2,3-Dimethylphenyl)-5-[4-(1H-pyrazol-1-yl)benzyl]-2,5-dihydro-3H-pyrazolo[4,3-c]cinnolin-3-one;

(±)-5-(4-Iodobenzyl)-2-(tetrahydro-2H-pyran-3-yl)-2,5-dihydro-3H-pyrazolo[4,3-c]cinnolin-3-one;

(±)-5-[4-(2-Methylpyridin-4-yl)benzyl]-2-(tetrahydro-2H-pyran-3-yl)-2,5-dihydro-3H-pyrazolo[4,3-c]cinnolin-3-one;

(±)-2-(Tetrahydro-2H-pyran-3-yl)-5-{[4-(1H-1,2,3-triazol-1-yl)phenyl]methyl}-2,5-dihydro-3H-pyrazolo[4,3-c]cinnolin-3-one;

(±)-2-(Tetrahydro-2H-pyran-3-yl)-5-{[4-(1H-1,2,3-triazol-2-yl)phenyl]methyl}-2,5-dihydro-3H-pyrazolo[4,3-c]cinnolin-3-one;

(±)-2-(Oxiran-2-ylmethyl)-5-[4-(1H-pyrazol-1-yl)benzyl]-2,5-dihydro-3H-pyrazolo[4,3-c]cinnolin-3-one;

(±)-2-(2,3-dimethoxypropyl)-5-[4-(1H-pyrazol-1-yl)benzyl]-2,5-dihydro-3H-pyrazolo[4,3-c]cinnolin-3-one;

6-Chloro-2-(2-methylphenyl)-5-[4-(1H-pyrazol-1-yl)benzyl]-2,5-dihydro-3H-pyrazolo[4,3-c]cinnolin-3-one;

6-Chloro-2-(trans-3-hydroxytetrahydro-2H-pyran-4-yl)-5-[4-(1H-pyrazol-1-yl)benzyl]-2,5-dihydro-3H-pyrazolo[4,3-c]cinnolin-3-one;

6-Chloro-2-(trans-3-hydroxytetrahydro-2H-pyran-4-yl)-5-[4-(1H-pyrazol-1-yl)benzyl]-2,5-dihydro-3H-pyrazolo[4,3-c]cinnolin-3-one;

6-Chloro-2-(cis-3-hydroxytetrahydro-2H-pyran-4-yl)-5-[4-(1H-pyrazol-1-yl)benzyl]-2,5-dihydro-3H-pyrazolo[4,3-c]cinnolin-3-one;

6-Chloro-2-(cis-3-hydroxytetrahydro-2H-pyran-4-yl)-5-[4-(1H-pyrazol-1-yl)benzyl]-2,5-dihydro-3H-pyrazolo[4,3-c]cinnolin-3-one;

(±)-6-Chloro-5-(4-iodobenzyl)-2-tetrahydro-2H-pyran-3-yl)-2,5-dihydro-3H-pyrazolo[4,3-c]cinnolin-3-one;

(±)-6-Chloro-5-{[4-(6-methylpyridin-3-yl)phenyl]methyl}-2-(tetrahydro-2H-pyran-3-yl)-2,5-dihydro-3H-pyrazolo[4,3-c]cinnolin-3-one;

(±)-6-Chloro-2-(trans-2-hydroxycyclohexyl)-5-{[4-(6-methylpyridin-3-yl)phenyl]methyl}-2-(tetrahydro-2H-pyran-3-yl)-2,5-dihydro-3H-pyrazolo[4,3-c]cinnolin-3-one;

(±)-6-Chloro-2-(trans-2-hydroxycyclohexyl)-5[(6'-methyl-2,3'-bipyridin-5-yl)methyl]-2,5-dihydro-3H-pyrazolo[4,3-c]cinnolin-3-one;

(±)-6-Chloro-2-(trans-2-hydroxycyclohexyl)-5[(6-methylpyridin-3-yl)methyl]-2,5-dihydro-3H-pyrazolo[4,3-c]cinnolin-3-one;

(±)-2-[cis, trans-4-methyltetrahydro-2H-pyran-3-yl]-5-[4-(1H-pyrazol-1-yl)benzyl]-2,5-dihydro-3H-pyrazolo[4,3-c]cinnolin-3-one;

trans-2-[4-Methyltetrahydro-2H-pyran-3-yl]-5-[4-(1H-pyrazol-1-yl)benzyl]-2,5-dihydro-3H-pyrazolo[4,3-c]cinnoline-3-one;

cis-2-[4-Methyltetrahydro-2H-pyran-3-yl]-5-[4-(1H-pyrazol-1-yl)benzyl]-2,5-dihydro-3H-pyrazolo[4,3-c]cinnoline-3-one;

trans-2-[4-Methyltetrahydro-2H-pyran-3-yl]-5-[4-(1H-pyrazol-1-yl)benzyl]-2,5-dihydro-3H-pyrazolo[4,3-c]cinnoline-3-one;

cis-2-[4-Methyltetrahydro-2H-pyran-3-yl]-5-[4-(1H-pyrazol-1-yl)benzyl]-2,5-dihydro-3H-pyrazolo[4,3-c]cinnoline-3-one;

(±)-cis,trans-2-methyltetrahydro-2H-pyran-3-yl]-5-[4-(1H-pyrazol-1-yl)benzyl]-2,5-dihydro-3H-pyrazolo[4,3-c]cinnolin-3-one;

trans-2-methyltetrahydro-2H-pyran-3-yl]-5-[4-(1H-pyrazol-1-yl)benzyl]-2,5-dihydro-3H-pyrazolo[4,3-c]cinnolin-3-one;

cis-2-Methyltetrahydro-2H-pyran-3-yl]-5-[4-(1H-pyrazol-1-yl)benzyl]-2,5-dihydro-3H-pyrazolo[4,3-c]cinnolin-3-one;

trans-2-Methyltetrahydro-2H-pyran-3-yl]-5-[4-(1H-pyrazol-1-yl)benzyl]-2,5-dihydro-3H-pyrazolo[4,3-c]cinnolin-3-one;

cis-2-Methyltetrahydro-2H-pyran-3-yl]-5-[4-(1H-pyrazol-1-yl)benzyl]-2,5-dihydro-3H-pyrazolo[4,3-c]cinnolin-3-one;

2-(2-Methylphenyl)-5-{[6-(morpholin-4-yl)pyridine-3-yl]methyl}-2,5-dihydro-3H-pyrazolo[4,3-c]cinnolin-3-one;

2-(2-Methylphenyl)-5-{[6-(1,3-thiazol-4-yl)pyridin-3-yl]methyl}-2,5-dihydro-3H-pyrazolo[4,3-c]cinnolin-3-one;

2-(2,3-Dimethylphenyl)-5-{[6-(1,3-thiazol-4-yl)pyridin-3-yl]methyl}-2,5-dihydro-3H-pyrazolo[4,3-c]cinnolin-3-one;

2-(6-Fluoro-2-methylpyridin-3-yl)-5-{[6-(1-methyl-1H-pyrazol-4-yl)pyridin-3-yl]methyl}-2,5-dihydro-3H-pyrazolo[4,3-c]cinnolin-3-one;

(±)-2-(trans-2-Hydroxycyclohexyl)-5-{[6-(1,3-thiazol-4-yl)pyridin-3-yl]methyl}-2,5-dihydro-3H-pyrazolo[4,3-c]cinnolin-3-one;

2-(2-Methylphenyl)-5-[4-(6-methylpyridin-3-yl)benzyl]-2,5-dihydro-3H-pyrazolo[4,3-c]cinnolin-3-one;

2-(2,3-Dimethylphenyl)-5-[(6'-methyl-2,3'-bipyridin-5-yl)methyl]-2,5-dihydro-3H-pyrazolo[4,3-c]cinnolin-3-one;

2-(2,3-Dimethylphenyl)-5-[(6'-methyl-2,3'-bipyridin-5-yl)methyl]-2,5-dihydro-3H-pyrazolo[4,3-c]cinnolin-3-one;

and pharmaceutically acceptable salts thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formulae (II) to (V), or a pharmaceutically acceptable salt thereof.

The invention is also directed to the use of a compound of formulae (II) to (V), for treating a disease or disorder in which the M1 receptor is involved, such as Alzheimer's Disease, cognitive impairment, schizophrenia, pain disorders and sleep disorders, by administering to the patient a compound of formulae (II) to (V), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formulae (II) to (V), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising combining a compound of formulae (II) to (V), or a pharmaceutically acceptable salt thereof, with a pharmaceutically acceptable carrier.

Where a variable occurs more than once in any of formulae (II) to (V), or in a substituent thereof, the individual occurrences of that variable are independent of each other, unless otherwise specified.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Preferred alkenyl groups for use in the invention are $C_{2-6}$ alkenyl groups, having from two to six carbon atoms. Exemplary alkenyl groups include ethenyl and propenyl.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

As used herein, the term "heteroaryl," by itself or as part of another substituent, means a cyclic or polycyclic group having from five to twelve ring atoms selected from C, N, O and S, wherein at least one ring heteroatom is O, N or S, and wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyridyl, thiazolyl and imidazolyl.

Another subgroup of heteroaryl groups have 6 ring atoms. Exemplary heteroaryl groups in this embodiment are pyridinyl and pyrimidinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "heterocyclic," by itself or as part of another substituent, means a non-aromatic cyclic or polycyclic group having from three to twelve ring atoms selected from C, N, O or S, at least one of which is N, O or S. Suitable non-aromatic heterocyclic groups for use in the invention include piperidinyl, piperazinyl, morpholinyl, thiomorpholinyl, tetrahydropyranyl, tetrahydrofuranyl and tetrahydropyrazopyrimidine. Heterocyclic groups for use in the invention have three to twelve ring atoms. Preferred heterocyclic groups have from five to eight ring atoms. More preferred heterocyclic groups have from five to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Preferably, the substituent is bonded to a ring carbon atom. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formulae (I) to (V).

Formulae (I) to (V) are shown above without a definite stereochemistry. The present invention includes all stereoisomers of formulae (I), (II), (III), (IV) and (V) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

Specific embodiments of the compounds of the invention, and methods of making them, are described in the Examples herein.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379; *Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae (I), (II), (III), (IV) and (IVA) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and posttraumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another specific embodiment, the present invention provides a method for treating schizophrenia or psychosis comprising administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists, such as ABT089, SSR180711 and MEM63908; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SGS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine H3 receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; $GABA_A$ inverse agonists; GSK3β inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists and dopamine receptor agonists such as alentemol, bromocriptine, fenoldopam, lisuride, naxagolide, pergolide and pramipexole.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the schemes and examples herein. Starting materials are made according to procedures known in the art or as illustrated herein. The following examples are provided so that the invention might be more fully understood.

The following examples are provided to illustrate the invention and are not to be construed as limiting the scope of the invention in any manner.

Generic Scheme 1:

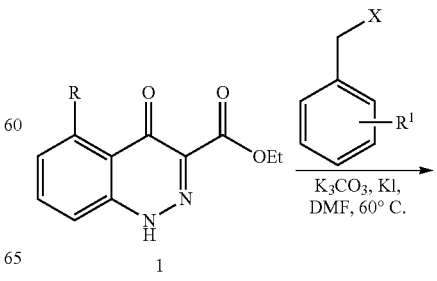

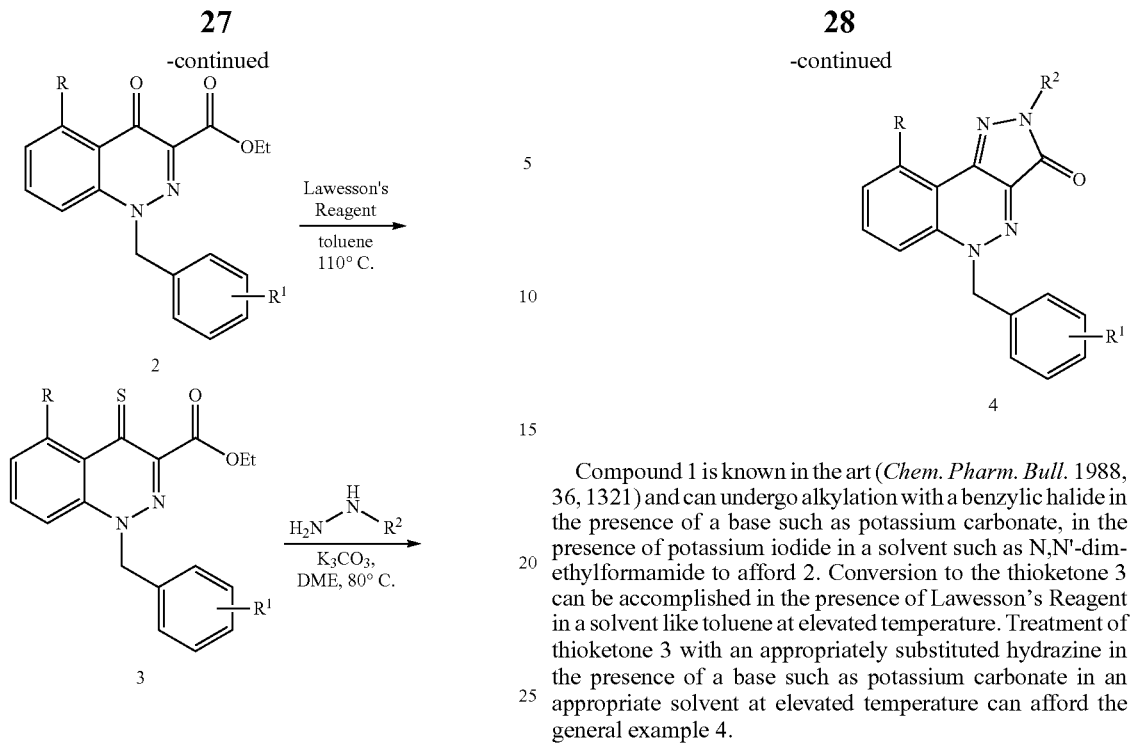

Compound 1 is known in the art (*Chem. Pharm. Bull.* 1988, 36, 1321) and can undergo alkylation with a benzylic halide in the presence of a base such as potassium carbonate, in the presence of potassium iodide in a solvent such as N,N'-dimethylformamide to afford 2. Conversion to the thioketone 3 can be accomplished in the presence of Lawesson's Reagent in a solvent like toluene at elevated temperature. Treatment of thioketone 3 with an appropriately substituted hydrazine in the presence of a base such as potassium carbonate in an appropriate solvent at elevated temperature can afford the general example 4.

Generic Scheme 2:

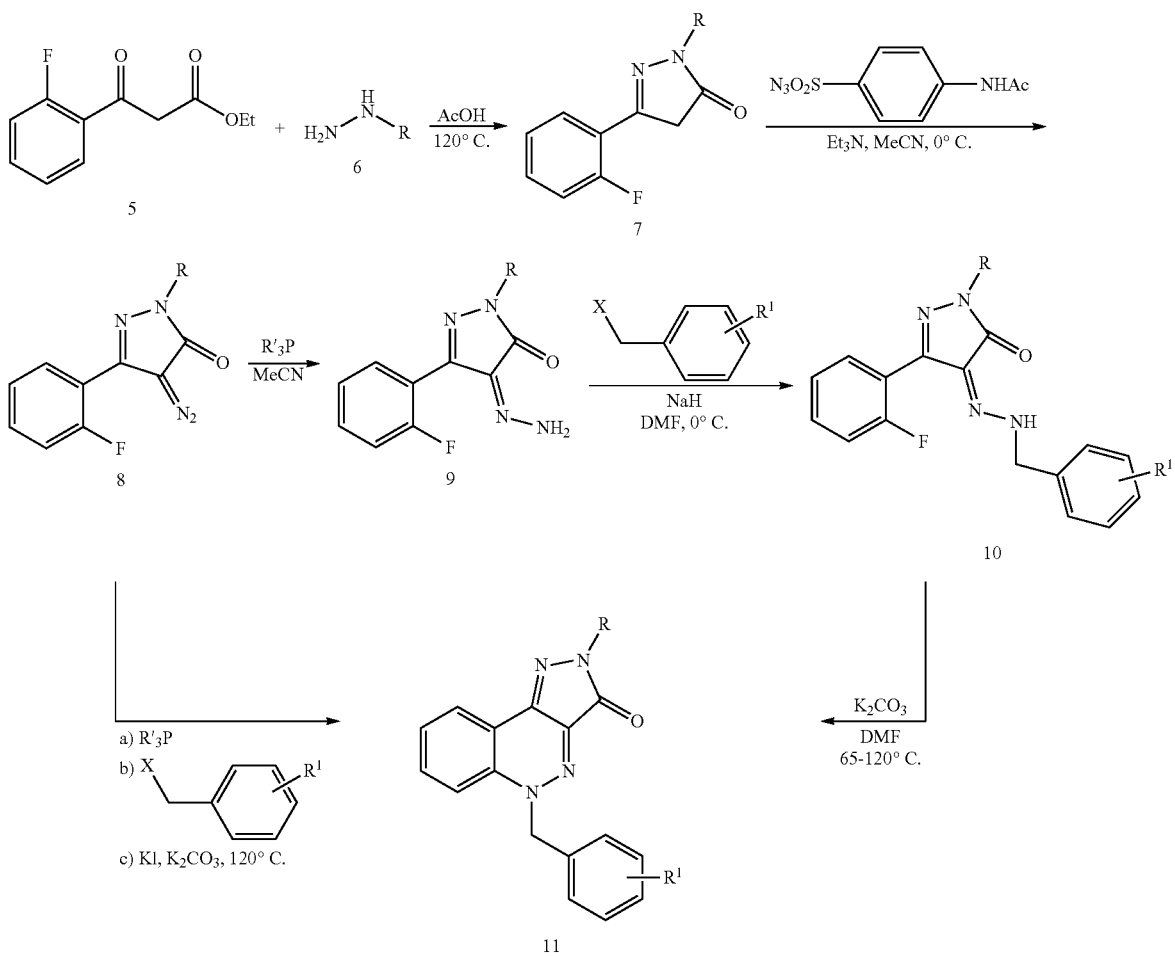

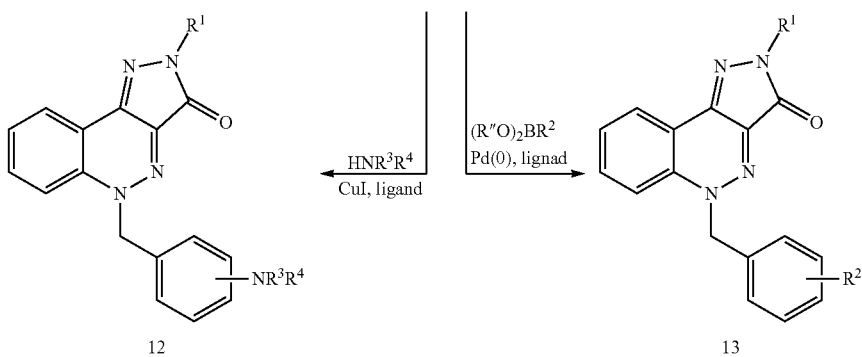

Commercially available β-ketoester 5 can be combined with hydrazine 6 in the presence of an acid, such as acetic acid, at elevated temperature to afford 7, which upon treatment with a diazotranfer agent, such as 4-acetomidobenzenesulfonyl azide provides 8. Phosphine-mediated partial reduction and in situ treatment with an appropriately substituted alkyl halide can directly afford the pyrazolone 11. Alternatively, partial reduction to the hydrazone 9, followed by alkylation with a substituted benzylic halide in the presence of a suitable base like sodium hydride can afford 10. Ring closure can be promoted at elevated temperature in the presence of a base like potassium carbonate and in a solvent such as N,N'-dimethylformamide to afford 11. Further derivatization of 11 ($R^1$=Br or I) can be performed to afford 12, via copper-catalyzed C—N bond-formation in the presence of a suitable catalyst, solvent and ligand. Alternatively, palladium-catalyzed C—C bond formation can be carried out in the presence of a suitable palladium catalyst, ligand and organometallic reagent, which may be aromatic or alkyl and the metal may be boron, tin, zinc, or magnesium, to afford 13.

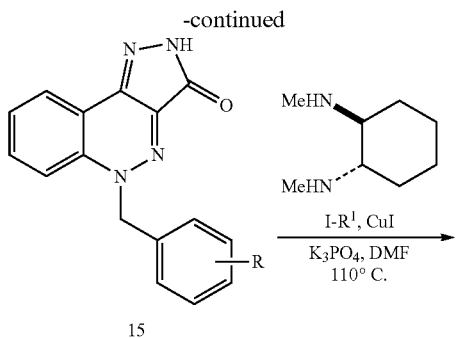

Generic Scheme 3:

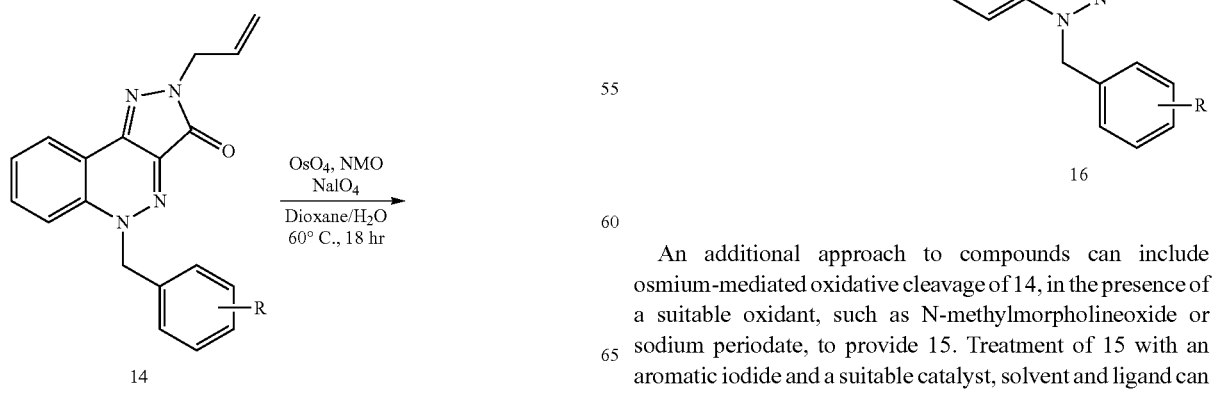

An additional approach to compounds can include osmium-mediated oxidative cleavage of 14, in the presence of a suitable oxidant, such as N-methylmorpholineoxide or sodium periodate, to provide 15. Treatment of 15 with an aromatic iodide and a suitable catalyst, solvent and ligand can afford compound 16.

Generic Scheme 4:
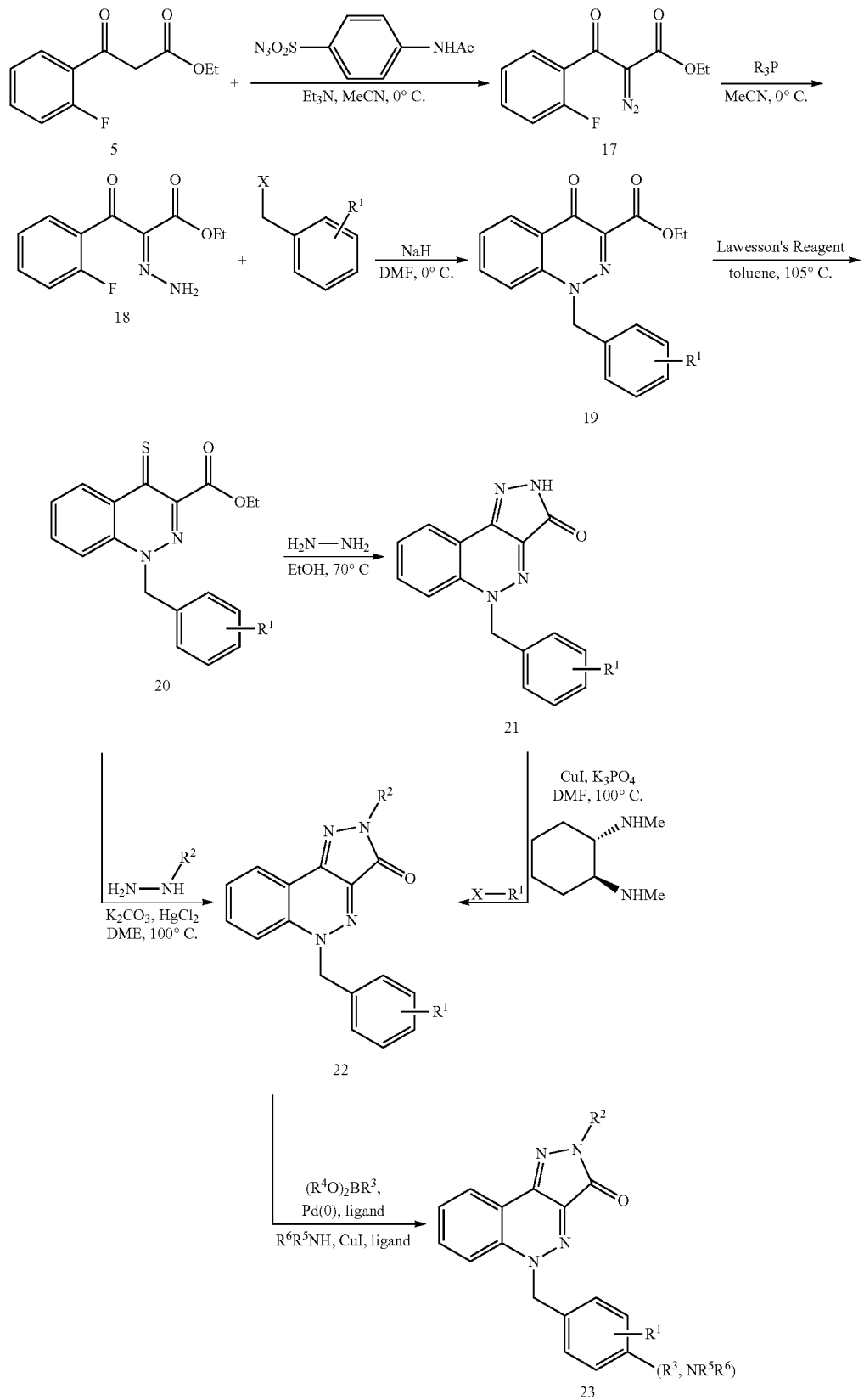

Another approach to compounds includes treatment of β-ketoester 5 with a diazotranfer agent, such as 4-acetomidobenzenesulfonyl azide, to afford diazo 17. Phosphine-mediated reduction can provide the hydrazone 18, which can be alkylated with a benzylic halide in the presence of a base, such as sodium hydride, to provide 19. The thioketone 20 may be obtained by treatment with Lawesson's Reagent at elevated temperature in a solvent like toluene. Compound 20 can be treated with hydrazine in a solvent like ethanol to afford 21, which can in the presence of an aromatic halide and a suitable catalyst, solvent and ligand, afford compound 22. Alternatively, thioketone 20 can be treated with a substituted hydrazine, in the presence of mercury(II) chloride, and afford compound 22 directly. Further elaboration of compound 22 ($R^1$=Br or I) can be performed to afford 23, via copper-catalyzed C—N bond-formation in the presence of a suitable catalyst, solvent and ligand or palladium-catalyzed C—C bond formation can be carried out in the presence of a suitable palladium catalyst, ligand and organometallic reagent, which may be aromatic or alkyl and the metal may be boron, tin, zinc, or magnesium, to afford 23.

The following examples are provided to illustrate the invention and are not to be construed as limiting the scope of the invention in any manner.

Example 1

2-(2-Fluorophenyl)-5-{[4-(1H-pyrazol-1-yl)phenyl]methyl}-2,5-dihydro-3H-pyrazolo[4,3-c]cinnolin-3-one

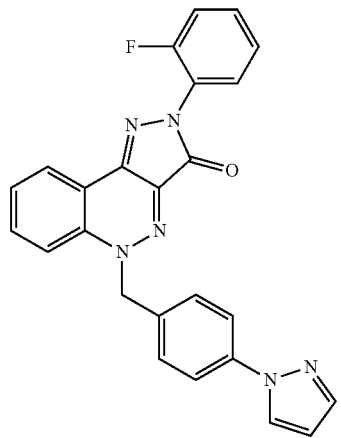 [SMILES: O=c1c2nn(Cc3ccc(-n4cccn4)cc3)c3ccccc3c-2nn1-c1ccccc1F]

Step 1: Preparation of ethyl 4-oxo-1-{[4-(1H-pyrazol-1-yl)phenyl]methyl}-1,4-dihydrocinnoline-3-carboxylate Ethyl 4-oxo-1,4-dihydrocinnoline-3-carboxylate (427 mg, 1.96 mmol) was dissolved in degassed N,N-dimethylformamide (5 mL) and treated with 1-[4-bromomethyl)phenyl]-1H-pyrazole (510 mg, 2.15 mmol, 1.1 equiv) and potassium carbonate (325 mg, 2.35 mmol, 1.2 equiv). The mixture was stirred under nitrogen at ambient temperature for 18 hours and then partitioned between water and ethyl acetate. The combined organic extracts were washed with water and brine, dried over sodium sulfate, filtered and concentrated in vacuo. The residue was purified by silica gradient gel chromatography (100:0 to 90:10; chloroform:methanol), providing the titled compound.

Step 2: Preparation of ethyl 1-{[4-(1H-pyrazol-1-yl)phenyl]methyl}-4-thioxo-1,4-dihydrocinnoline-3-carboxylate Ethyl 4-oxo-1-{[4-(1H-pyrazol-1-yl)phenyl]methyl}-1,4-dihydrocinnoline-3-carboxylate (253 mg, 0.676 mmol) was suspended in toluene (3 mL) and treated with 2,4-bis-(4-methoxyphenyl)-1,3-dithia-2,4-diphosphetane 2,4-disulfide (Lawesson's Reagent, 164 mg, 0.405 mmol, 0.6 equiv). The mixture was heated at 105° C. for 1 hour, cooled to ambient temperature, and concentrated in vacuo. The residue was purified by silica gel chromatography (90:10 to 60:40; hexanes:ethyl acetate), providing the titled compound.

Step 3: Preparation of 2-(2-fluorophenyl)-5-{[4-(1H-pyrazol-1-yl)phenyl]methyl}-2,5-dihydro-31–/–pyrazolo[4,3-c]cinnolin-3-one Ethyl 1-{[4-(1H-pyrazol-1-yl)phenyl]methyl}-4-thioxo-1,4-dihydrocinnoline-3-carboxylate (160 mg, 0.410 mmol) was dissolved in 1,2-dimethoxyethane (2 mL) and absolute ethanol (1 mL). 2-Fluorophenylhydrazine (114 mg, 0.902 mmol, 2.2 equiv) and potassium carbonate (170 mg, 1.23 mmol, 3.0 equiv) were added. The mixture was stirred vigorously for 15 minutes at ambient temperature and then placed into an oil bath preheated to 98° C. for 7 hours. The mixture was cooled ambient temperature, diluted with chloroform and washed once with water. The aqueous layer was extracted once with chloroform and the combined organic extracts were dried with sodium sulfate, filtered and concentrated in vacuo. The residue was purified by silica gel gradient chromatography (100:0 to 99:1; chloroform:methanol), providing the titled compound: $^1$H-NMR (400 MHz, CDCl$_3$) δ 8.32 (1H, d, J=7.8 Hz), 7.90 (1H, s), 7.71-7.61 (4H, m), 7.60-7.52 (3H, m), 7.43-7.37 (3H, m), 7.31-7.26 (2H, m), 6.47 (1H, s), 5.88 (2H, s) ppm; high resolution mass spectrometry (ES+) m/z 437.1517 [(M+H)$^+$; calculated for $C_{25}H_{18}FN_6O$: 437.1521].

The following compounds of formula (II), wherein $R^3$ is absent, were prepared according to the general procedure described in Example 1, substituting the appropriate hydrazine for 2-fluorophenyl hydrazine. The starting materials are either commercially available, known in the literature or may be prepared from commercially available reagents using conventional reactions well known in the art.

(II)

Structure: 2,5-dihydro-3H-pyrazolo[4,3-c]cinnolin-3-one core with R¹ on N2, R³ on benzo ring, and N5 bearing a 4-(1H-pyrazol-1-yl)benzyl group.

| Ex. | R¹ (R³ is absent) | HRMS/LRMS |
|---|---|---|
| 2 | 2-methylphenyl | C$_{26}$H$_{21}$N$_6$O [M + H] calc. 433.1771 obs. 433.1778 |
| 3 | 3,5-dichloropyridin-4-yl | C$_{24}$H$_{16}$Cl$_2$N$_7$O [M + H] calc. 488.0788 obs. 488.0777 |
| 4* | trans-2-hydroxycyclohexyl | C$_{25}$H$_{25}$N$_6$O$_2$ [M + H] calc. 441.2034 obs. 441.2036 |
| 5 | tetrahydro-2H-pyran-4-yl | C$_{24}$H$_{23}$N$_6$O$_2$ [M + H] calc. 427.1877 obs. 427.1875 |
| 6 | tetrahydro-2H-thiopyran-4-yl | C$_{24}$H$_{22}$N$_6$OS [M + H] calc. 443.1649 obs. 443.1642 |
| 7** | 1-oxidotetrahydro-2H-thiopyran-4-yl | Isomer A C$_{24}$H$_{22}$N$_6$O$_2$S [M + H] calc. 459.1598 obs. 459.1604 Isomer B C$_{24}$H$_{22}$N$_6$O$_2$S [M + H] calc. 459.1598 obs. 459.1606 |
| 8 | 1,1-dioxidotetrahydro-2H-thiopyran-4-yl | C$_{24}$H$_{22}$N$_6$O$_3$S [M + H] calc. 475.1 obs. 475.3 |
| 9 | 2,2,6,6-tetramethylpiperidin-4-yl | C$_{28}$H$_{31}$N$_7$O [M + H] calc. 482.2663 obs. 482.2672 |
| 10 | but-3-en-1-yl (allylmethyl) | C$_{22}$H$_{19}$N$_6$O [M + H] calc. 383.1620 obs. 383.1610 |

*Denotes relative trans stereochemistry.
**Denotes both cis and trans isomers.

Example 11

2-(2,3-Dihydroxypropyl)-5-[4-(1H-pyrazol-1-yl)benzyl]-2,5-dihydro-3H-pyrazolo[4,3-c]cinnolin-3-one Allyl-5-[4-(1H-pyrazol-1-yl)benzyl]-2,5-dihydro-3H-pyrazolo[4,3-c]cinnolin-3-one [(Example 10), 600 mg, 1.57 mmol] was dissolved in tetrahydrofuran (65 mL) and water (65 mL), treated with 4-methylmorpholine 4-oxide (221 mg, 1.88 mmol, 1.2 equiv) and osmium tetroxide (50.0 μL, 0.160 mmol, 0.1 equiv). The mixture was stirred for 72 hours at ambient temperature, poured into sodium bicarbonate (200 mL, saturated aqueous) and extracted with ethyl acetate (2×150 mL) and chloroform (2×100 mL). The combined organic extracts were dried with sodium sulfate, filtered and concentrated in vacuo. The sodium sulfate was washed with a 1:1 mixture of methanol:chloroform (6×30 mL) and the filtrate was concentrated in vacuo. The residue was purified via silica gel gradient chromatography (100:0 to 85:15; dichloromethane:methanol), providing the titled compound: $^{1}$H-NMR (400 MHz, CDCl$_3$) δ 8.30-8.26 (1H, m), 7.89 (1H, d, J=2.5 Hz), 7.72-7.67 (3H, m), 7.62-7.54 (3H, m), 7.39 (2H, d, J=8.4 Hz), 6.47-6.45 (1H, m), 5.88 (2H, s), 4.31 (2H, dd, J=5.3, 2.0 Hz), 4.18-4.13 (1H, m), 3.69-3.65 (2H, m), 3.49 (1H, d, J=5.8 Hz), 3.02 (1H, m); high resolution mass spectrometry (ES+) m/z 417.1684 [(M+H)$^+$; calculated for C$_{22}$H$_{21}$N$_6$O$_3$: 417.1670].

Example 12

2-(2-Bromo-6-fluorophenyl)-5-{[4-(1H-pyrazol-1-yl)phenyl]methyl}-2,5-dihydro-3H-pyrazolo[4,3-c]cinnolin-3-one

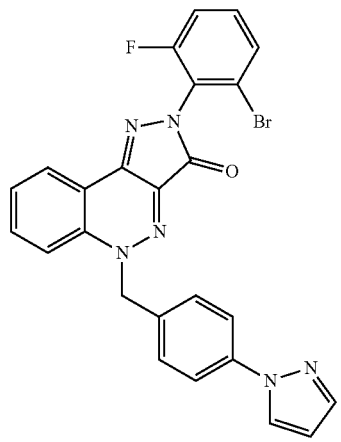 [SMILES: O=c1c2nn(Cc3ccc(-n4cccn4)cc3)c3ccccc3c-2nn1-c1c(F)cccc1Br]

Step 1: Preparation of (2-bromo-6-fluorophenyl)hydrazine hydrochloride

2-Bromo-6-fluoroaniline (2.0 g, 10 mmol) was dissolved in hydrochloric acid (7.0 mL, 12 N aqueous, 8.0 equiv) and cooled to 0° C. An aqueous solution (10 mL) of sodium nitrite (0.80 g, 11 mmol, 1.1 equiv) was added dropwise over 30 minutes via addition funnel and the mixture was stirred for an additional 30 minutes at 0° C. A hydrochloric acid solution (10 mL, 12 N aqueous) of stannous chloride (7.1 g, 31 mmol, 3.0 equiv) was then added to the mixture over 45 minutes via addition funnel and the mixture was stirred for an additional 1 hour at 0° C. To the mixture, sodium hydroxide (30 mL, 1 N aqueous) was added slowly until basic (pH>8). The mixture was warmed to ambient temperature, poured into sodium hydroxide (50 mL, 25% aqueous) and the aqueous layer was extracted with diethyl ether (3×250 mL). The combined organic extracts were dried with sodium sulfate, filtered and partially concentrated in vacuo. The mixture was diluted with diethyl ether (200 mL) and treated with gaseous hydrochloric acid until saturated, resulting in a white precipitate, which was filtered and washed with diethyl ether (2×50 mL), providing the titled compound as a white solid.

Step 2: Preparation of 2-(2-bromo-6-fluorophenyl)-5-{[4-(1H-pyrazol-1-yl)phenyl]methyl}-2,5-dihydro-3H-pyrazolo[4,3-c]cinnolin-3-one Using the procedures described in Example 1, substituting (2-bromo-6-fluorophenyl)hydrazine hydrochloride for (2-fluorophenyl)hydrazine (Step 3), the titled compound was prepared: $^{1}$H-NMR (400 MHz, CDCl$_3$) δ 8.31 (1H, d, J=7.1 Hz), 7.90 (1H, s), 7.73-7.70 (4H, m), 7.59-7.52 (4H, m), 7.44 (2H, d, J=8.3 Hz), 7.40-7.30 (1H, m), 6.47 (1H, s), 5.88 (2H, s) ppm; high resolution mass spectrometry (ES+) m/z 515.0629 [(M+H)$^+$; calculated for C$_{25}$H$_{17}$BrFN$_6$O: 515.0626].

Example 13

3-Fluoro-2-(3-oxo-5-{[4-(1H-pyrazol-1-yl)phenyl]methyl}-3,5-dihydro-2H-pyrazolo[4,3-c]cinnolin-2-yl)benzonitrile

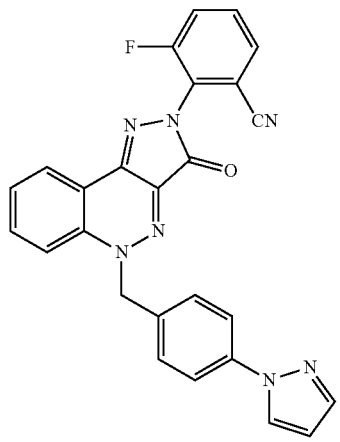 [SMILES: N#Cc1cccc(F)c1-n1nc2c3ccccc3n(Cc3ccc(-n4cccn4)cc3)nc-2c1=O]

2-(2-Bromo-6-fluorophenyl)-5-{[4-(1H-pyrazol-1-yl)phenyl]methyl}-2,5-dihydro-3H-pyrazolo[4,3-c]cinnolin-3-one [(Example 12) 46 mg, 0.089 mmol] was dissolved in degassed N,N-dimethylformamide (1.5 mL) and treated with zinc cyanide (18 mg, 0.15 mmol, 1.7 equiv) and bis(tri-tert-butylphosphine)palladium(0) (9.0 mg, 0.018 mmole, 0.2 equiv). The mixture was stirred under nitrogen at 100° C. for 30 minutes, cooled to ambient temperature, poured into water and extracted twice with ethyl acetate. The combined organic extracts were washed once with water and brine, dried over sodium sulfate, filtered and concentrated in vacuo. The residue was purified by silica gel chromatography (100:0 to 90:10; chloroform:methanol), providing the titled compound: $^{1}$H-NMR (400 MHz, CDCl$_3$) δ 8.32 (1H, d, J=7.8 Hz), 7.90 (1H, s), 7.72 (2H, d, J=9.4 Hz), 7.67-7.51 (7H, m), 7.44 (2H, d, J=9.4 Hz), 6.47 (1H, s), 5.89 (2H, s) ppm; low resolution mass spectrometry (ES+) m/z 461.9 [(M+H)⁺; calculated for $C_{26}H_{16}FN_7O$: 461.4].

Example 14

9-Fluoro-2-(2-fluorophenyl)-5-{[4-(1H-pyrazol-1-yl)phenyl]methyl}-2,5-dihydro-3H-pyrazolo[4,3-c]cinnolin-3-one

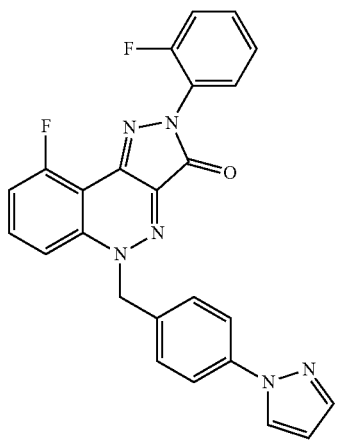 [SMILES: O=c1c2nn(Cc3ccc(-n4cccn4)cc3)c3cccc(F)c3c-2nn1-c1ccccc1F]

Step 1: Preparation of ethyl 3-(2,6-difluorophenyl)-3-oxopropanoate

A mixture of 2,6-difluorobenzoic acid (15 g, 0.095 mol) and carbonyldiimidazole (18 g, 0.14 mol, 1.5 equiv) in anhydrous tetrahydrofuran (150 mL) was stirred at ambient temperature for 6 hours. In a separate flask, a suspension of anhydrous magnesium(II) chloride (9.0 g, 0.095 mol, 1.0 equiv) and potassium ethyl malonate (22 g, 0.13 mol, 1.4 equiv) in tetrahydrofuran (225 mL) was stirred at 50-60° C. for 6 hours, cooled to ambient temperature, which was then added via syringe to the solution of activated acid, and the mixture was stirred for an additional 18 hours at ambient temperature. The mixture was refluxed for 3 hours, cooled to ambient temperature, poured into water and acidified with hydrochloric acid (12 N aqueous) to pH<2. The aqueous layer was extracted with ethyl acetate and the organic extract was washed with water, dried with sodium sulfate, filtered and concentrated in vacuo, providing the titled compound.

Step 2. Preparation of ethyl 2-diazo-3-(2,6-difluorophenyl)-3-oxopropanoate

Ethyl 3-(2,6-difluorophenyl)-3-oxopropanoate (12.3 g, 53.8 mmol) and triethylamine (22.5 mL, 0.161 mol, 3.0 equiv) were dissolved in acetonitrile (160 mL) and treated with 4-acetamidobenzenesulfonyl azide. The mixture was stirred for 18 hours at ambient temperature, concentrated in vacuo and the residue was purified by silica gel chromatography (eluting with chloroform), providing the titled compound.

Step 3. Preparation of ethyl 5-fluoro-4-oxo-1,4-dihydrocinnoline-3-carboxylate

A solution of tri-n-butylphosphine (8.6 g, 0.042 mol, 1.1 equiv) in anhydrous tetrahydrofuran (50 mL) was added to a tetrahydrofuran solution (150 mL) of ethyl 2-diazo-3-(2,6-difluorophenyl)-3-oxopropanoate (9.6 g, 0.038 mol). After stirring for 30 minutes at ambient temperature, the mixture was diluted with tetrahydrofuran (500 mL) and refluxed for 8 hours. The mixture was cooled to ambient temperature, concentrated in vacuo and purified by silica gel gradient chromatography (40:1; chloroform:methanol), providing the titled compound: ¹H NMR (400 MHz, DMSO-d₆) δ 13.85 (1H, br s), 7.78-7.75 (1H, m), 7.50-7.40 (1H, m), 7.27-7.14 (1H, m), 4.30 (2H, t, J=7.1 Hz), 1.30 (3H, t, J=7.1 Hz) ppm; low resolution mass spectrometry (APCI) m/z 237.0 [(M+H)⁺; calculated for $C_{11}H_9FN_2O_3$: 237.1].

Step 4: Preparation of 9-fluoro-2-(2-fluorophenyl)-5-{[4-(1H-pyrazol-1-yl)phenyl]methyl}-2,5-dihydro-3H-pyrazolo[4,3-c]cinnolin-3-one Using the procedures described in Example 1, substituting ethyl 5-fluoro-4-oxo-1,4-dihydrocinnoline-3-carboxylate for ethyl 4-oxo-1,4-dihydrocinnoline-3-carboxylate, the titled compound was obtained: ¹H-NMR (400 MHz, CDCl₃) δ 7.90 (1H, dd, J=2.5, 0.5 Hz), 7.70 (2H, d, J=8.6 Hz), 7.71 (1H, m), 7.64 (1H, ddd, J=7.8, 7.5, 1.9 Hz), 7.53 (1H, dt, J=8.5, 5.7 Hz), 7.40 (2H, d, J=8.6 Hz), 7.42-7.36 (1H, m), 7.30 (1H, d, J=8.8 Hz), 7.30-7.24 (3H, m), 6.46 (1H, dd, J=2.5, 1.8 Hz), 5.83 (2H, s) ppm; high resolution mass spectrometry (ES+) m/z 455.1428 [(M+H)⁺; calculated for $C_{25}H_{17}F_2N_6O$: 455.1426].

The following compounds of formula (IIA), wherein $R^3$ is fluoro, were prepared according to the general procedures described in Example 14, substituting the appropriate hydrazine for 2-fluorophenyl hydrazine. The starting materials are either commercially available, known in the literature or may be prepared from commercially available reagents using conventional reactions well known in the art.

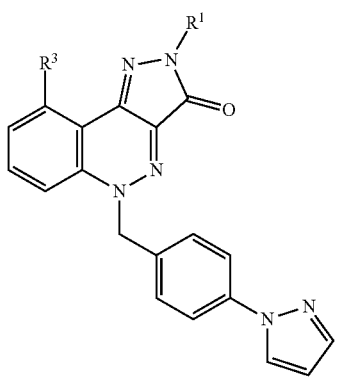

(IIA)

| Ex. | R¹ (R³ is fluoro) | HRMS |
|---|---|---|
| 15 | Me, (ortho-methylphenyl) | $C_{26}H_{20}FN_6O$ [M + H] calc. 451.1677 obs. 451.1677 |

41
-continued

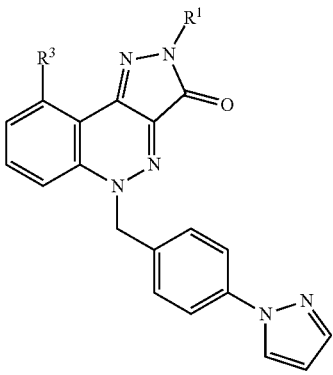

| Ex. | R¹ (R³ is fluoro) | HRMS |
|---|---|---|
| 16 | (tetrahydropyran-4-yl-methyl) | $C_{24}H_{22}FN_6O_2$ [M + H] calc. 445.1783 obs. 445.1783 |
| 17 | (1,1-dioxo-tetrahydrothiopyran-4-yl-methyl) | $C_{24}H_{21}FN_6O_3S$ [M + H] calc. 493.1453 obs. 493.1463 |

Example 18

9-Fluoro-2-(2-fluorophenyl)-5-{[4-(1H-imidazol-1-yl)phenyl]methyl}-2,5-dihydro-3H-pyrazolo[4,3-c]cinnolin-3-one

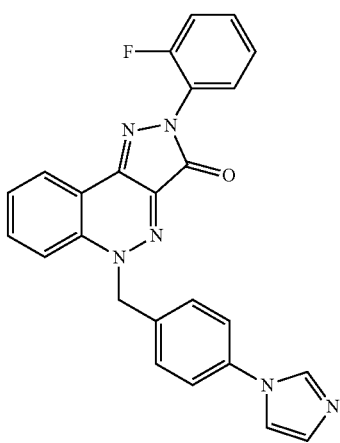 [SMILES: O=c1c2nn(Cc3ccc(-n4ccnc4)cc3)c3ccccc3c-2nn1-c1ccccc1F]

42

Step 1: Preparation of 2,5-bis(2-fluorophenyl)-2,4-dihydro-3H-pyrazol-3-one

Ethyl 3-(2-fluorophenyl)-3-oxopropanoate (2.5 g, 12 mmol) and 2-fluorophenyl hydrazine hydrochloride (1.5 g, 12 mmol, 1.0 equiv) were dissolved in acetic acid (24 mL) and placed into a preheated oil bath at 120° C. for 3 hours and then heated for an additional 2 hours at 135° C. The mixture was cooled to ambient temperature, concentrated in vacuo and then concentrated once from toluene (1×25 mL). The residue was suspended in dichloromethane, filtered and the solid was washed once with dichloromethane and dried in vacuo, providing the titled compound. The resulting filtrate was concentrated in vacuo and purified by silica gel gradient chromatography (100:0 to 65:35; hexanes:ethyl acetate), providing additional titled compound as a light brown solid.

Step 2: Preparation of 4-diazo-2,5-bis(2-fluorophenyl)-2,4-dihydro-3H-pyrazol-3-one 2,5-Bis(2-fluorophenyl)-2,4-dihydro-3H-pyrazol-3-one (0.63 g, 2.3 mmol) was suspended in acetonitrile (10 mL), treated with triethylamine (0.27 mL, 2.7 mmol, 1.15 equiv) and cooled to 0° C. To the mixture was added 4-acetamidobenzenesulfonyl azide (0.61 g, 2.5 mmol, 1.1 equiv) and after 30 minutes at 0° C., the mixture was warmed to ambient temperature. After stirring for 30 minutes, the mixture was poured into sodium carbonate (25 mL, aqueous saturated) and sodium hydroxide (10 mL, 1 N aqueous) and extracted with dichloromethane (2×125 mL). The combined organic extracts were dried with sodium sulfate, filtered and concentrated in vacuo. The residue was purified by silica gel gradient chromatography (100:0 to 0:100; hexanes:ethyl acetate), providing the titled compound.

Step 3: Preparation of 9-fluoro-2-(2-fluorophenyl)-5-{[4-(1H-imidazol-1-yl)phenyl]methyl}-2,5-dihydro-3H-pyrazolo[4,3-c]cinnolin-3-one 4-Diazo-2,5-bis(2-fluorophenyl)-2,4-dihydro-3H-pyrazol-3-one (0.17 g, 0.56 mmol) was dissolved in acetonitrile (5 mL) and treated with tri-n-butylphosphine (0.11 g, 0.56 mmol, 1.0 equiv). After stirring for 30 minutes at ambient temperature, 1-[4-(chloromethyl)phenyl]-1H-imidazole (0.11 g, 0.56 mmol, 1.0 equiv), potassium iodide (47 mg, 0.28 mmol, 0.5 equiv) and potassium carbonate (97 mg, 0.70 mmol, 1.25 equiv) were added at ambient temperature. After 45 minutes, the reaction mixture was warmed to 85° C., stirred for 2.5 hours and then cooled to ambient temperature. The mixture was poured into water (100 mL), extracted with ethyl acetate (2×75 mL) and the combined organic extracts were dried with sodium sulfate, filtered and concentrated in vacuo. The residue was purified twice by silica gel gradient chromatography (100:0 to 0:100; hexanes:ethyl acetate containing 10% methanol; and then 100:0 to 90:10; dichloromethane:methanol containing 10% ammonium hydroxide), providing the titled compound as a deep red solid: ¹H-NMR (400 MHz, CDCl₃) δ 8.33 (1H, dd, J=7.6, 1.8 Hz), 7.85 (1H, br s), 7.67-7.53 (4H, m), 7.46 (2H, d, J=8.5 Hz), 7.40 (2H, d, J=8.5 Hz), 7.42-7.37 (1H, m), 7.31-7.20 (4H, m), 5.88 (2H, s) ppm; high resolution mass spectrometry (ES+) m/z 437.1526 [(M+H)+; calculated for $C_{25}H_{18}FN_6O$: 437.1521].

Example 19

2-(2-Fluorophenyl)-5-[(4-iodophenyl)methyl]-2,5-dihydro-3H-pyrazolo[4,3-c]cinnolin-3-one

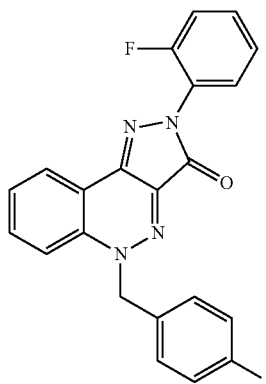

Step 1: Preparation of 1,3-bis(2-fluorophenyl)-1H-pyrazole-4,5-dione 4-hydrazone 4-Diazo-2,5-bis(2-fluorophenyl)-2,4-dihydro-3H-pyrazol-3-one [(Example 18, Step 2) 213 mg, 0.714 mmol] was dissolved in acetonitrile (10 mL) and treated with triphenylphosphine (225 mg, 0.857 mmol, 1.2 equiv). After stirring for 30 minutes at ambient temperature, the mixture was treated with methanol (5 mL) and water (5 mL) and warmed to 60° C. for 1 hour. The mixture was cooled to ambient temperature, poured into brine (50 mL) and sodium bicarbonate (20 mL, aqueous saturated) and extracted with ethyl acetate (2×100 mL). The combined organic extracts were dried with sodium sulfate, filtered and concentrated in vacuo. The residue was purified by silica gel gradient chromatography (100:0 to 70:30; hexanes:ethyl acetate), providing the titled compound.

Step 2: Preparation of 1,3-bis(2-fluorophenyl)-1H-pyrazole-4,5-dione 4-{[(4-iodophenyl)methyl]hydrazone}

1,3-Bis(2-fluorophenyl)-1H-pyrazole-4,5-dione-4-hydrazone (57 mg, 0.19 mmol) and 4-iodobenzylbromide (56 mg, 0.19 mmol, 1.0 equiv) were dissolved in degassed N,N-dimethylformamide (3 mL), cooled to 0° C. and treated with sodium hydride (17 mg, 0.43 mmol, 2.2 equiv). After stirring at 0° C. for 1.5 hours, the mixture was treated with ammonium chloride (3 mL, aqueous saturated), poured into water (15 mL) and extracted with ethyl acetate (2×50 mL). The combined organic extracts were dried with sodium sulfate, filtered and concentrated in vacuo. The residue was purified by silica gel gradient chromatography (100:0 to 1:1; hexanes:ethyl acetate), providing the titled compound as a light yellow solid.

Step 3: Preparation of 2-(2-fluorophenyl)-5-[(4-iodophenyl)methyl]-2,5-dihydro-3H-pyrazolo[4,3-c]cinnolin-3-one 1,3-Bis(2-fluorophenyl)-1H-pyrazole-4,5-dione 4-{[(4-iodophenyl)methyl]hydrazone} (50 mg, 0.097 mmol) was dissolved in degassed dimethylsulfoxide (3.5 mL), treated with potassium carbonate (120 mg, 0.87 mmol, 9.0 equiv) and placed into an oil bath preheated to 120° C. for 15 minutes. The mixture was cooled to ambient temperature, poured into sodium bicarbonate (50 mL, aqueous saturated) and extracted with ethyl acetate (2×75 mL). The combined organic extracts were dried with sodium sulfate, filtered and concentrated in vacuo. The residue was purified by silica gel gradient chromatography (100:0 to 20:80; hexanes:ethyl acetate), providing the titled compound as a dark red solid: $^1$H-NMR (400 MHz, CDCl$_3$) δ 8.32 (1H, d, J=7.7 Hz), 7.70 (2H, d, J=8.3 Hz), 7.66-7.62 (1H, m), 7.59-7.55 (2H, m), 7.49 (1H, d, J=8.9 Hz), 7.42-7.36 (1H, m), 7.31-7.25 (2H, m), 7.07 (2H, d, J=8.0 Hz), 5.77 (2H, s) ppm; high resolution mass spectrometry (ES+) m/z 497.0278 [(M+H)+; calculated for $C_{22}H_{15}FIN_4O$: 497.0269].

Example 20

2-(2-Fluorophenyl)-5-{[4-(1,3-thiazol-4-yl)phenyl]methyl}-2,5-dihydro-3H-pyrazolo[4,3-c]cinnolin-3-one

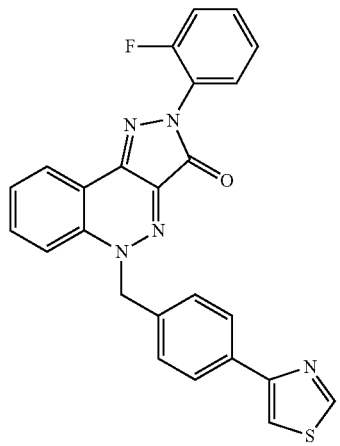 [SMILES: O=c1c2nn(Cc3ccc(-c4cscn4)cc3)c3ccccc3c-2nn1-c1ccccc1F]

2-(2-Fluorophenyl)-5-[(4-iodophenyl)methyl]-2,5-dihydro-3H-pyrazolo[4,3-c]cinnolin-3-one [(Example 19) 25 mg, 0.050 mmol] and 4-(tributylstannyl)thiazole (28 mg, 0.076 mmole, 1.5 equiv) were dissolved in degassed N,N-dimethylformamide (1 mL) and treated with cesium fluoride (15 mg, 0.101 mmol, 2 equiv), copper(I) iodide (4 mg, 0.020 mmol, 0.4 equiv), and tetrakis(triphenylphosphine)palladium(0) (12 mg, 0.010 mmol, 0.2 equiv). The mixture was stirred at ambient temperature for one hour, diluted with ethyl acetate (15 mL) and filtered. The solids were discarded, the filtrate was concentrated in vacuo and the residue was purified by preparative reverse phase HPLC (20:80 to 80:20; acetonitrile containing 0.1% trifluoroacetic acid:water containing 0.1% trifluoroacetic acid), providing the titled compound: $^1$H-NMR (400 MHz, CDCl$_3$) δ 8.99 (1H, s), 8.34 (1H, d, J=8.3 Hz), 7.89 (2H, d, J=8.2 Hz), 7.69-7.55 (6H, m), 7.41 (2H, d, J=8.2 Hz), 7.32-7.24 (2H, m), 5.90 (2H, s) ppm; low resolution mass spectrometry (ES+) m/z 453.9 [(M+H)+; calculated for $C_{25}H_{16}FN_5OS$: 453.4]

Example 21

5-[(5-Bromopyridin-2-yl)methyl]-2-(2-methylphenyl)-2,5-dihydro-3H-pyrazolo[4,3-c]cinnolin-3-one

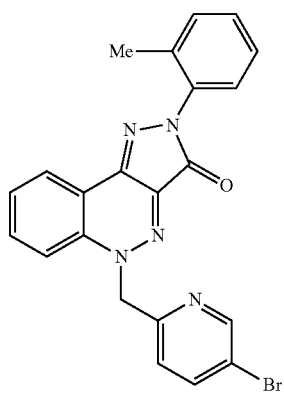 [SMILES: Cc1ccccc1-n1nc2c3ccccc3n(Cc3ccc(Br)cn3)nc-2c1=O]

Using the procedures described in Example 19, substituting (5-bromopyridin-2-yl)methyl methanesulfonate for 4-iodobenzylbromide, the titled compound was obtained: $^1$H-NMR (400 MHz, CDCl$_3$) δ 8.68 (1H, s), 8.30 (1H, d, J=6.4 Hz), 7.80 (1H, d, J=8.0 Hz), 7.75 (1H, d, J=9.4 Hz) 7.65-7.53 (2H, m), 7.45 (1H, dd, J=3.9, 1.5 Hz), 7.38-7.30 (4H, m), 5.89 (2H, s), 2.36 (3H, s) ppm; high resolution mass spectrometry (ES+) m/z 446.0629 [(M+H)+; calculated for $C_{22}H_{17}BrN_5O$: 446.0611].

Example 22

5-[(6-Bromopyridin-3-yl)methyl]-2-(2-methylphenyl)-2,5-dihydro-3H-pyrazolo[4,3-c]cinnolin-3-one

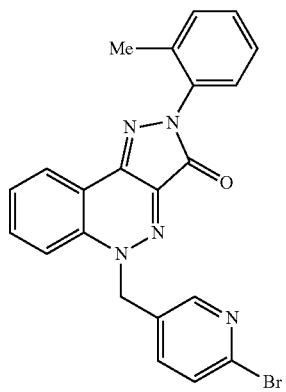 [SMILES: Cc1ccccc1-n1nc2c3ccccc3n(Cc3ccc(Br)nc3)nc-2c1=O]

Using the procedures described in Example 19, substituting (6-bromopyridin-3-yl)methyl methanesulfonate for 4-iodobenzylbromide, the title compound was obtained: $^1$H-NMR (400 MHz, CDCl$_3$) δ 8.49 (1H, s), 8.32 (1H, d, J=8.9 Hz), 7.67-7.53 (3H, m), 7.50-7.43 (3H, m), 7.39-7.31 (3H, m), 5.81 (2H, s), 2.35 (3H, s) ppm; high resolution mass spectrometry (ES+) m/z 446.0621 [M+H)'; calculated for $C_{22}H_{17}BrN_5O$: 446.0611].

Example 23

5-{[6-(1H-Imidazol-1-yl)pyridine-3-yl]methyl}-2-(2-methylphenyl)-2,5-dihydro-3H-pyrazolo[4,3-c]cinnolin-3-one

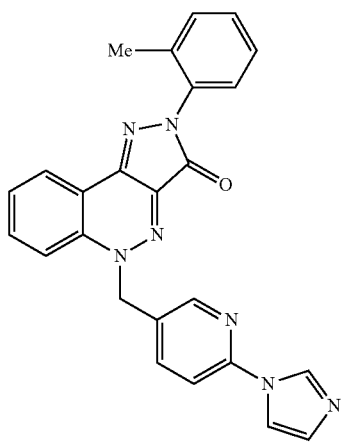 [SMILES: Cc1ccccc1-n1nc2c3ccccc3n(Cc3ccc(-n4ccnc4)nc3)nc-2c1=O]

5-[(6-Bromopyridin-3-yl)methyl]-2-(2-methylphenyl)-2,5-dihydro-3H-pyrazolo[4,3-c]cinnolin-3-one [(Example 22) 80 mg, 0.18 mmol] was dissolved in dimethyl sulfoxide (1 mL) and treated with imidazole (49 mg, 0.72 mmol, 4 equiv), copper (I) iodide (14 mg, 0.072 mmol, 0.4 equiv), and (±)-trans-N,N'-dimethylcyclohexane-1,2-diamine (20 mg, 0.14 mmol, 0.8 equiv). An aqueous solution (0.2 mL) of tribasic potassium phosphate (0.11 g, 0.54 mmol, 3 equiv) was added and the mixture was placed into a preheated oil bath at 75° C. for 2 hours. The mixture was cooled to ambient temperature, poured into water and extracted twice with ethyl acetate. The combined organic extracts were washed once with water and brine, dried with sodium sulfate, filtered and concentrated in vacuo. The residue was purified by silica gel gradient chromatography (100:0 to 94:6; chloroform:methanol), providing the titled compound: $^1$H-NMR (400 MHz, CDCl$_3$) δ 8.58 (1H, s), 8.43 (1H, br s), 8.33 (1H, d, J=6.9 Hz), 7.85 (1H, d, J=9.7 Hz), 7.77 (1H, br s), 7.68-7.54 (3H, m), 7.45 (1H, m), 7.38-7.32 (5H, m), 5.88 (2H, s), 2.36 (3H, s) ppm; high resolution mass spectrometry (ES+) m/z 434.1736 [(M+H)+; calculated for $C_{25}H_{20}N_7O$: 434.1724].

Example 24

2-(2-Methylphenyl)-5-{[6-(1H-pyrazol-1-yl)pyridine-3-yl]methyl}-2,5-dihydro-3H-pyrazolo[4,3-c]cinnolin-3-one

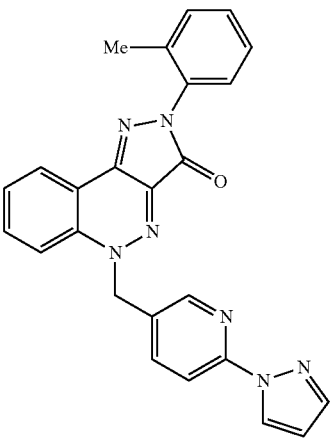 [SMILES: Cc1ccccc1-n1nc2c3ccccc3n(Cc3ccc(-n4cccn4)nc3)nc-2c1=O]

Using the procedures described in Example 23, substituting pyrazole for imidazole, the title compound was obtained: $^1$H-NMR (400 MHz, CDCl$_3$) δ 8.56-8.45 (2H, m), 8.33 (1H, s), 7.99 (1H, br s), 7.82 (1H, d, J=8.3 Hz), 7.73 (1H, s), 7.66-7.54 (4H, m), 7.39-7.30 (3H, m), 6.46 (1H, br s), 5.88 (2H, s), 2.38 (3H, s) ppm; high resolution mass spectrometry (ES+) m/z 434.1733 [(M+H)+; calculated for $C_{25}H_{20}N_7O$: 434.1724].

Example 25

2-(2-Methylphenyl)-5-{[6-(1-methyl-1H-pyrazol-4-yl)pyridine-3-yl]methyl}-2,5-dihydro-3H-pyrazolo[4,3-c]cinnolin-3-one

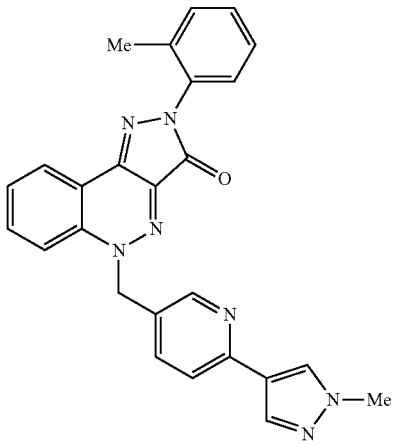 [SMILES: Cc1ccccc1-n1nc2c3ccccc3n(Cc3ccc(-c4cnn(C)c4)nc3)nc-2c1=O]

5-[(6-Bromopyridin-3-yl)methyl]-2-(2-methylphenyl)-2,5-dihydro-3H-pyrazolo[4,3-c]cinnolin-3-one [(Example 22) 74 mg, 0.17 mmol] was dissolved in dimethyl sulfoxide (1 mL) and treated with 1-methyl-4-(4,4,5,5-tetramethyl-1,3,2-dioxaborolan-2-yl)-1H-pyrazole (59 mg, 0.28 mmol, 1.7 equiv), 2-(dicyclohexylphosphino)-2',4',6'-tri-iso-propylbiphenyl (X-PHOS, 36 mg, 0.076 mmol, 0.46 equiv), palladium (II) acetate (8.0 mg, 0.033 mmol, 0.2 equiv), and an aqueous solution (0.2 mL) of potassium carbonate (69 mg, 0.50 mmol, 3.0 equiv). The mixture was placed into an oil bath preheated at 80° C. for 30 minutes, cooled to ambient temperature, poured into water and extracted twice with ethyl acetate. The combined organic extracts were washed once with water and brine, dried with sodium sulfate, filtered and concentrated in vacuo. The residue was purified by silica gel gradient chromatography (100:0 to 94:6; chloroform:methanol), providing the titled compound: $^1$H-NMR (400 MHz, CDCl$_3$) δ 8.63 (1H, s), 8.31 (1H, d, J=7.5 Hz), 7.93 (1H, s), 7.91 (1H, s), 7.68-7.53 (4H, m), 7.47-7.41 (2H, m), 7.38-7.31 (3H, m), 5.84 (2H, s), 3.96 (3H, s), 2.38 (3H, s) ppm; high resolution mass spectrometry (ES+) m/z 448.1885 [(M+H)+; calculated for $C_{26}H_{22}N_7O$: 448.1880].

The following compounds of formula (IIIA) (wherein $R^7$ is methyl) were prepared according to the general procedure described in Example 25, substituting the appropriate boronic acid or appropriately substituted boronic ester for 1-methyl-4-(4,4,5,5-tetramethyl-1,3,2-dioxaborolan-2-yl)-1H-pyrazole. The starting materials are either commercially available, known in the literature or may be prepared from commercially available reagents using conventional reactions well known in the art.

(IIIA)

| Ex. | $R^2$ ($R^7$ is methyl) | HRMS/LRMS |
|---|---|---|
| 26 | ![structure with phenyl-NHC(O)Me] | $C_{30}H_{25}N_6O_2$ [M + H] calc. 501.2034 obs. 501.2043 |
| 27 | ![structure with pyridin-3-yl] | $C_{27}H_{21}N_6O$ [M + H] calc. 445.1771 obs. 445.1760 |

-continued (IIIA)

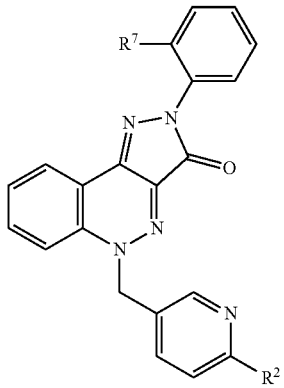

| Ex. | R² (R⁷ is methyl) | HRMS/LRMS |
|---|---|---|
| 28 |  pyridine-morpholine | $C_{31}H_{28}N_7O_2$ [M + H] calc. 530.2299 obs. 530.2292 |
| 29 | pyridine-CH₃ | $C_{28}H_{23}N_6O$ [M + H] calc. 459.1928 obs. 459.1931 |

Example 30

2-(2-Fluoro-3-methylpyridin-4-yl)-5-{[4-(1H-pyrazol-1-yl)phenyl]methyl}-2,5-dihydro-3H-pyrazolo[4,3-c]cinnolin-3-one

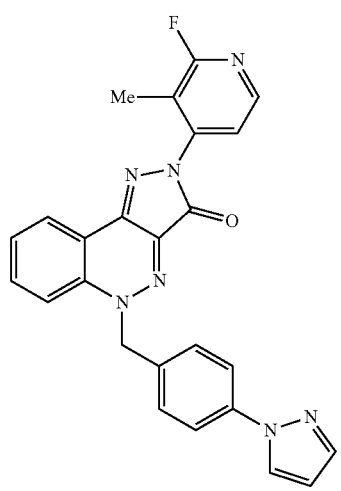 [SMILES: Cc1c(-n2nc3c4ccccc4n(Cc4ccc(-n5cccn5)cc4)nc-3c2=O)ccnc1F]

Step 1: Preparation of 5-{[4-(1H-pyrazol-1-yl)phenyl]methyl}-2,5-dihydro-3H-pyrazolo[4,3-c]cinnolin-3-one 2-Prop-2-en-1-yl-5-{[4-(1H-pyrazol-1-yl)phenyl]methyl}-2,5-dihydro-3H-pyrazolo[4,3-c]cinnolin-3-one [(Example 10), 209 mg, 0.547 mmol], N-methylmorpholine oxide (192 mg, 1.64 mmol, 3.0 equiv), osmium(VIII)tetraoxide (69.5 mg, 0.273 mmol, 0.5 equiv) and sodium periodate (292 mg, 1.37 mmol, 2.5 equiv) were combined in dioxane (10 mL) and water (1 mL) and placed into an oil bath preheated to 60° C. for 18 hours. The mixture was cooled to ambient temperature, poured into sodium bicarbonate (20 mL, aqueous saturated) and extracted with ethyl acetate (3×25 mL). The combined organic extracts were dried with sodium sulfate, filtered and concentrated in vacuo. The residue was purified by silica gel gradient chromatography (100:0 to 90:10; dichloromethane:methanol), providing the titled compound.

Step 2: Preparation of 2-(2-fluoro-3-methylpyridin-4-yl)-5-{[4-(1H-pyrazol-1-yl)phenyl]methyl}-2,5-dihydro-3H-pyrazolo[4,3-c]cinnolin-3-one 5-{[4-(1H-Pyrazol-1-yl)phenyl]methyl}-2,5-dihydro-3H-pyrazolo[4,3-c]cinnolin-3-one (25 mg, 0.073 mmol), copper (I)iodide (14 mg, 0.073 mmol, 1 equiv), tribasic potassium phosphate (93 mg, 0.44 mmol, 6.0 equiv), (±)-trans-N,N'-bismethyl-1,2-cyclohexanediamine (31 mg, 3.0 equiv) and 2-fluoro-4-iodo-3-picoline (52 mg, 0.22 mmol, 3.0 equiv) were combined in degassed N,N-dimethylformamide (3 mL) and the mixture was placed into an oil bath preheated to 110° C. for 1 hour. The mixture was cooled to ambient temperature, poured into sodium bicarbonate (25 mL, aqueous saturated) and extracted with ethyl acetate (3×50 mL). The combined organic extracts were dried with sodium sulfate, filtered and concentrated in vacuo. The residue was purified by silica gel gradient chromatography (100:0 to 0:100; hexanes:ethyl acetate), providing the titled compound: ¹H-NMR (400 MHz, CDCl₃) δ 8.32 (1H, d, J=8.1 Hz), 8.15 (1H, d, J=5.3 Hz), 7.91 (1H, d, J=2.5 Hz), 7.72 (2H, d, J=8.5 Hz), 7.72 (1H, m), 7.67-7.59 (3H, m), 7.46 (1H, m), 7.43 (2H, d, J=8.3 Hz), 6.47 (1H, m), 5.89 (2H, s), 2.37 (3H, s) ppm; high resolution mass spectrometry (ES+) m/z 452.1623 [(M+H)⁺; calculated for $C_{25}H_{19}FN_7O$: 452.1630].

Example 31

(±)-5-[4-(1H-pyrazol-1-yl)benzyl]-2-(tetrahydro-2H-pyran-3-yl)-2,5-dihydro-3H-pyrazolo[4,3-c]cinnolin-3-one

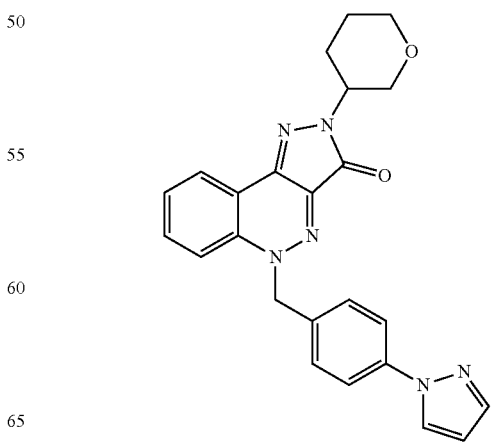

Step 1: Preparation of ethyl 2-diazo-3-(2-fluorophenyl)-3-oxopropanoate

Ethyl 3-(2-fluorophenyl)-3-oxopropanoate (1.00 g, 4.76 mmol) was dissolved in acetonitrile (14 mL) and treated with triethylamine (0.760 ml, 5.47 mmol, 1.15 equiv). The mixture was cooled to 0° C., treated with 4-acetamidobenzenesulfonylazide (1.26 g, 5.23 mmol, 1.1 equiv) and warmed to ambient temperature over 1.5 hours. The mixture was partially concentrated in vacuo, cooled to 0° C., treated with sodium hydroxide (50 mL, 1 N aqueous) and extracted with chloroform (3×50 mL). The combined organic extracts were dried with sodium sulfate, filtered and concentrated in vacuo. The residue was purified via silica gel gradient chromatography (100:0 to 85:15; hexanes:ethyl acetate) providing the titled compound as a yellow oil.

Step 2: Preparation of ethyl 3-(2-fluorophenyl)-2-hydrazono-3-oxopropanoate

Ethyl 2-diazo-3-(2-fluorophenyl)-3-oxopropanoate (1.06 g, 4.49 mmol) was dissolved in acetonitrile (20 mL), cooled to 0° C. and treated with tri-n-butylphosphine (1.16 mL, 4.71 mmol, 1.05 equiv). The mixture was warmed to ambient temperature and after 10 minutes, was concentrated in vacuo. The residue was purified via silica gel gradient chromatography (100:0 to 75:25; hexanes:ethyl acetate) to provide the titled compound.

Step 3: Preparation of ethyl 4-oxo-1-[4-(1H-pyrazol-1-yl)benzyl]-1,4-dihydrocinnoline-3-carboxylate Ethyl 3-(2-fluorophenyl)-2-hydrazono-3-oxopropanoate (1.16 g, 4.87 mmol) and 1-[4-(bromomethyl)phenyl]-1H-pyrazole (1.50 g, 6.33 mmol, 1.3 equiv) were dissolved in degassed N,N-dimethylformamide (15 mL), cooled to 0° C. and treated with sodium hydride (0.312 g, 7.79 mmol, 1.6 equiv). After stirring for 1 hour at 0° C., the mixture was treated with ammonium chloride (3 mL, saturated aqueous) and water (40 mL) and extracted with ethyl acetate (3×75 mL). The combined organic extracts were dried with sodium sulfate, filtered and concentrated in vacuo. The residue was purified by silica gel gradient chromatography (100:0 to 20:80; hexanes:ethyl acetate) to provide the titled compound.

Step 4: Preparation of ethyl 1-[4-(1H-pyrazol-1-yl)benzyl]-4-thioxo-1,4-dihydrocinnoline-3-carboxylate Ethyl 4-oxo-1-[4-(1H-pyrazol-1-yl)benzyl]-1,4-dihydrocinnoline-3-carboxylate (750 mg, 2.00 mmol) was dissolved in toluene (9 mL), sparged under nitrogen and treated with Lawesson's Reagent (486 mg, 1.20 mmol, 0.6 equiv). The mixture was placed into an oil bath preheated to 105° C. for 1 hour, cooled to ambient temperature and concentrated in vacuo. The residue was purified by silica gel gradient chromatography (100:0 to 60:40; hexanes:ethyl acetate) to provide the titled compound as a dark green solid.

Step 5: Preparation of (±)-tert-butyl 2-(tetrahydro-2H-pyran-3-yl)hydrazinecarboxylate Dihydro-2H-pyran-3(4H)-one (100 mg, 1.00 mmol), tert-butyl carbazate (145 mg, 1.10 mmol, 1.1 equiv) and acetic acid (0.280 mL, 4.99 mmol, 5 equiv) were combined in 1,2-dichloroethane (3 mL), stirred at ambient temperature for 10 minutes and treated with sodium triacetoxyborohydride (296 mg, 1.34 mmol, 1.4 equiv). After stirring for 1 hour, the mixture was poured into water and extracted with ethyl acetate (3×50 mL). The combined organic extracts were dried with sodium sulfate, filtered and concentrated in vacuo to provide the titled compound.

Step 6: Preparation of (±)-tetrahydro-2H-pyran-3-ylhydrazine hydrochloride (±)-tert-Butyl 2-(tetrahydro-2H-pyran-3-yl)hydrazinecarboxylate (216 mg, 1.00 mmol) was dissolved in dichloromethane (10 mL) and ethyl acetate (10 mL) and cooled to 0° C. The mixture was saturated with gaseous hydrogen chloride, warmed to ambient temperature and stirred for 1 hour. The mixture was concentrated in vacuo and the residue was concentrated with toluene (2×20 mL) to afford the titled compound.

Step 7: Preparation of (±)-5-[4-(1H-pyrazol-1-yl)benzyl]-2-(tetrahydro-2H-pyran-3-yl)-2,5-dihydro-3H-pyrazolo[4,3-c]cinnolin-3-one Ethyl 1-[4-(1H-pyrazol-1-yl)benzyl]-4-thioxo-1,4-dihydrocinnoline-3-carboxylate (200 mg, 0.510 mmol) and (±)-tetrahydro-2H-pyran-3-ylhydrazine hydrochloride (172 mg, 1.13 mmol, 2.2 equiv) were dissolved in N,N-dimethylformamide (10 mL) and acetonitrile (10 mL). The solution was sparged under nitrogen, treated with potassium carbonate (708 mg, 5.12 mmol, 10 equiv) and mercury(II)chloride (139 mg, 0.51 mmol, 1 equiv) and stirred at ambient temperature for 14 hours. The mixture was poured into water and extracted with ethyl acetate (3×70 mL) and the combined organic extracts were dried with sodium sulfate, filtered and concentrated in vacuo. The residue was purified by silica gel gradient chromatography (100:0 to 0:100; hexanes:ethyl acetate) to provide the titled compound as a dark red solid: $^1$H-NMR (400 MHz, CDCl$_3$) δ 8.33-8.29 (1H, m), 7.88 (1H, d, J=2.5 Hz), 7.74 (1H, d, J=1.8 Hz), 7.66 (2H, d, J=8.7 Hz), 7.61-7.56 (3H, m), 7.40 (2H, d, J=8.6 Hz), 6.47 (1H, dd, J=2.4, 1.9 Hz), 5.85 (2H, s), 4.77-4.69 (1H, m), 4.06 (1H, ddd, J=10.8, 4.4, 1.6 Hz), 4.00 (1H, d, J=11.0 Hz), 3.84 (1H, ap t, J=10.6 Hz), 3.55-3.48 (1H, m), 2.31-2.19 (1H, m), 2.17-2.10 (1H, m), 1.92-1.83 (2H, m) ppm; high resolution mass spectrometry (ES+) m/z 427.1872 [(M+H)$^+$; calculated for C$_{24}$H$_{22}$N$_6$O$_2$: 427.1877].

Example 32

(+)-5-[4-(1H-pyrazol-1-yl)benzyl]-2-(tetrahydro-2H-pyran-3-yl)-2,5-dihydro-3H-pyrazolo[4,3-c]cinnolin-3-one

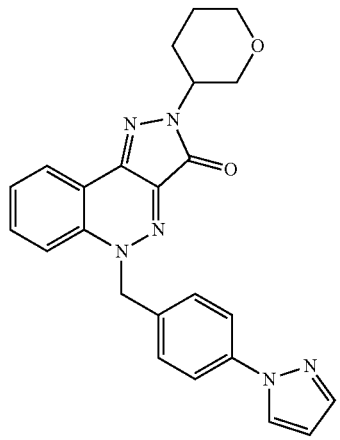 [SMILES: O=c1c2nn(Cc3ccc(-n4cccn4)cc3)c3ccccc3c-2nn1C1CCCOC1]

Example 33

(−)-5-[4-(1H-pyrazol-1-yl)benzyl]-2-(tetrahydro-2H-pyran-3-yl)-2,5-dihydro-3H-pyrazolo[4,3-c]cinnolin-3-one

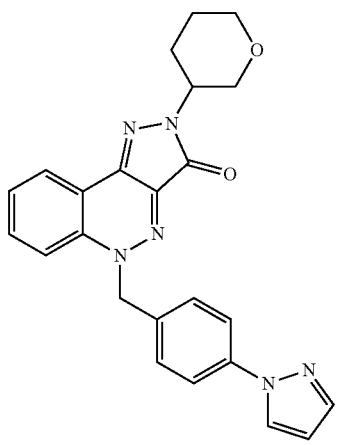 [SMILES: O=c1c2nn(Cc3ccc(-n4cccn4)cc3)c3ccccc3c-2nn1C1CCCOC1]

Example 31 was purified by preparative chiral HPLC (ChiralPak AS, 100% methanol), producing a first-eluting and a second-eluting enantiomer. The second eluting enantiomer rotated plane polarized light in a negative direction. Spectral data were identical to Example 31.

Example 34

2-(2,3-Dimethylphenyl)-5-[4-(1H-pyrazol-1-yl)benzyl]-2,5-dihydro-3H-pyrazolo[4,3-c]cinnolin-3-one

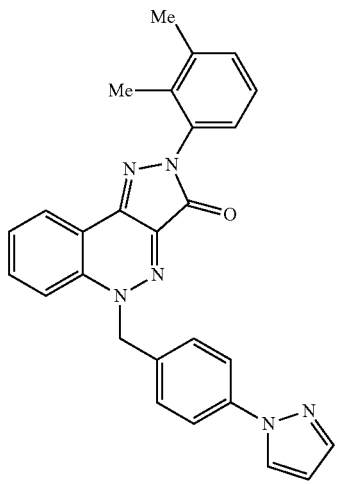 [SMILES: Cc1cccc(-n2nc3c4ccccc4n(Cc4ccc(-n5cccn5)cc4)nc-3c2=O)c1C]

Step 1: Preparation of 5-[4-(1H-pyrazol-1-yl)benzyl]-2,5-dihydro-3H-pyrazolo[4,3-c]cinnolin-3-one Ethyl 1-[4-(1H-pyrazol-1-yl)benzyl]-4-thioxo-1,4-dihydrocinnoline-3-carboxylate [(Example 31, Step 4) 449 mg, 1.15 mmol] was dissolved in ethanol (12.0 mL) and treated with hydrazine (0.61 mL, 19.57 mmol, 17 equiv). The mixture was stirred at 70° C. for 30 minutes then cooled to ambient temperature and concentrated in vacuo. The residue was suspended in ethyl acetate and filtered. The resulting solid was washed with dichloromethane and dried under in vacuo to afford the titled compound as a dark red powder.

Step 2: Preparation of 2-(2,3-dimethylphenyl)-5-[4-(1H-pyrazol-1-yl)benzyl]-2,5-dihydro-3H-pyrazolo[4,3-c]cinnolin-3-one 5-[4-(1H-Pyrazol-1-yl)benzyl]-2,5-dihydro-3H-pyrazolo[4,3-c]cinnolin-3-one (75 mg, 0.22 mmol) was dissolved in degassed N,N-dimethylformamide and treated with 1-iodo-2,3-dimethylbenzene (0.15 g, 0.66 mmol, 3 equiv), tribasic potassium phosphate (0.28 g, 1.31 mmol, 6 equiv), copper(I) iodide (42 mg, 0.22 mmol, 1 equiv) and (±)-trans-N,N'-dimethylcyclohexane-1,2-diamine (93 mg, 0.66 mmol, 3 equiv). The mixture was placed into an oil bath preheated at 110° C. for 30 minutes, cooled to ambient temperature, poured into sodium bicarbonate (25 mL, saturated aqueous) and extracted with ethyl acetate (3×50 mL). The combined organic extracts were dried with sodium sulfate, filtered and concentrated in vacuo. The residue was purified via silica gel gradient chromatography (60:40 to 0:100; hexanes:ethyl acetate), providing the titled compound. $^1$H-NMR (400 MHz, CDCl$_3$) δ 8.33-8.30 (1H, m), 7.90 (1H, d, J=2.6 Hz), 7.73-7.69 (3H, m), 7.58-7.52 (3H, m), 7.43 (2H, d, J=8.7 Hz), 7.31-7.27 (1H, m), 7.24-7.22 (2H, m), 6.47 (1H, dd, J=2.5, 1.8 Hz), 5.88 (2H, s), 2.37 (3H, s), 2.21 (3H, s) ppm; high resolution mass spectrometry (ES+) m/z 447.1931 [(M+H)$^+$; calculated for C$_{27}$H$_{22}$N$_6$O: 447.1928].

The following compounds of formula (II), wherein R$^3$ is absent, were prepared according to the general procedure described in Example 34, substituting the appropriate aryl halide for 1-iodo-2,3-dimethylbenzene. The starting materials are either commercially available, known in the literature or may be prepared from commercially available reagents using conventional reactions well known in the art.

| Ex. | R¹ (R³ is absent) | HRMS |
|---|---|---|
| 35 | 2-Me, 6-F pyridin-3-yl | $C_{25}H_{18}FN_7O$ [M + H] calc. 452.1630 obs. 452.1633 |
| 36 | 2-Cl, 3-Me pyridin-4-yl | $C_{25}H_{18}ClN_7O$ [M + H] calc. 468.1334 obs. 468.1326 |
| 37 | 2,3-difluoropyridin-4-yl | $C_{24}H_{15}F_2N_7O$ [M + H] calc. 456.1379 obs. 456.1371 |
| 38 | 2-cyanophenyl | $C_{26}H_{17}FN_7O$ [M + H] calc. 444.1567 obs. 444.1562 |
| 39 | 1-Me-pyrazol-4-yl | $C_{23}H_{18}N_8O$ [M + H] calc. 423.1676 obs. 423.1673 |
| 40 | 1-oxo-indan-7-yl | $C_{28}H_{20}N_6O_2$ [M + H] calc. 473.1721 obs. 473.1726 |

JOC, 68 (2003) p. 10195

| Ex. | R¹ (R³ is absent) | HRMS |
|---|---|---|
| 41 | 1-Me-imidazol-5-yl | $C_{23}H_{18}N_8O$ [M + H] calc. 423.1676 obs. 423.1671 |
| 42 | indan-4-yl | $C_{28}H_{23}N_6O$ [M + H] calc. 459.1928 obs. 459.1935 |
| 43 | 2-Me, 6-Cl pyridin-3-yl | $C_{25}H_{19}ClN_7O$ [M + H] calc. 468.1334 obs. 468.1350 |
| 44 | 5,6,7,8-tetrahydronaphthalen-1-yl | $C_{29}H_{25}N_6O$ [M + H] calc. 473.2084 obs. 473.2093 |

Example 45

(±)-5-(4-Iodobenzyl)-2-(tetrahydro-2H-pyran-3-O-2,5-dihydro-3H-pyrazolo[4,3-c]cinnolin-3-one

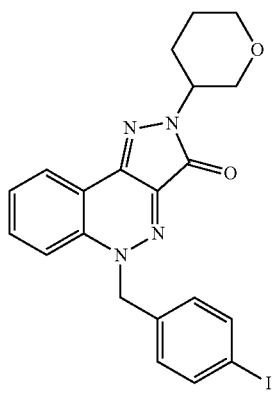 [SMILES: O=c1c2nn(Cc3ccc(I)cc3)c3ccccc3c-2nn1C1CCCOC1]

Using the procedures described in Example 31, substituting 1-(bromomethyl)-4-iodobenzene for 1-[4-(bromomethyl)phenyl]-1H-pyrazole (Step 3), the titled compound was obtained: $^1$H-NMR (400 MHz, CDCl$_3$) δ 8.28-8.24 (1H, m), 7.66 (2H, d, J=8.5 Hz), 7.56-7.51 (2H, m), 7.46-7.42 (1H, m), 7.02 (2H, d, J=8.5 Hz), 5.73 (2H, s), 4.74-4.65 (1H, m), 4.03 (1H, ddd, J=10.9, 4.6, 1.7 Hz), 3.98 (1H, d, J=11.1 Hz), 3.8 (1H, ap t, J=10.6 Hz), 3.53-3.46 (1H, m), 2.28-2.16 (1H, m), 2.14-2.07 (1H, m), 1.91-1.81 (2H, m) ppm. high resolution mass spectrometry (ES+) m/z 487.0626 [(M+H)$^+$; calculated for C$_{21}$H$_{19}$IN$_4$O$_2$: 487.0625].

Example 46

(±)-5-[4-(2-Methylpyridin-4-yl)benzyl]-2-(tetrahydro-2H-pyran-3-yl)-2,5-dihydro-3H-pyrazolo[4,3-c]cinnolin-3-one

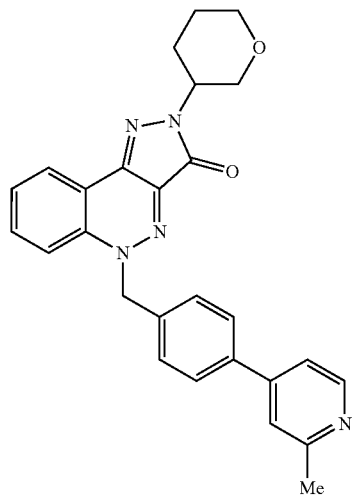 [SMILES: Cc1cc(-c2ccc(Cn3nc4c(=O)n(C5CCCOC5)nc-4c4ccccc43)cc2)ccn1]

5-(4-iodobenzyl)-2-(tetrahydro-2H-pyran-3-yl)-2,5-dihydro-3H-pyrazolo[4,3-c]cinnolin-3-one [(Example 45), 60 mg, 0.12 mmol] was dissolved in tetrahydrofuran (10 mL), treated with 2-methyl-4-(4,4,5,5-tetramethyl-1,3,2-dioxaborolan-2-yl) and cesium carbonate (0.31 mL, 1 M aqueous, 0.31 mmol, 2.6 equiv). The mixture was sparged under nitrogen, treated with bis(tri-tert-butylphosphine)palladium(0) (12 mg, 0.03 mmol, 0.2 equiv) and placed into an oil bath preheated at 65° C. After 1.5 hours, the mixture was cooled to ambient temperature, poured into water and extracted with ethyl acetate (3×60 mL). The combined organic extracts were dried with sodium sulfate, filtered and concentrated in vacuo. The residue was purified by preparative reverse phase HPLC (15:85 to 70:20; acetonitrile with 0.1% trifluoroacetic acid: water with 0.1% trifluoroacetic acid) to afford the titled compound: $^1$H-NMR (400 MHz, CDCl$_3$) δ 8.53 (1H, d, J=5.3 Hz), 8.30-8.27 (1H, m), 7.58 (2H, d, J=8.5 Hz), 7.56-7.51 (3H, m), 7.38 (2H, d, J=8.3 Hz), 7.31 (1H, s), 7.26-7.24 (1H, m), 5.86 (2H, s), 4.76-4.67 (1H, m), 4.04 (1H, ddd, J=10.7, 4.5, 1.7 Hz), 4.01-3.96 (1H, m), 3.81 (1H, ap t, J=10.6 Hz), 3.54-3.47 (1H, m), 2.60 (3H, s), 2.29-2.18 (1H, m), 2.16-2.09 (1H, m), 1.93-1.81 (2H, m) ppm; high resolution mass spectrometry (ES+) m/z 452.2076 [(M+H)$^+$; calculated for C$_{27}$H$_{25}$N$_5$O$_2$: 452.2081].

The following compounds of formula (V), wherein R$^3$ is absent, were prepared according to the general procedure described in Example 46, substituting the appropriate boronic acid or appropriately substituted boronic ester for 2-methyl-4-(4,4,5,5-tetramethyl-1,3,2-dioxaborolan-2-yl)pyridine. Palladium(II) acetate with X-PHOS or 1,1'-bis(diphenylphosphino)ferrocene and copper(I) chloride was used in place of bis(tri-tert-butylphosphine)palladium(0), and potassium carbonate for cesium carbonate. The starting materials are either commercially available, known in the literature or may be prepared from commercially available reagents using conventional reactions well known in the art.

(V)

| Ex. | R$^2$ (R$^3$ is absent) | HRMS |
|---|---|---|
| 47 | ![pyridine-Me] | C$_{27}$H$_{25}$N$_5$O$_2$ [M + H] calc. 452.2081 obs. 452.2077 |
| 48 | ![pyrazole-Me] | C$_{25}$H$_{24}$N$_6$O$_2$ [M + H] calc. 441.2034 obs. 441.2029 |

-continued (V)

| Ex. | R² (R³ is absent) | HRMS |
|---|---|---|
| 49 | 3-pyridyl | C₂₆H₂₃N₅O₂ [M + H] calc. 438.1925 obs. 438.1920 |
| 50 | 6-morpholino-pyridin-3-yl | C₃₀H₃₀N₆O₃ [M + H] calc. 523.2452 obs. 523.2441 |
| 51 | 5-methylpyridin-3-yl | C₂₇H₂₅N₅O₂ [M + H] calc. 452.2081 obs. 452.2080 |
| 52 | 5-methoxypyridin-3-yl | C₂₇H₂₆N₅O₃ [M + H] calc. 468.2030 obs. 468.2042 |
| 53 | 6-chloropyridin-3-yl | C₂₆H₂₃ClN₅O₂ [M + H] calc. 472.1540 obs. 472.1554 |
| 54 | 6-methoxypyridin-3-yl | C₂₇H₂₆N₅O₃ [M + H] calc. 468.2030 obs. 468.2043 |
| 55 | 2-pyridyl | C₂₆H₂₄N₅O₂ [M + H] calc. 438.1930 obs. 438.1934 |

Example 56

(±)-2-(Tetrahydro-2H-pyran-3-yl)-5-{[4-(1H-1,2,3-triazol-1-yl)phenyl]methyl}-2,5-dihydro-3H-pyrazolo[4,3-c]cinnolin-3-one (±)-5-(4-Iodobenzyl)-2-(tetrahydro-2H-pyran-3-yl)-2,5-dihydro-3H-pyrazolo[4,3-c]cinnolin-3-one [(Example 45), 25 mg, 0.051 mmol] was dissolved in degassed dimethylsulfoxide (1 mL) and water (0.2 mL), which was treated with copper (I) iodide (3.9 mg, 0.021 mmol, 0.4 equiv), 1,2,3-triazole (4.3 mg, 0.062 mmol, 1.2 equiv), (±)-trans-N,N'-dimethylcyclohexane-1,2-diamine (1.5 mg, 0.0010 mmol, 0.2 equiv) and potassium phosphate (27 mg, 0.15 mmol, 3 equiv). The vessel was sparged under nitrogen, sealed and placed into an oil bath preheated at 100° C. for 5 hours. The mixture was cooled to ambient temperature, poured into sodium bicarbonate (15 mL, aqueous saturated) and extracted with ethyl acetate (3×20 mL). The combined organic extracts were dried with sodium sulfate, filtered and concentrated in vacuo. The residue was purified by silica gel chromatography (100:0 to 90:10; dichloromethane:methanol), providing the titled compound as a red solid: ¹H-NMR (400 MHz, CDCl₃) δ 8.30-8.28 (1H, m), 7.96 (1H, d, J=0.9 Hz), 7.84 (1H, d, J=0.9 Hz), 7.76 (2H, m), 7.74 (2H, d, J=8.6 Hz), 7.58-7.55 (1H, m), 7.46 (2H, d, J=8.4 Hz), 5.87 (2H, s), 4.75-4.67 (1H, m), 4.04 (1H, dd, J=10.7, 1.4 Hz), 3.99 (1H, d, J=11.1 Hz), 3.82 (1H, ap t, J=10.7 Hz), 3.51 (1H, td, J=11.0, 3.3 Hz), 2.29-2.18 (2H, m), 2.12 (1H, br d, J=12.4 Hz), 1.94-1.83 (2H,

Example 57

(±)-2-(Tetrahydro-2H-pyran-3-yl)-5-{[4-(1H-1,2,3-triazol-2-yl)phenyl]methyl}-2,5-dihydro-3H-pyrazolo[4,3-c]cinnolin-3-one

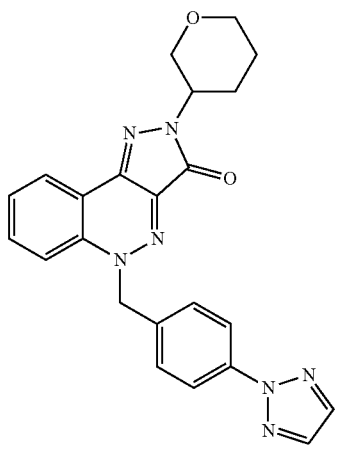 [SMILES: O=c1c2nn(Cc3ccc(-n4nccn4)cc3)c3ccccc3c-2nn1C1CCCOC1]

Using the procedures described in Example 56, the titled compound was also isolated as a deep red solid: $^1$H-NMR (400 MHz, CDCl$_3$) δ 8.28-8.26 (1H, m), 8.06 (2H, d, J=8.6 Hz), 7.79 (2H, s), 7.56-7.49 (3H, m), 7.40 (2H, d, J=8.6 Hz), 5.85 (2H, s), 4.75-4.67 (1H, m), 4.04 (1H, dd, J=10.5, 3.9 Hz), 3.99 (1H, d, J=11.0 Hz), 3.81 (1H, ap t, J=10.7 Hz), 3.50 (1H, td, J=11.4, 3.4 Hz), 2.23 (1H, ddd, J=17.3, 12.2, 5.5 Hz), 2.12 (1H, br d, J=11.8 Hz), 1.95-1.82 (2H, m) ppm; high resolution mass spectrometry (ES+) m/z 428.1838 [(M+H)$^+$; calculated for C$_{23}$H$_{22}$N$_7$O$_2$: 428.1829].

Example 58

(±)-2-(Oxiran-2-ylmethyl)-5-[4-(1H-pyrazol-1-yl)benzyl]-2,5-dihydro-3H-pyrazolo[4,3-c]cinnolin-3-one

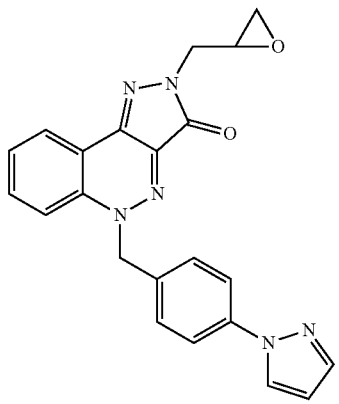 [SMILES: O=c1c2nn(Cc3ccc(-n4cccn4)cc3)c3ccccc3c-2nn1CC1CO1]

A solution of 3-chlorobenzenecarboperoxoic acid (29 mg, 0.17 mmol, 1.3 equiv) in dichloromethane (3 mL) was cooled to 0° C. and treated with a dichloromethane (1 mL) solution of 2-allyl-5-[4-(1H-pyrazol-1-yl)benzyl]-2,5-dihydro-3H-pyrazolo[4,3-c]cinnolin-3-one [(Example 10), 50 mg, 0.13 mmol]. After stirring for 1 hour at 0° C., the mixture was warmed to ambient temperature and stirred for an additional 14 hours. The mixture was treated with additional 3-chlorobenzenecarboperoxoic acid (50.0 mg, 0.29 mmol, 2.2 equiv) and after three hours, the mixture was cooled to 0° C., treated with sodium bicarbonate (3 mL, saturated aqueous), diluted with brine (10 mL) and extracted with dichloromethane (3×30 mL). The combined organic extracts were dried with sodium sulfate, filtered and concentrated in vacuo. The residue was purified via silica gel gradient chromatography (0:100 to 100:0; hexanes:ethyl acetate), providing the titled compound as a dark red solid: $^1$H-NMR (400 MHz, CDCl$_3$) δ 8.31-8.28 (1H, m), 7.89 (1H, d, J=2.5 Hz), 7.71 (1H, d, J=1.4 Hz), 7.68 (2H, d, J=8.7 Hz), 7.57-7.51 (3H, m), 7.38 (2H, d, J=8.7 Hz), 6.46 (1H, dd, J=2.4, 1.8 Hz), 5.85 (2H, s), 4.32 (1H, dd, J=14.5, 4.5 Hz), 4.22 (1H, dd, J=14.5, 5.5 Hz), 3.43-3.38 (1H, m), 2.88 (1H, dd, J=4.7, 4.1 Hz), 2.79 (1H, dd, J=4.8, 2.6 Hz) ppm. high resolution mass spectrometry (ES+) m/z 399.1563 [(M+H)$^+$; calculated for C$_{22}$H$_{18}$N$_6$O$_2$: 399.1564].

Example 59

(±)-2-(2,3-dimethoxypropyl)-5-[4-(1H-pyrazol-1-yl)benzyl]-2,5-dihydro-3H-pyrazolo[4,3-c]cinnolin-3-one

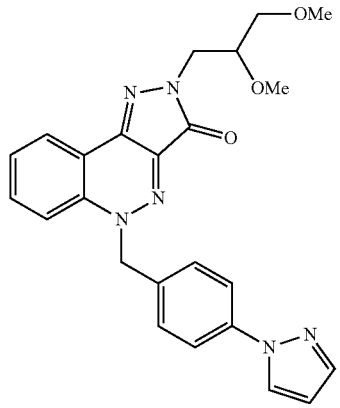 [SMILES: COCC(Cn1nc2c3ccccc3n(Cc3ccc(-n4cccn4)cc3)nc-2c1=O)OC]

(±)-2-(2,3-Dihydroxypropyl)-5-[4-(1H-pyrazol-1-yl)benzyl]-2,5-dihydro-3H-pyrazolo[4,3-c]cinnolin-3-one [(Example 11), 0.10 g, 0.24 mmol] was dissolved in degassed N,N-dimethylformamide (5 mL), cooled to 0° C. and sparged under nitrogen. The mixture was treated with sodium hydride (21 mg, 0.53 mmol, 2.2 equiv) and after minutes, treated with iodomethane (37 µL, 0.60 mmol, 2.5 equiv). After stirring for 1 hour, the mixture was treated with methanol (2 mL), poured into water (25 mL) and extracted with ethyl acetate (3×50 mL). The combined organic extracts were dried with sodium sulfate, filtered and concentrated in vacuo. The residue was purified via silica gel gradient chromatography (100:0 to 0:100; hexanes:ethyl acetate containing 10% methanol), providing the titled compound: $^1$H-NMR (400 MHz, CDCl$_3$) δ 8.29-8.26 (1H, m), 7.89 (1H, d, J=2.5 Hz), 7.71 (1H, d, J=1.7 Hz), 7.68 (2H, d, J=8.6 Hz), 7.56-7.51 (3H, m), 7.39 (2H, d, J=8.6 Hz), 6.46 (1H, dd, J=2.4, 1.9 Hz), 5.83 (2H, s), 4.21 (2H, d, J=5.8 Hz), 3.92-3.86 (1H, m), 3.64 (1H, dd, J=10.4, 3.7 Hz), 3.55 (1H, dd, J=10.4, 6.0 Hz), 3.52 (3H, s), 3.42 (3H, s) ppm; high resolution mass spectrometry (ES+) m/z 445.1976 [(M+H)⁺; calculated for $C_{24}H_{24}N_6O_3$: 445.1983].

Example 60

6-Chloro-2-(2-methylphenyl)-5-[4-(1H-pyrazol-1-yl) benzyl]-2,5-dihydro-3H-pyrazolo[4,3-c]cinnolin-3-one

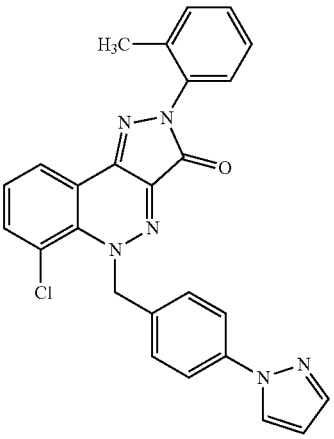 [SMILES: Cc1ccccc1-n1nc2c3cccc(Cl)c3n(Cc3ccc(-n4cccn4)cc3)nc-2c1=O]

Step 1: Preparation of ethyl 3-(3-chloro-2-fluorophenyl)-2-diazo-3-oxopropanoate Ethyl 3-(3-chloro-2-fluorophenyl)-3-oxopropanoate (1.30 g, 5.31 mmol), triethylamine (0.618 g, 6.11 mmol, 1.15 equiv), and 4-acetamidobenzenesulfonyl azide (1.40 g, 5.85 mmol, 1.1 equiv) were combined in acetonitrile (15 mL). After stirred at ambient temperature for 30 minutes, the mixture was concentrated in vacuo and the residue was treated with sodium hydroxide (25 mL, 2 M aqueous) and extracted with twice chloroform. The combined organic extracts were washed once with brine, dried with sodium sulfate, filtered and concentrated in vacuo. The residue was purified by silica gel gradient chromatography (100:0 to 40:60; hexanes:ethyl acetate), providing the titled compound.

Step 2: Preparation of ethyl-3-(3-chloro-2-fluorophenyl)-2-hydrazinylidene-3-oxopropanoate To a solution of ethyl 3-(3-chloro-2-fluorophenyl)-2-diazo-3-oxopropanoate (1.28 g, 4.73 mmol) in dioxane (12 mL) was added tri-n-butylphosphine (1.23 mL, 4.97 mmol). After stirring for 10 minutes at ambient temperature, the mixture was concentrated in vacuo and the residue was purified by silica gel gradient chromatography (100:0 to 40:60 hexane:ethyl acetate), providing the titled compound.

Step 3: Preparation of ethyl-8-chloro-4-oxo-1-[4-(1H-pyrazol-1-yl)benzyl-1,4-dihydrocinnoline-3-carboxylate Ethyl-3-(3-chloro-2-fluorophenyl)-2-hydrazinylidene-3-oxopropanoate (796 mg, 2.92 mmol) and 1-[4-(bromomethyl)phenyl]-1H-pyrazole (900 mg, 3.80 mmol, 1.3 equiv) were dissolved in degassed N,N-dimethylformamide (10 mL), cooled to 0° C. and treated with sodium hydride (187 mg, 4.67 mmol, 1.6 equiv). The mixture was stirred at 0° C. for 2 hours, treated with ammonium chloride (10 mL, 25% aqueous), warmed to ambient temperature, diluted with water, and extracted with ethyl acetate (3×50 mL). The combined organic extracts were dried with sodium sulfate, filtered, and concentrated in vacuo. The residue was purified by silica gel gradient chromatography (100:0 to 0:100, hexanes: ethyl acetate), providing the titled compound.

Step 4: Preparation of ethyl-8-chloro-1-[4-(1H-pyrazol-1-yl)benzyl]-4-thioxo-1,4-dihydrocinnoline-3-carboxylate Ethyl-8-chloro-4-oxo-1-[4-(1H-pyrazol-1-yl)benzyl-1,4-dihydrocinnoline-3-carboxylate (627 mg, 1.53 mmol) was dissolved in toluene (7 mL), treated with Lawesson's Reagent (434 mg, 1.074 mmol, 0.7 equiv) and placed into an oil bath preheated at 105° C. for 5 minutes. The mixture was cooled to ambient temperature, concentrated in vacuo and the residue was purified by silica gel gradient chromatography (100:0 to 60:40; hexanes:ethyl acetate), providing the titled compound.

Step 5: Preparation of 6-chloro-2-(2-methylphenyl)-5-[4-(1H-pyrazol-1-yl)benzyl]-2,5-dihydro-3H-pyrazolo[4,3-c]cinnolin-3-one Ethyl-8-chloro-1-[4-(1H-pyrazol-1-yl)benzyl]-4-thioxo-1,4-dihydrocinnoline-3-carboxylate (48 mg, 0.113 mmol), potassium carbonate (78 mg, 0.56 mmol, 5 equiv), and 2-methylphenyl hydrazine (23 mg, 0.19 mmol, 1.7 equiv) were combined in 1,2-dimethoxyethane (2 mL) and heated to 92° C. for 2 hours. The mixture was cooled to ambient temperature, diluted with water (20 mL) and extracted with ethyl acetate (3×40 mL). The combined organic extracts were dried with sodium sulfate, filtered and concentrated in vacuo. The residue was purified by silica gel chromatography (100:0 to 94:6; chloroform:methanol), providing the titled compound: ¹H-NMR (400 MHz, CDCl₃) δ 8.24 (1H, d, J=7.2 Hz), 7.88 (1H, s), 7.71-7.61 (4H, m), 7.47-7.42 (3H, m), 7.37-7.30 (3H, m), 7.29 (1H, s), 6.4 (1H, m), 6.34 (2H, s), 2.36 (3H, s), ppm; high resolution mass spectrometry (ES+) m/z 467.1388 [(M+H)⁺; calculated for $C_{26}H_{20}ClN_6O$: 467.1382].

The following compound was prepared according to the general procedure described in Example 60, substituting 2-hydrazinylcyclohexanol for 2-methylphenyl hydrazine. The starting materials are either commercially available, known in the literature or may be prepared from commercially available reagents using conventional reactions known in the art.

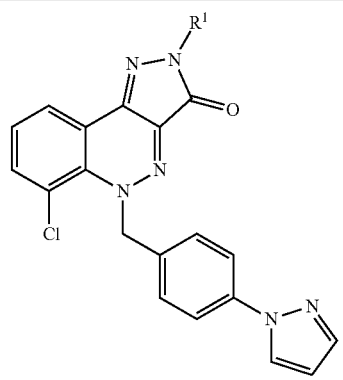

| Ex. | R¹ | HRMS/LRMS |
|---|---|---|
| 61 | HO⟋⟍ (cyclohexyl) | $C_{25}H_{24}ClN_6O_2$ [M + H] calc. 475.1644 obs. 475.1661 |

Example 62

6-Chloro-2-(trans-3-hydroxytetrahydro-2H-pyran-4-yl)-5-[4-(1H-pyrazol-1-yl)benzyl]-2,5-dihydro-3H-pyrazolo[4,3-c]cinnolin-3-one

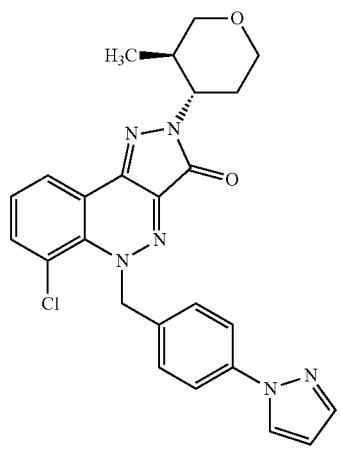 [SMILES: C[C@H]1COCC[C@@H]1n1nc2c3cccc(Cl)c3n(Cc3ccc(-n4cccn4)cc3)nc-2c1=O]

Step 1: Preparation of (±)-trans-3-hydrazinotetrahydro-2H-pyran-4-ol and (±)-trans-4-hydrazinotetrahydro-2H-pyran-3-ol (±)-3,7-Dioxabicyclo[4.1.0]heptane [(*Bioorg. Med. Chem. Lett.* 2006, 16, 4311), 1.25 g, 12.5 mmol] was dissolved in absolute ethanol (10 mL), treated with hydrazine (1.96 mL, 62.4 mmol, 5 equiv) was placed into an oil bath preheated at 70° C. for 3 hours. The mixture was cooled to ambient temperature and concentrated in vacuo to provide the titled mixture (~3:1) of compounds.

Step 2: Preparation of 6-chloro-2-(trans-3-hydroxytetrahydro-2H-pyran-4-yl)-5-[4-(1H-pyrazol-1-yl)benzyl]-2,5-dihydro-3H-pyrazolo[4,3-c]cinnolin-3-one Ethyl-8-chloro-1-[4-(1H-pyrazol-1-yl)benzyl]-4-thioxo-1,4-dihydrocinnoline-3-carboxylate [(Example 60, Step 4) 188 mg, 0.442 mmol] was dissolved in 1,2-dimethoxyethane (1.5 mL) and treated with a mixture of (±)-trans-3-hydrazinotetrahydro-2H-pyran-4-ol and (±)-trans-4-hydrazinotetrahydro-2H-pyran-3-ol (117 mg, 0.885 mmol, 2 equiv) and potassium carbonate (183 mg, 1.327 mmol, 3 equiv). The mixture was placed into an oil bath preheated to 90° C. for 35 minutes, cooled to ambient temperature, diluted with water and extracted with ethyl acetate (3×50 mL). The combined organic extracts were washed once with brine, dried with sodium sulfate; filtered and concentrated in vacuo. The residue was purified by silica gel gradient chromatography (100:0 to 0:100; hexanes:ethyl acetate), providing an inseparable mixture of regioisomers, which was further purified by chiral HPLC (Chiralcel OJ Column, 100% methanol) to produce a first-, second-, and third-eluting peak. The first-eluting peak was determined to the titled compound (enantiopure, relative trans stereochemical configuration), of which the absolute stereochemistry is unknown: ¹H-NMR (400 MHz, CDCl₃) δ 8.22 (1H, d, J=8.1 Hz), 7.87 (1H, s), 7.71-7.59 (4H, m), 7.46 (1H, t, J=8.1 Hz), 7.29-7.20 (2H, m), 6.44 (1H, s), 6.33 (2H, s), 4.52-4.43 (1H, m), 4.26-4.17 (2H, m), 4.11-4.04 (1H, m), 3.55 (1H, t, J=12.0 Hz), 3.32 (1H, t, J=10.3 Hz), 2.32-2.19 (1H, m), 2.14-2.06 (1H, br d J=12.4 Hz). ppm; low resolution mass spectrometry (ES+) m/z 477.3 [(M+H)⁺; calculated for $C_{24}H_{22}ClN_6O_3$: 477.5].

Example 63

6-Chloro-2-(trans-3-hydroxytetrahydro-2H-pyran-4-yl)-5-[4-(1H-pyrazol-1-yl)benzyl]-2,5-dihydro-3H-pyrazolo[4,3-c]cinnolin-3-one

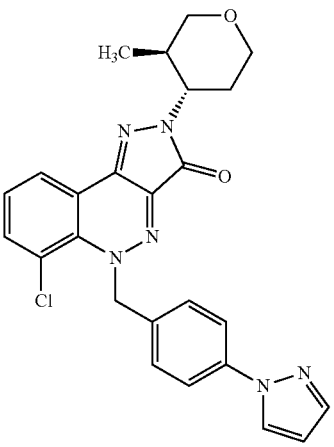 [SMILES: C[C@H]1COCC[C@@H]1n1nc2c3cccc(Cl)c3n(Cc3ccc(-n4cccn4)cc3)nc-2c1=O]

The titled compound was prepared according to the procedures described in Example 62. The second-eluting peak (Step 2) was further purified by chiral HPLC (Chiralcel AS Column, 100% methanol) providing a first-eluting and a second-eluting peak. The first-eluting peak was determined to the titled compound, enantiomer of Example 62, of which the spectral data were identical to Example 62.

Example 64

6-Chloro-2-(cis-3-hydroxytetrahydro-2H-pyran-4-yl)-5-[4-(1H-pyrazol-1-yl)benzyl]-2,5-dihydro-3H-pyrazolo[4,3-c]cinnolin-3-one

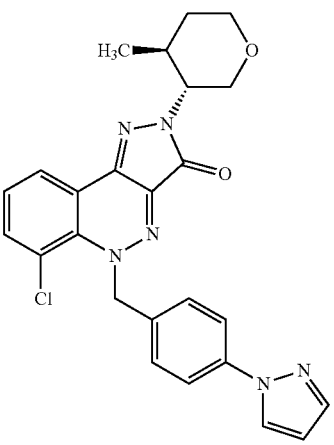 [SMILES: C[C@H]1CCOC[C@@H]1n1nc2c3cccc(Cl)c3n(Cc3ccc(-n4cccn4)cc3)nc-2c1=O]

The titled compound was prepared using the procedures described in Example 63. The second-eluting peak (enantiopure, relative cis stereochemical configuration), of which the absolute stereochemistry is unknown: $^1$H-NMR (400 MHz, CDCl$_3$) δ 8.19 (1H, d, J=7.7 Hz), 7.87 (1H, s), 7.71-7.59 (5H, m), 7.44 (1H, t, J=6.8 Hz), 7.22 (2H, d, J=7.8 Hz), 6.44 (1H, s), 6.33 (2H, s), 4.46-4.33 (2H, m), 4.20 (1H, d, J=11.0 Hz), 4.08 (1H, d, J=11.0 Hz), 3.65 (1H, t, J=11.0 Hz), 3.55 (1H, t, J=12.4 Hz), 2.18 (1H, br d, J=12.7 Hz), 1.92-1.80 (1H, m) ppm; low resolution mass spectrometry (ES+) m/z 477.3 [(M+H)$^+$; calculated for C$_{24}$H$_{22}$ClN$_6$O$_3$: 477.5].

Example 65

6-Chloro-2-(cis-3-hydroxytetrahydro-2H-pyran-4-yl)-5-[4-(1H-pyrazol-1-yl)benzyl]-2,5-dihydro-3H-pyrazolo[4,3-c]cinnolin-3-one

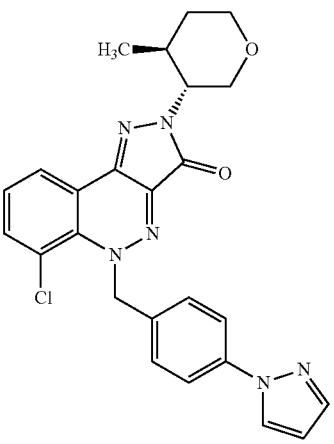 [SMILES: C[C@H]1CCOC[C@@H]1n1nc2c3cccc(Cl)c3n(Cc3ccc(-n4cccn4)cc3)nc-2c1=O]

The titled compound was prepared using the procedures described in Example 53. The third-eluting peak was determined to the titled compound, enantiomer of Example 64, of which the spectral data were identical to Example 64.

Example 66

(±)-6-Chloro-5-(4-iodobenzyl)-2-tetrahydro-2H-pyran-3-yl)-2,5-dihydro-3H-pyrazolo[4,3-c]cinnolin-3-one

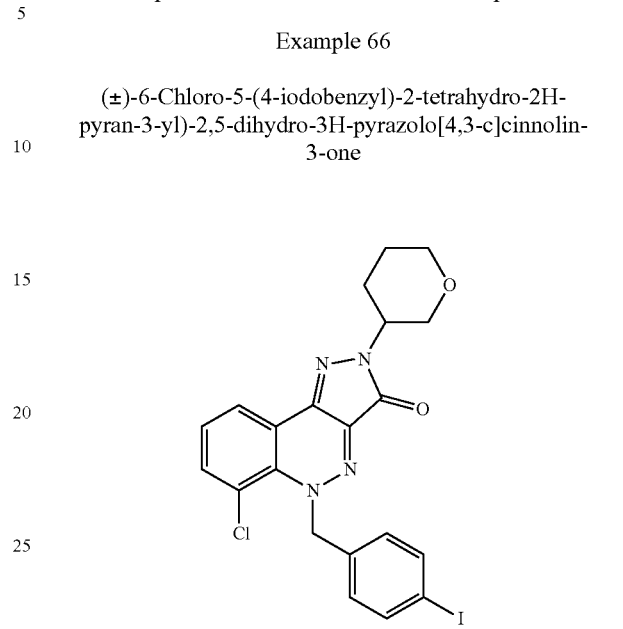

Step 1: Preparation of ethyl-8-chloro-1-(4-iodobenzyl)-4-oxo-1,4-dihydrocinnoline-3-carboxylate Ethyl-3-(3-chloro-2-fluorophenyl)-2-hydrazinylidene-3-oxopropanoate [(Example 60, Step 2) 1.61 g, 5.90 mmol] and 4-iodobenzyl bromide (2.28 g, 7.68 mmol, 1.3 equiv) were dissolved in degassed N,N-dimethylformamide (20 mL), cooled to 0° C. and treated with sodium hydride (378 mg, 9.45 mmol, 1.6 equiv). After stirring for 2 hours at 0° C., the mixture was treated with ammonium chloride (25 mL, 25% aqueous), warmed to ambient temperature, diluted with water (100 mL) and extracted with ethyl acetate (3×50 mL). The combined organic extracts were washed once with water and brine, dried with sodium sulfate, filtered and concentrated in vacuo. The residue was purified by silica gel gradient chromatography (100:0 to 20:80; hexanes:ethyl acetate), providing the titled compound.

Step 2: Preparation of ethyl-8-chloro-1-(4-iodobenzyl)-4-thioxo-1,4-dihydrocinnoline-3-carboxylate Ethyl-8-chloro-1-(4-iodobenzyl)-4-oxo-1,4-dihydrocinnoline-3-carboxylate (736 mg, 1.57 mmol) and Lawesson's Reagent (445 mg, 1.10 mmol, 0.7 equiv) were combined in toluene (8 mL) and placed into an oil bath preheated at 105° C. for 15 minutes. The mixture was cooled to ambient temperature, concentrated in vacuo and the residue was purified by silica gel gradient chromatography (100:0 to 40:60; hexanes:ethyl acetate), providing the titled compound.

Step 3: Preparation of 6-Chloro-5-(4-iodobenzyl)-2-tetrahydro-2H-pyran-3-yl)-2,5-dihydro-3H-pyrazolo [4,3-c]cinnolin-3-one Ethyl-8-chloro-1-(4-iodobenzyl)-4-thioxo-1,4-dihydrocinnoline-3-carboxylate (230 mg, 0.474 mmol) was dissolved in N,N-dimethylformamide (1 mL) and 1,2- dimethoxyethane (5 mL) and treated with potassium carbonate (656 mg, 4.74 mmol, 10 equiv), (±)-tetrahydro-2H-pyran-3-ylhydrazine hydrochloride [(Example 31, Step 6), 145 mg, 0.949 mmol, 2 equiv] and mercury(II) chloride (129 mg, 0.474 mmol, 1 equiv). The mixture was placed into an oil bath preheated at 70° C. for 4 hours, cooled to ambient temperature, poured into water and extracted with ethyl acetate (2×50 mL). The combined organic extracts were washed once with water and brine, dried with sodium sulfate, filtered and concentrated in vacuo. The residue was purified by silica gel gradient chromatography (100:0 to 96:4; chloroform:methanol) to give the titled compound: $^1$H-NMR (400 MHz, CDCl$_3$) δ 8.19 (1H, s), 7.66-7.56 (4H, m), 7.43 (1H, t, J=7.4 Hz), 6.87 (2H, d, J=9.5 Hz), 6.20 (2H, s), 4.71-4.61 (1H, m), 4.05-3.94 (1H, t, J=11.7 Hz), 3.80-3.73 (1H, t, J=11.7 Hz), 3.52-3.44 (1H, m), 2.24-2.03 (2H, m), 1.90-1.80 (2H, m) ppm; high resolution mass spectrometry (ES+) m/z 521.0254 [(M+H)$^+$; calculated for C$_{21}$H$_{19}$ClN$_4$O$_2$: 521.0236].

were washed three times with water and once with brine, dried with sodium sulfate, filtered and concentrated in vacuo. The residue was purified by silica gel gradient chromatography (100:0 to 95:5; chloroform:methanol), providing the titled compound: $^1$H-NMR (400 MHz, CDCl$_3$) δ 8.66 (1H, s), 8.21 (1H, d, J=6.3 Hz), 7.70 (1H, d, J=9.5 Hz), 7.64 (1H, d, J=9.5 Hz), 7.49-7.40 (4H, m), 7.24-7.18 (2H, m), 6.32 (2H, s), 4.70-4.62 (1H, m), 4.05-3.95 (1H, m), 3.78 (1H, t, J=10.1 Hz), 3.53-3.45 (1H, m), 2.58 (3H, s), 2.25-2.06 (1H, m), 1.90-1.80 (2H, m), 1.62-1.52 (2H, m) ppm; low resolution mass spectrometry (ES+) m/z 486.4 [(M+H)$^+$; calculated for C$_{27}$H$_{25}$ClN$_5$O$_2$: 486.2].

Example 67

(±)-6-Chloro-5-{[4-(6-methylpyridin-3-yl)phenyl]methyl}-2-(tetrahydro-2H-pyran-3-yl)-2,5-dihydro-3H-pyrazolo[4,3-c]cinnolin-3-one Example 68

(±)-6-Chloro-2-(trans-2-hydroxycyclohexyl)-5-{[4-(6-methylpyridin-3-yl)phenyl]methyl}-2-(tetrahydro-2H-pyran-3-yl)-2,5-dihydro-3H-pyrazolo[4,3-c]cinnolin-3-one

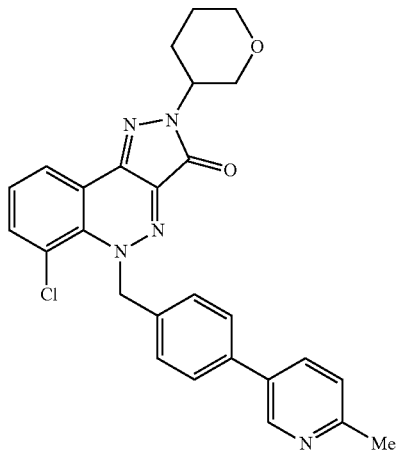 [SMILES: Cc1ccc(-c2ccc(Cn3nc4c(=O)n(C5CCCOC5)nc-4c4cccc(Cl)c43)cc2)cn1]

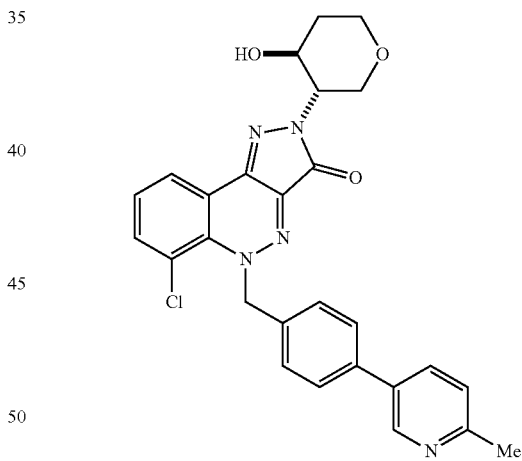

(±)-6-Chloro-5-(4-iodobenzyl)-2-tetrahydro-2H-pyran-3-yl)-2,5-dihydro-3H-pyrazolo[4,3-c]cinnolin-3-one [(Example 66), 39 mg, 0.075 mmol] was combined with (6-methylpyridin-3-yl)boronic acid (29 mg, 0.19 mmol, 2.5 equiv), copper(I) chloride (7.4 mg, 0.075 mmol, 1 equiv), cesium carbonate (49 mg, 0.15 mmol, 2 equiv), palladium(II) acetate (1.7 mg, 0.0075 mmol, 0.1 equiv), and bis(diphenylphosphino)ferrocene (4.2 mg, 0.0075 mmol, 0.1 equiv) in degassed N,N-dimethylformamide (1 mL). The mixture was placed into an oil bath preheated at 80° C. for 15 minutes, cooled to ambient temperature, diluted with water (5 mL) and extracted with ethyl acetate (3×30 mL). The combined organic extracts Using the procedures described in Example 67, substituting (±)-2-hydrazinylcyclohexanol for (±)-tetrahydro-2H-pyran-3-ylhydrazine hydrochloride (Example 66, Step 3), the titled compound was obtained: $^1$H-NMR (400 MHz, CDCl$_3$) δ 8.67 (1H, s), 8.22 (1H, d, J=8.0 hz), 7.71 (1H, d, J=8.0 Hz), 7.64 (1H, d, J=8.0 Hz), 7.49-7.40 (3H, m), 7.28-7.16 (3H, m), 6.34 (2H, s), 4.34-4.27 (1H, m), 4.16-4.04 (2H, m), 2.58 (3H, s), 2.26-2.02 (2H, m), 1.92-1.80 (2H, m), 1.65-1.56 (2H, m), 1.52-1.40 (2H, m) ppm; high resolution mass spectrometry (ES+) m/z 500.1855 [(M+H)+; calculated for $C_{28}H_{26}ClN_5O_2$: 500.1848].

Example 69

(±)-6-Chloro-2-(trans-2-hydroxycyclohexyl)-5[(6'-methyl-2,3'-bipyridin-5-yl)methyl]-2,5-dihydro-3H-pyrazolo[4,3-c]cinnolin-3-one

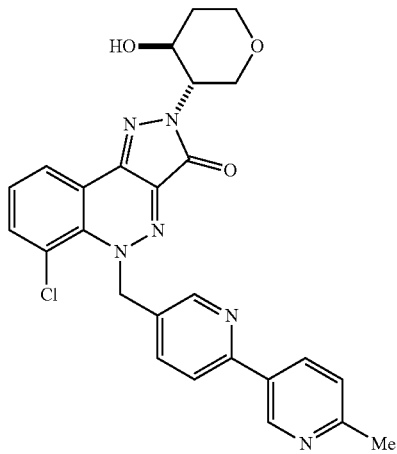

Step 1: Preparation of ethyl 1-[(6-bromopyridin-3-yl)methyl]-8-chloro-4-oxo-1,4-dihydrocinnoline-3-carboxylate Ethyl-3-(3-chloro-2-fluorophenyl)-2-hydrazinylidene-3-oxopropanoate [(Example 60, Step 1), 1.9 g, 7.0 mmol] and (6-bromopyridin-3-yl)methyl methanesulfonate (2.4 g, 9.1 mmol, 1.3 equiv) were dissolved in degassed N,N'-dimethyl formamide, cooled to 0° C. and treated with sodium hydride (0.45 g, 11 mmol, 1.6 equiv). After stirring at 0° C. for 3 hours, additional (6-bromopyridin-3-yl)methyl methanesulfonate (0.55 g, 2.1 mmol, 0.3 equiv) and sodium hydride (84 mg, 2.1 mmol, 0.3 equiv) were added and stirred for an additional 5 hours. The mixture was treated with ammonium chloride (10 mL, aqueous saturated), poured into water (50 mL) and extracted three times with ethyl acetate. The combined organic extracts were washed once with water and brine, dried with sodium sulfate, filtered and concentrated in vacuo. The residue was purified by silica gel gradient chromatography (100:0 to 96:4; chloroform:methanol), providing the titled compound.

Step 2: Preparation of ethyl 8-chloro-1-[(6'-methyl-2,3'-bipyridin-5-yl)methyl]-4-oxo-1,4-dihydrocinnoline-3-carboxylate Ethyl 1-[(6-bromopyridin-3-yl)methyl]-8-chloro-4-oxo-1,4-dihydrocinnoline-3-carboxylate (0.21 g, 0.49 mmol) was combined with (6-methylpyridin-3-yl)boronic acid (0.19 g, 1.2 mmol, 2.5 equiv), copper(I) chloride (48 mg, 0.49 mmol, 1 equiv), cesium carbonate (0.32 g, 0.97 mmol, 2 equiv), palladium(II) acetate (11 mg, 0.049 mmol, 0.1 equiv), and bis(diphenylphosphino)ferrocene (27 mg, 0.049 mmol, 0.1 equiv) in degassed N,N-dimethylformamide (3 mL). The mixture was placed into an oil bath preheated at 95° C. for 15 minutes, cooled to ambient temperature, diluted with water (5 mL) and extracted with ethyl acetate (3×30 mL). The combined organic extracts were washed once with water and brine, dried with sodium sulfate, filtered and concentrated in vacuo, providing the titled compound.

Step 3: Preparation of (±)-6-Chloro-2-(trans-2-hydroxycyclohexyl)-5[(6'-methyl-2,3'-bipyridin-5-yl)methyl]-2,5-dihydro-3H-pyrazolo[4,3-c]cinnolin-3-one Ethyl 8-chloro-1-[(6'-methyl-2,3'-bipyridin-5-yl)methyl]-4-thioxo-1,4-dihydrocinnoline-3-carboxylate (26 mg, 0.0058 mmol), (±)-2-hydrazinylcyclohexanol (19 mg, 0.14 mmol, 2.5 equiv) and potassium carbonate (24 mg, 0.17 mmol, 3 equiv) were combined in dimethoxyethane (1 mL) and placed into an oil bath preheated to 90° C. for 90 minutes. The mixture was cooled to ambient temperature, diluted with ethyl acetate and washed once with water and brine. The organic layer was dried sodium sulfate, filtered and concentrated in vacuo. The residue was purified by silica gel gradient chromatography (100:0 to 90:10; chloroform:methanol), providing the titled compound as a deep red solid: $^1$H-NMR (400 MHz, CDCl$_3$) δ 9.02 (1H, br s), 8.56 (1H, s), 8.21 (1H, d, J=9.1 Hz), 8.16 (1H, d, J=10.9 Hz), 7.65 (2H, d, J=7.5 Hz), 7.56 (1H, d, J=9.2 Hz), 7.43 (2H, t, J=7.5 Hz), 7.27-7.21 (1H, m), 6.33 (2H, s), 4.34-4.25 (1H, m), 4.11-4.02 (1H, m), 2.6 (3H, s), 2.26-2.17 (1H, m), 2.07-2.00 (1H, m), 1.92-1.79 (2H, m), 1.68-1.56 (2H, m), 1.52-1.39 (2H, m) ppm; high resolution mass spectrometry (ES+) m/z 501.1812 [(M+H)+; calculated for $C_{27}H_{25}ClN_6O_2$: 501.1800].

Example 70

(±)-6-Chloro-2-(trans-2-hydroxycyclohexyl)-5[(6-methylpyridin-3-yl)methyl]-2,5-dihydro-3H-pyrazolo[4,3-c]cinnolin-3-one

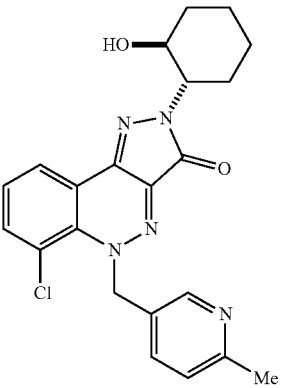

Step 1: Preparation of ethyl 8-chloro-1-[(6-methylpyridin-3-yl)methyl]-4-oxo-1,4-dihydrocinnoline-3-carboxylate Ethyl 1-[(6-bromopyridin-3-yl)methyl]-8-chloro-4-oxo-1,4-dihydrocinnoline-3-carboxylate [(Example 69, Step 1), 0.11 g, 0.25 mmol] was dissolved in tetrahydrofuran (1.5 mL), sparged under nitrogen and treated with methylzinc chloride (0.18 mL, 2.0 M tetrahydrofuran solution, 0.35 mmol, 1.4 equiv) and 1,1'bis(diphenylphosphino)ferrocene-palladium(II)dichloride dichloromethane complex (10 mg, 0.013 mmol, 0.05 equiv). After stirring for 15 minutes, tetrakis(triphenylphosphine)palladium(0) (58 mg, 0.050 mmol, 0.2 equiv) were added and the mixture was stirred at ambient temperature for an additional 2 hours. The mixture was poured into water, extracted twice with ethyl acetate and the combined organic extracts were dried with sodium sulfate, filtered and concentrated in vacuo. The residue was purified by silica gel gradient chromatography (100:0 to 0:100; hexanes:ethyl acetate), providing the titled compound.

Step 1: Preparation of (±)-6-Chloro-2-(trans-2-hydroxycyclohexyl)-5-[(6-methylpyridin-3-yl)methyl]-2,5-dihydro-3H-pyrazolo[4,3-c]cinnolin-3-one Using the procedures described in Example 69, substituting ethyl 8-chloro-1-[(6-methylpyridin-3-yl)methyl]-4-oxo-1,4-dihydrocinnoline-3-carboxylate for ethyl 8-chloro-1-[(6'-methyl-2,3'-bipyridin-5-yl)methyl]-4-thioxo-1,4-dihydrocinnoline-3-carboxylate, the titled compound was obtained: $^1$H-NMR (400 MHz, CDCl$_3$) δ 8.39 (1H, s), 8.20 (1H, d, J=8.2 Hz), 7.64 (1H, d, J=6.9 Hz), 7.43 (1H, t, J=8.2 Hz), 7.36 (1H, d, J=8.2 Hz), 7.08 (1H, d, J=8.8 Hz), 6.26 (2H, s), 4.34-4.24 (1H, m), 4.11-4.03 (1H, m), 2.51 (3H, s), 2.24-2.17 (1H, m), 2.09-2.00 (1H, m), 1.88-1.79 (2H, m), 1.66-1.52 (3H, m), 1.49-1.41 (1H, m) ppm; low resolution mass spectrometry (ES+) m/z 424.3 [(M+H)$^+$; calculated for C$_{22}$H$_{23}$ClN$_5$O$_2$: 424.1].

Example 71

(±)-2-[cis,trans-4-methyltetrahydro-2H-pyran-3-yl]-5-[4-(1H-pyrazol-1-yl)benzyl]-2,5-dihydro-3H-pyrazolo[4,3-c]cinnolin-3-one

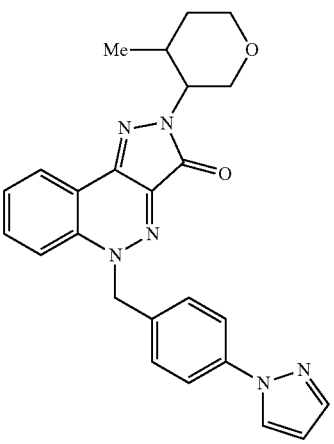 [SMILES: CC1CCOCC1n1nc2c3ccccc3n(Cc3ccc(-n4cccn4)cc3)nc-2c1=O]

Step 1: Preparation of 4-methyltetrahydro-2H-pyran-4-ol

Tetrahydro-4H-pyran-4-one was (2.5 g, 25 mmol) was dissolved in diethyl ether and cooled to 0° C. Methylmagnesium bromide (22 mL, 1.4 M toluene, 31 mmol, 1.25 equiv) was added dropwise over 10 minutes, the mixture was warmed to ambient temperature and stirred for 1 hour. The mixture was cooled to 0° C., treated with ammonium chloride (25 mL, saturated aqueous) and extracted with diethyl ether (2×30 mL). The combined organic extracts were washed once with brine, dried with sodium sulfate, filtered and concentrated at 23° C. (14 mm Hg) to afford the titled compound.

Step 2: Preparation of 4-methyl-3,6-dihydro-2H-pyran

A solution of 4-methyltetrahydro-2H-pyran-4-ol (2.87 g, 24.7 mmol) in benzene (30 mL) was treated with Burgess' Reagent (6.18 g, 25.9 mmol, 1.05 equiv) and placed into an oil bath preheated to 30° C. for 4 hours. The mixture was purified by silica gel gradient chromatography (100:0 to 90:10; hexanes:ethyl acetate), providing the titled compound.

Step 3: Preparation of (±)-cis-4-methyltetrahydro-2H-pyran-3-ol

A tetrahydrofuran (80 mL) solution of 4-methyl-3,6-dihydro-2H-pyran (1.4 g, 14 mmol) was treated with borane-methyl sulfide complex (5.0 mL, 53 mmol, 3.7 equiv), stirred at ambient temperature for 5.5 hours and cooled to 0° C. Sodium hydroxide (8.7 mL, 3 M aqueous, 26 mmol, 1.8 equiv) was added, followed by hydrogen peroxide [2.75 mL, 35% aqueous (w/w), 31 mmol, 2.2 equiv], and the mixture was stirred at ambient temperature for 3 hours, diluted with water (50 mL) and extracted with ethyl acetate (3×50 mL). The combined organic extracts were washed with brine, dried with sodium sulfate, filtered and concentrated in vacuo. The residue was purified by silica gel gradient chromatography (100:0 to 40:60; hexanes:ethyl acetate), providing the titled compound.

Step 4: Preparation of (±)-4-methyldihydro-2H-pyran-3(4H)-one

A solution of (±)-cis-4-methyltetrahydro-2H-pyran-3-ol (127 mg, 1.09 mmol) in acetonitrile (4 mL) was treated with 2-iodoxybenzoic acid (918 mg, 3.28 mmol, 3 equiv) and the mixture was placed into an oil bath preheated at 80° C. for 1.5 hours. The mixture was cooled to ambient temperature, filtered and the filtrate was concentrated in vacuo, providing the titled compound.

Step 5: Preparation of (±)-cis,trans-tert-butyl-2-[4-methyltetrahydro-2H-pyran-3-yl]hydrazinecarboxylate A solution of (±)-4-methyldihydro-2H-pyran-3(4H)-one (118 mg, 1.03 mmol) in 1,2-dichloroethane (1.5 mL) was treated with tert-butyl carbazate (150 mg, 1.14 mmol, 1.1 equiv) and acetic acid (0.296 mL, 5.17 mmol, 5 equiv). After stirring at ambient temperature for 30 minutes, the mixture was cooled to 0° C. and sodium triacetoxyborohydride (307 mg, 1.45 mmol, 1.4 equiv) was added portionwise over 20 minutes. The mixture was warmed to ambient temperature and stirred for 1.5 hours, treated with sodium bicarbonate (saturated aqueous) until the pH of the solution was <8. The mixture was extracted with chloroform (3×30 mL) and the combined organic extracts were washed with brine, dried with sodium sulfate, filtered and concentrated in vacuo. The residue was purified by silica gel gradient chromatography (100:0 to 40:60; hexanes:ethyl acetate), providing the titled compound.

Step 6: Preparation of (±)-cis,trans-(4-methyltetrahydro-2H-pyran-3-yl)hydrazine hydrochloride A solution of (±)-cis,trans-tert-butyl-2-[4-methyltetrahydro-2H-pyran-3-yl]hydrazinecarboxylate (64 mg, 0.28 mmol) in ethyl acetate (6 mL) was treated with gaseous hydrogen chloride at 0° C. for 1 minute. The vessel was sealed, stirred at 0° C. for 2 hours and concentrated in vacuo, providing the titled compound.

Step 7: Preparation of (±)-2-[cis,trans-4-methyltetrahydro-2H-pyran-3-yl]-5-[4-(1H-pyrazol-1-yl)benzyl]-2,5-dihydro-3H-pyrazolo[4,3-c]cinnolin-3-one A solution of ethyl-1-[4-(1H-pyrazol-1-yl)benzyl]-4-thioxo-1,4-dihydrocinnoline-3-carboxylate [(Example 1, Step 2), 109 mg, 0.279 mmol) in 1,2-dimethoxyethane (1 mL) and degassed N,N-dimethylformamide (0.2 mL) was treated with (±)-cis,trans-(4-methyltetrahydro-2H-pyran-3-yl)hydrazine hydrochloride (46.5 mg, 0.279 mmol, 1 equiv), potassium carbonate (386 mg, 2.79 mmol, 10 equiv) and mercury (II) chloride (76.0 mg, 0.279 mmol, 1 equiv). The mixture was stirred at ambient temperature for 1.5 hours, diluted with water (10 mL) and extracted with ethyl acetate (3×30 mL). The combined organic extracts were washed three times with water and once with brine, dried with sodium sulfate, filtered and concentrated in vacuo. The residue was purified by silica gel gradient chromatography (100:0 to 96:4; chloroform:methanol) to afford the titled compound as a red solid: $^1$H-NMR (400 MHz, CDCl$_3$) δ 8.35-8.24 (1H, br s), 7.91-7.86 (1H, s), 7.72-7.65 (3H, m), 7.56-7.46 (3H, m), 7.43-7.35 (2H, m), 6.45 (1H, s), 5.83 (2H, s), 4.74 (1H, br s), 4.41-3.47 (5H, m), 2.44-2.22 (1H, m), 1.86-1.63 (1H, m), 1.00-0.89 (3H, d, J=6.7 Hz) ppm; high resolution mass spectrometry (ES+) m/z 441.2048 [(M+H)$^+$; calculated for $C_{25}H_{25}N_6O_2$: 441.2034].

Example 72 trans-2-[4-Methyltetrahydro-2H-pyran-3-yl]-5-[4-(1H-pyrazol-1-yl)benzyl]-2,5-dihydro-3H-pyrazolo[4,3-c]cinnoline-3-one

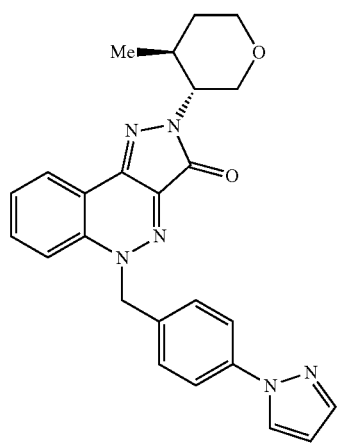 [SMILES: C[C@H]1CCOC[C@@H]1n1nc2c3ccccc3n(Cc3ccc(-n4cccn4)cc3)nc-2c1=O]

Example 71 was further purified by preparative chiral HPLC (2 cm IC column, 60:40; ethanol:heptane), producing a first-eluting, second-eluting, third-eluting, and fourth-eluting isomer. The first-eluting peak was determined to the titled compound (enantiopure, relative trans stereochemical configuration), of which the absolute stereochemistry is unknown: $^1$H-NMR (400 MHz, CDCl$_3$) δ 8.28 (1H, br s), 7.89 (1H, s), 7.72-7.65 (3H, m), 7.58-7.48 (3H, m), 7.42-7.35 (2H, d, J=8.6 Hz), 6.46 (1H, s), 5.84 (2H, s), 4.39-4.30 (1H, ddd, J=11.1, 6.6, 4.1 Hz), 4.04-3.96 (1H, m), 3.74 (1H, t, J=11.1 Hz), 3.56 (1H, t, J=11.5 Hz), 2.39 (1H, m), 1.83 (1H, br d, J=11.7 Hz), 1.64-1.53 (2H, m), 0.92 (3H, d, J=6.7 Hz) ppm; high resolution mass spectrometry (ES+) m/z 441.2035 [(M+H)$^+$; calculated for $C_{25}H_{25}N_6O_2$: 441.2034].

Example 73 cis-2-[4-Methyltetrahydro-2H-pyran-3-yl]-5-[4-(1H-pyrazol-1-yl)benzyl]-2,5-dihydro-3H-pyrazolo[4,3-c]cinnoline-3-one

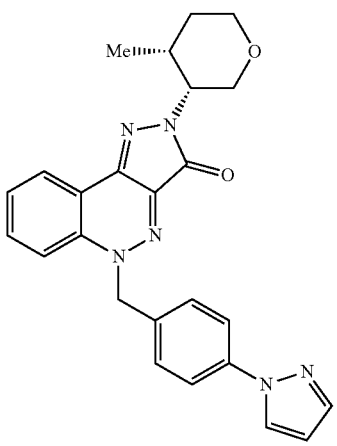 [SMILES: C[C@@H]1CCOC[C@@H]1n1nc2c3ccccc3n(Cc3ccc(-n4cccn4)cc3)nc-2c1=O]

Example 71 was further purified by preparative chiral HPLC (2 cm IC column, 60:40; ethanol:heptane), producing a first-eluting, second-eluting, third-eluting, and fourth-eluting isomer. The second-eluting peak was determined to the titled compound (enantiopure, relative cis stereochemical configuration), of which the absolute stereochemistry is unknown: $^1$H-NMR (400 MHz, CDCl$_3$) δ 8.34 (1H, bs), 7.90 (1H, s), 7.73-7.65 (3H, m), 7.55-7.47 (3H, m), 7.43-7.37 (2H, d, J=8.6 Hz), 6.46 (1H, s), 5.84 (2H, s), 4.73 (1H, dd, J=7.7, 4.1 Hz), 4.24-4.18 (1H, dd, J=12.3, 4.1 Hz), 4.10 (1H, m), 3.90-3.84 (1H, dd, J=11.8, 3.6 Hz), 3.78-3.67 (2H, m), 2.43-2.24 (1H, m), 1.72-1.63 (1H, m), 0.97 (3H, d, J=6.5 Hz) ppm;

Example 74 trans-2-[4-Methyltetrahydro-2H-pyran-3-yl]-5-[4-(1H-pyrazol-1-yl)benzyl]-2,5-dihydro-3H-pyrazolo[4,3-c]cinnoline-3-one

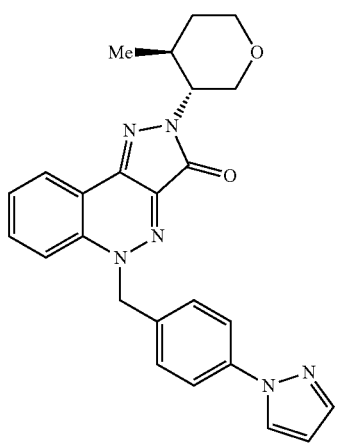 [SMILES: C[C@H]1CCOC[C@@H]1n1nc2c3ccccc3n(Cc3ccc(-n4cccn4)cc3)nc-2c1=O]

Example 71 was further purified by preparative chiral HPLC (2 cm IC column, 60:40; ethanol:heptane), producing a first-eluting, second-eluting, third-eluting, and fourth-eluting isomer. The third-eluting peak was determined to the titled compound (enantiopure, relative trans stereochemical configuration), of which the spectral data are identical to Example 72.

Example 75 cis-2-[4-Methyltetrahydro-2H-pyran-3-yl]-5-[4-(1H-pyrazol-1-yl)benzyl]-2,5-dihydro-3H-pyrazolo[4,3-c]cinnoline-3-one

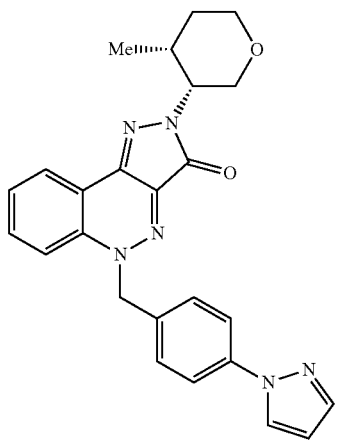 [SMILES: C[C@@H]1CCOC[C@@H]1n1nc2c3ccccc3n(Cc3ccc(-n4cccn4)cc3)nc-2c1=O]

Example 71 was further purified by preparative chiral HPLC (2 cm IC column, 60:40; ethanol:heptane), producing a first-eluting, second-eluting, third-eluting, and fourth-eluting isomer. The fourth-eluting peak was determined to the titled compound (enantiopure, relative cis stereochemical configuration), of which the spectral data are identical to Example 73.

Example 76

(±)-cis,trans-2-methyltetrahydro-2H-pyran-3-yl]-5-[4-(1H-pyrazol-1-yl)benzyl]-2,5-dihydro-3H-pyrazolo[4,3-c]cinnolin-3-one

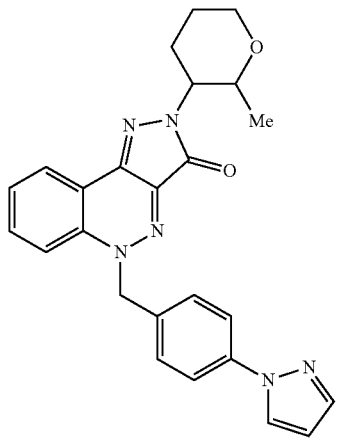 [SMILES: CC1OCCCC1n1nc2c3ccccc3n(Cc3ccc(-n4cccn4)cc3)nc-2c1=O]

Step 1: Preparation of (±)-methyl 2-(prop-2-en-1-yloxy)propanoate (±)-Methyl-2-hydroxypropanoate (7.6 g, 74 mmol) was dissolved in tetrahydrofuran (100 mL), cooled to 0° C. and treated with sodium hydride (3.6 g, 60% dispersion, 89 mmol, 1.2 equiv) portionwise over 45 minutes. The mixture was warmed to ambient temperature, stirred for 30 minutes, and then cooled to 0° C. Allyl bromide (8.4 mL, 96 mmol, 1.3 equiv) was added, the mixture was warmed to ambient temperature and stirred for an additional 14 hours. Sodium bicarbonate (10 mL, aqueous saturated) was added slowly and the mixture was stirred for 30 minutes before being poured into water (500 mL). The aqueous layer was extracted with ethyl acetate (2×300 mL) and the combined organic extracts were washed once with brine, dried with sodium sulfate, filtered and concentrated in vacuo, providing the titled compound.

Step 2: Preparation of (±)-N-methoxy-N-methyl-2-(prop-2-en-1-yloxy)propanamide

A suspension of N-methyl-O-methyl hydroxylamine hydrochloride (10.0 g, 104 mmol, 2 equiv) in dichloromethane (100 mL) was treated with trimethylaluminum (52.0 mL, 104 mmol, 2 equiv) at 0° C. After stirring for 1 hour at 0° C., a dichloromethane (50 mL) solution of (±)-methyl 2-(prop-2-en-1-yloxy)propanoate (7.50 g, 52.0 mmol) was added over 15 minutes. The mixture was warmed to ambient temperature and stirred for an additional 14 hours. The mixture was treated with water (500 mL) and extracted with dichloromethane (2×300 mL). The combined organic extracts were dried with sodium sulfate, filtered, and concentrated in vacuo to provide the titled compound.

Step 3: Preparation of (±)-4-(prop-2-en-1-yloxy)pent-1-en-3-one (±)-N-Methoxy-N-methyl-2-(prop-2-en-1-yloxy)propanamide (1.26 g, 7.27 mmol) was dissolved in tetrahydrohigh resolution mass spectrometry (ES+) m/z 441.2034 [(M+H)$^+$; calculated for $C_{25}H_{25}N_6O_2$: 441.2034].

furan (20 mL) and cooled to −78° C. Vinylmagnesium bromide (11.4 mL, 0.7 M solution in tetrahydrofuran, 8.00 mmol, 1.1 equiv) was added and the mixture was stirred at −78° C. for 10 minutes. Hydrochloric acid (5 mL, 4 M aqueous) was added, the mixture was warmed to ambient temperature and extracted with chloroform (2×30 mL). The combined organic extracts were dried with sodium sulfate, filtered, and concentrated in vacuo. The residue was purified by silica gel gradient chromatography (100:0 to 30:70; hexanes:ethyl acetate), providing the titled compound.

Step 4: Preparation of
(±)-2-methyl-2H-pyran-3(6H)-one

A dichloromethane (87 mL) solution of (±)-4-(prop-2-en-1-yloxy)pent-1-en-3-one (831 mg, 5.93 mmol) was sparged under nitrogen and treated with para-benzoquinone (64.0 mg, 0.593 mmol, 0.1 equiv) and Zhan Catalyst 1B (435 mg, 0.593 mmol, 0.1 equiv). After stirring at ambient temperature for 2 hours, the mixture was concentrated in vacuo and the residue was purified by silica gel chromatography (100:0 to 30:70; hexanes:ethyl acetate), providing the titled compound.

Step 5: Preparation of (±)-tert-butyl-2-(2-methyldihydro-2H-pyran-3(4H)-ylidene)hydrazinecarboxylate A methanol (9 mL) solution of (±)-2-methyl-2H-pyran-3 (6H)-one (370 mg, 3.30 mmol) was treated with a suspension of 10% palladium on carbon (185 mg) in methanol (3 mL). The mixture was sparged under hydrogen and stirred for 45 minutes at ambient temperature. The mixture was sparged under nitrogen, treated with tert-butyl carbazate (436 mg, 3.30 mmol, 1 equiv) and acetic acid (0.756 mL, 13.2 mmol, 4 equiv) and sparged under hydrogen. After stirring for 1 hour, the mixture was sparged under nitrogen and filtered through a pad of celite. The filtrate was concentrated in vacuo and the residue was dissolved in ethyl acetate, washed with sodium bicarbonate (30 mL, saturated aqueous) and the organic extract was dried with sodium sulfate, filtered and concentrated in vacuo. The residue was purified by silica gel gradient chromatography (100:0 to 20:80; hexanes:ethyl acetate) to provide the titled compound.

Step 6: Preparation of (±)-cis,trans-tert-butyl 2-(2-methyltetrahydro-2H-pyran-3-yl)hydrazine carboxylate A solution of (±)-tert-butyl-2-(2-methyldihydro-2H-pyran-3(4H)-ylidene)hydrazinecarboxylate (383 mg, 1.68 mmol) in absolute ethanol (5 mL) was treated with sodium borohydride (258 mg, 6.82 mmol, 4.1 equiv) and placed into an oil bath preheated at 35° C. for 12 hours. The mixture was concentrated in vacuo and the residue was dissolved in ethyl acetate (50 mL), washed once with sodium carbonate (25 mL, 10% aqueous). The aqueous extracted was further extracted with ethyl acetate (1×50 mL) and the combined organic extracts were dried with sodium sulfate, filtered and concentrated in vacuo. The residue was purified by silica gel gradient chromatography (100:0 to 0:100; hexanes:ethyl acetate), providing the titled compound.

Step 7: Preparation of (±)-cis,trans-(2-methyltetrahydro-2H-pyran-3-yl)hydrazine hydrochloride (±)-cis,trans-tert-butyl 2-(2-methyltetrahydro-2H-pyran-3-yl)hydrazine carboxylate (194 mg, 0.842 mmol) was dissolved in ethyl acetate (6 mL) and cooled to 0° C., which was then saturated with gaseous hydrogen chloride. The vessel was sealed and stirred at 0° C. for 2 hours. The mixture was concentrated in vacuo, providing the titled compound.

Step 8: Preparation of (±)-cis,trans-2-methyltetrahydro-2H-pyran-3-yl]-5-[4-(1H-pyrazol-1-yl)benzyl]-2,5-dihydro-3H-pyrazolo[4,3-c]cinnolin-3-one A 1,2-dimethoxyethane (2.5 mL) and degassed N,N-dimethylformamide (0.5 mL) solution of ethyl-1-[4-(1H-pyrazol-1-yl)benzyl]-4-thioxo-1,4-dihydrocinnoline-3-carboxylate [(Example 1, Step 2), 330 mg, 0.845 mmol] was treated with (±)-cis,trans-(2-methyltetrahydro-2H-pyran-3-yl)hydrazine hydrochloride (141 mg, 0.845 mmol, 1 equiv), potassium carbonate (1.17 g, 8.45 mmol, 10 equiv) and mercury(II) chloride (229 mg, 0.845 mmol, 1 equiv). After stirring at ambient temperature for 2 hours, the mixture was diluted with water (10 mL) and extracted with ethyl acetate (3×30 mL). The combined organic extracts were washed three times with water and once with brine, dried with sodium sulfate, filtered and concentrated in vacuo. The residue was purified by silica gel gradient chromatography (100:0 to 96:4; chloroform:methanol), providing the titled compound as a red solid: $^1$H-NMR (400 MHz, CDCl$_3$) δ 8.39-8.24 (1H, br s), 7.89 (1H, s), 7.74-7.65 (3H, m), 7.56-7.46 (3H, m), 7.41-7.36 (2H, m), 6.45 (1H, s), 5.84 (2H, s), 4.72 (1H, br s), 4.38-3.53 (3H, m), 2.71-1.74 (4H, m), 1.13 (3H, t, J=5.7 Hz) ppm; high resolution mass spectrometry (ES+) m/z 441.2033 [(M+H)$^+$; calculated for C$_{25}$H$_{25}$N$_6$O$_2$: 441.2034].

Example 77 trans-2-methyltetrahydro-2H-pyran-3-yl]-5-[4-(1H-pyrazol-1-yl)benzyl]-2,5-dihydro-3H-pyrazolo[4,3-c]cinnolin-3-one

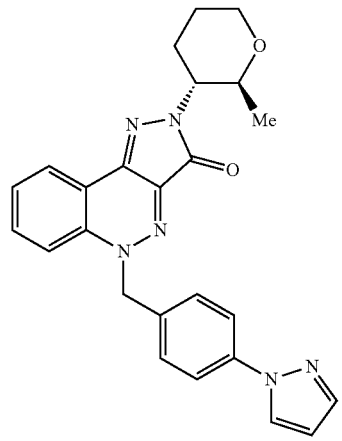 [SMILES: C[C@@H]1OCCC[C@H]1n1nc2c3ccccc3n(Cc3ccc(-n4cccn4)cc3)nc-2c1=O]

Example 76 was further purified by preparative chiral HPLC (Chiral Pak AD column, 100% methanol) to produce a first-eluting, second-eluting, third-eluting, and fourth-eluting isomer. The first-eluting peak was determined to the titled compound (enantiopure, relative trans stereochemical configuration), of which the absolute stereochemistry is unknown: $^1$H-NMR (400 MHz, CDCl$_3$) δ 8.28 (1H, br s), 7.89 (1H, s), 7.72-7.65 (3H, m), 7.57-7.48 (3H, m), 7.42-7.36 (2H, d, J=8.5 Hz), 6.46 (1H, s), 5.84 (2H, s), 4.33 (1H, t, J=11.4 Hz), 4.02 (1H, br d, J=11.4 Hz), 3.98-3.91 (1H, m), 3.59 (1H, t, J=11.4 Hz), 2.21 (1H, ddd, J=17.1, 12.8, 4.1 Hz), 2.04 (1H, br d, J=12.4 Hz), 1.90 (1H, m), 1.79 (1H, m), 1.14 (3H, d, J=5.9 Hz) ppm; high resolution mass spectrometry (ES+) m/z 441.2036 [(M+H)$^+$; calculated for C$_{25}$H$_{25}$N$_6$O$_2$: 441.2034].

Example 78 cis-2-Methyltetrahydro-2H-pyran-3-yl]-5-[4-(1H-pyrazol-1-yl)benzyl]-2,5-dihydro-3H-pyrazolo[4,3-c]cinnolin-3-one

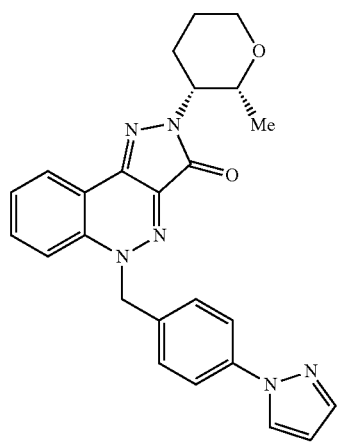 [SMILES: C[C@H]1OCCC[C@H]1n1nc2c3ccccc3n(Cc3ccc(-n4cccn4)cc3)nc-2c1=O]

Example 76 was resolved by preparative chiral HPLC (Chiral Pak AD column, 100% methanol) to produce a first-eluting, second-eluting, third-eluting, and fourth-eluting isomer. The second-eluting peak was determined to the titled compound (enantiopure, relative cis stereochemical configuration), of which the absolute stereochemistry is unknown: $^1$H-NMR (400 MHz, CDCl$_3$) δ 8.37 (1H, br s), 7.89 (1H, s), 7.73-7.65 (3H, m), 7.55-7.47 (3H, m), 7.43-7.35 (2H, d, J=8.4 Hz), 6.46 (1H, s), 5.84 (2H, s), 4.71 (1H, br s), 4.17 (1H, br d, J=11.6 Hz), 3.95 (1H, m), 3.67 (1H, t, J=11.6 Hz), 3.03 (1H, br s), 2.66 (1H, br s), 2.20-2.04 (2H, m), 1.13 (3H, d, J=6.4 Hz) ppm; high resolution mass spectrometry (ES+) m/z 441.2047 [(M+H)$_+$; calculated for C$_{25}$H$_{25}$N$_6$O$_2$: 441.2034].

Example 79 trans-2-Methyltetrahydro-2H-pyran-3-yl]-5-[4-(1H-pyrazol-1-yl)benzyl]-2,5-dihydro-3H-pyrazolo[4,3-c]cinnolin-3-one

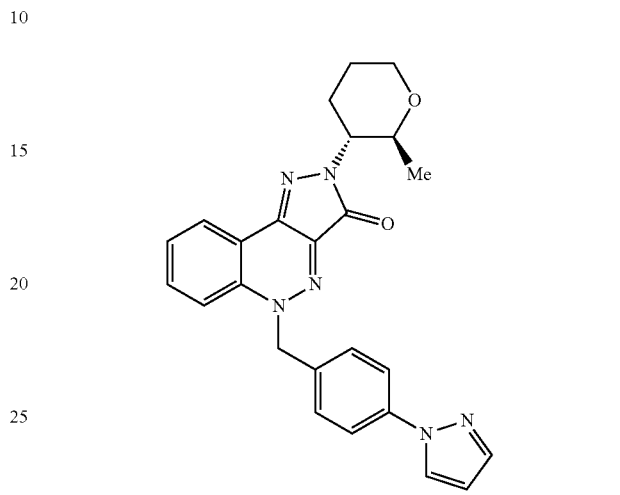

Example 76 was resolved by preparative chiral HPLC (Chiral Pak AD column, 100% methanol) to produce a first-eluting, second-eluting, third-eluting, and fourth-eluting isomer. The third-eluting peak was determined to the titled compound (enantiopure, relative trans stereochemical configuration), of which the absolute stereochemistry is unknown. Spectral data were identical to Example 77.

Example 80 cis-2-Methyltetrahydro-2H-pyran-3-yl]-5-[4-(1H-pyrazol-1-yl)benzyl]-2,5-dihydro-3H-pyrazolo[4,3-c]cinnolin-3-one Example 76 was resolved by preparative chiral HPLC (Chiral Pak AD column, 100% methanol) to produce a first-eluting, second-eluting, third-eluting, and fourth-eluting isomer. The fourth-eluting peak was determined to the titled compound (enantiopure, relative cis stereochemical configuration), of which the absolute stereochemistry is unknown. Spectral data were identical to Example 78.

Example 81

2-(2-Methylphenyl)-5-[6-(morpholin-4-yl)pyridine-3-yl]methyl-2,5-dihydro-3H-pyrazolo[4,3-c]cinnolin-3-one

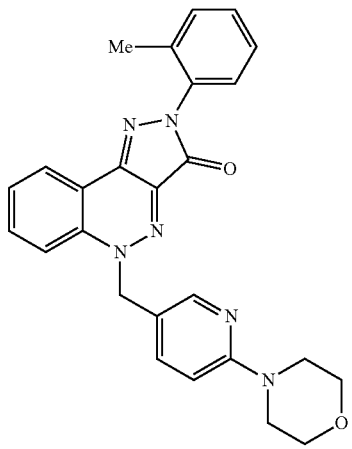 [SMILES: Cc1ccccc1-n1nc2c3ccccc3n(Cc3ccc(N4CCOCC4)nc3)nc-2c1=O]

5-[(6-Bromopyridin-3-yl)methyl]-2-(2-methylphenyl)-2,5-dihydro-3H-pyrazolo[4,3-c]cinnolin-3-one [(Example 22), 60 mg, 0.13 mmol] was dissolved in dimethyl sulfoxide (1 mL) and treated with morpholine (35 mg, 0.40 mmol, 3 equiv) and potassium carbonate (19 mg, 0.13 mmol, 1 equiv). The vessel was sealed and placed into an oil bath preheated at 100° C. for 9 hours. The mixture was cooled to ambient temperature, poured into water (5 mL) and extracted with ethyl acetate (3×20 mL). The combined organic extracts were washed three times with water and once with brine, dried over sodium sulfate, filtered, and concentrated in vacuo. The residue was purified by silica gel gradient chromatography (100:0 to 94:6; chloroform:methanol), providing the titled compound: $^1$H-NMR (400 MHz, CDCl$_3$) δ 8.29 (1H, br s), 7.69-7.59 (3H, m), 7.57-7.51 (2H, m), 7.44 (1H, m), 7.38-7.29 (3H, m), 6.59 (1H, d, J=9.1 Hz), 5.73 (2H, s), 3.79 (4H, m), 3.50 (4H, m), 2.35 (3H, s) ppm; high resolution mass spectrometry (ES+) m/z 453.2038 [(M+H)$^+$; calculated for C$_{26}$H$_{25}$N$_6$O$_2$: 453.2034].

Example 82

2-(2-Methylphenyl)-5-{[6-(1,3-thiazol-4-yl)pyridin-3-yl]methyl}-2,5-dihydro-3H-pyrazolo[4,3-c]cinnolin-3-one

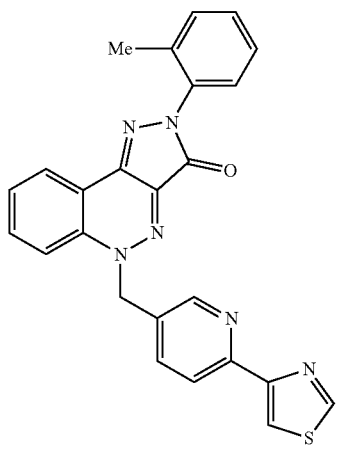 [SMILES: Cc1ccccc1-n1nc2c3ccccc3n(Cc3ccc(-c4cscn4)nc3)nc-2c1=O]

5-[(6-Bromopyridin-3-yl)methyl]-2-(2-methylphenyl)-2,5-dihydro-3H-pyrazolo[4,3-c]cinnolin-3-one [(Example 22), 77 mg, 0.17 mmol] and 4-(tributylstannyl)thiazole (77 mg, 0.21 mmole, 1.2 equiv) were dissolved in degassed N,N-dimethylformamide (1 mL) and treated with cesium fluoride (52 mg, 0.34 mmol, 2 equiv), copper(I) iodide (13 mg, 0.069 mmol, 0.4 equiv), and tetrakis(triphenylphosphine)palladium (0) (40 mg, 0.035 mmol, 0.2 equiv). The mixture was stirred at ambient temperature for one hour, diluted with ethyl acetate (15 mL) and filtered. The filtrate was concentrated in vacuo and the residue was purified by preparative reverse phase HPLC (15:85 to 65:35; acetonitrile containing 0.01% trifluoroacetic acid:water containing 0.01% trifluoroacetic acid), providing the titled compound: $^1$H-NMR (400 MHz, CDCl$_3$) δ 9.13 (1H, s), 8.95 (1H, s), 8.50 (1H, s), 8.35 (2H, br d, J=7.9 Hz), 8.08 (1H, d, J=8.5 Hz), 7.73-7.60 (3H, m), 7.45 (1H, br s), 7.39-7.31 (3H, m), 5.97 (2H, s), 2.73 (3H, s) ppm;

low resolution mass spectrometry (ES+) m/z 451.3 [(M+H)+; calculated for $C_{25}H_{19}N_6OS$: 451.3].

Example 83

2-(2,3-Dimethylphenyl)-5-{[6-(1,3-thiazol-4-yl)pyridin-3-yl]methyl}-2,5-dihydro-3H-pyrazolo[4,3-c]cinnolin-3-one

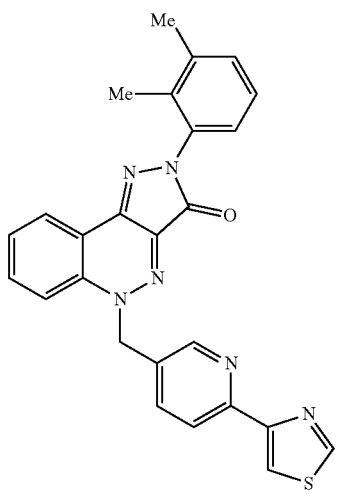 [SMILES: Cc1cccc(-n2nc3c4ccccc4n(Cc4ccc(-c5cscn5)nc4)nc-3c2=O)c1C]

Step 1: Preparation of ethyl 1-[(6-bromopyridin-3-yl)methyl]-4-oxo-1,4-dihydrocinnoline-3-carboxylate Using the procedures described in Example 31, substituting (6-bromopyridin-3-yl)methyl methanesulfonate for 1-[4-(bromomethyl)phenyl]-1H-pyrazole (Step 3), the titled compound was obtained.

Step 2: Preparation of ethyl 4-oxo-1-{[6-(1,3-thiazol-4-yl)pyridin-3-yl]methyl}-1,4-dihydrocinnoline-3-carboxylate Ethyl 1-[(6-bromopyridin-3-yl)methyl]-4-oxo-1,4-dihydrocinnoline-3-carboxylate (897 mg, 2.31 mmol), 4-(tributylstannanyl)-1,3-thiazole (1.04 g, 2.77 mmol, 1.2 equiv), copper(I) iodide (176 mg, 0.924 mmol, 0.4 equiv), cesium fluoride (702 mg, 4.62 mmol, 2 equiv) and tetrakis(triphenylphosphine)palladium(0) (534 mg, 0.462 mmol, 0.2 equiv) were combined in degassed N,N'-dimethylformamide (6 mL) and stirred for 1 hour at ambient temperature. The mixture was poured into water and extracted twice with ethyl acetate. The combined organic extracts were dried with sodium sulfate, filtered and concentrated in vacuo. The residue was dissolved in chloroform, treated with potassium fluoride on Celite (8 g, 10 weight equiv) and after stirring vigorously for 24 hours, was filtered. The filtrate was concentrated in vacuo and the residue was purified by silica gel gradient chromatography (100:0 to 0:100; hexanes:ethyl acetate; then 100:0 to 95:5; chloroform:methanol), providing the titled compound.

Step 3: Preparation of ethyl 1-{[6-(1,3-thiazol-4-yl)pyridin-3-yl]methyl}-4-thioxo-1,4-dihydrocinnoline-3-carboxylate Ethyl 4-oxo-1-{[6-(1,3-thiazol-4-yl)pyridin-3-yl]methyl}-1,4-dihydrocinnoline-3-carboxylate (750 mg, 2.00 mmol) was dissolved in toluene (9 mL), sparged under nitrogen and treated with Lawesson's Reagent (486 mg, 1.20 mmol, 0.6 equiv). The mixture was placed into an oil bath preheated to 105° C. for 1 hour, cooled to ambient temperature and concentrated in vacuo. The residue was purified by silica gel gradient chromatography (100:0 to 60:40; hexanes: ethyl acetate) to provide the titled compound as a dark green solid.

Step 4: Preparation of 5-{[6-(1,3-thiazol-4-yl)pyridin-3-yl]methyl}-2,5-dihydro-3H-pyrazolo[4,3-c]cinnolin-3-one Ethyl 1-{[6-(1,3-thiazol-4-yl)pyridin-3-yl]methyl}-4-thioxo-1,4-dihydrocinnoline-3-carboxylate (240 mg, 0.612 mmol) and Lawesson's Reagent (173 mg, 0.7 equiv) were suspended in toluene (4 mL) and tetrahydrofuran (2 mL) and placed into an oil bath preheated to 105° C. for 30 minutes. The mixture was cooled to ambient temperature, concentrated in vacuo and the residue was purified by silica gel gradient chromatography (100:0 to 96:4; chloroform:methanol), providing the titled compound.

Step 5: Preparation of 2-(2,3-Dimethylphenyl)-5-{[6-(1,3-thiazol-4-yl)pyridin-3-yl]methyl}-2,5-dihydro-3H-pyrazolo[4,3-c]cinnolin-3-one 5-{[6-(1,3-Thiazol-4-yl)pyridin-3-yl]methyl}-2,5-dihydro-3H-pyrazolo[4,3-c]cinnolin-3-one (66 mg, 0.18 mmol) was dissolved in degassed N,N-dimethylformamide (1 mL) and copper (I) iodide (35 mg, 0.22 mmol, 1.2 equiv), 1-iodo-2,3-dimethylbenzene (51 mg, 0.22 mmol, 1.2 equiv), (±)-trans-N,N'-dimethylcyclohexane-1,2-diamine (78 mg, 0.549 mmol, 3 equiv) and potassium phosphate (0.27 g, 1.3 mmol, 7 equiv) were added. The vessel was sealed and placed into an oil bath preheated at 105° C. for 40 minutes. The mixture cooled to ambient temperature, diluted with water (5 mL) and extracted with ethyl acetate (3×30 mL). The combined organic extracts were washed three times with water and once with brine, dried with sodium sulfate, filtered and concentrated in vacuo. The residue was purified by silica gel gradient chromatography (100:0 to 96:4; chloroform:methanol), providing the titled compound: $^1$H-NMR (400 MHz, CDCl$_3$) δ 8.87 (1H, s), 8.69 (1H, s), 8.31 (1H, d, J=8.2 Hz), 8.16 (2H, m), 7.77 (1H, d, J=8.2 Hz), 7.57 (4H, m), 7.28 (1H, m), 7.22 (1H, d, J=3.9 Hz), 5.90 (2H, s), 2.37 (3H, s), 2.21 (3H, s) ppm; high resolution mass spectrometry (ES+) m/z 465.1499 [(M+H)+; calculated for $C_{26}H_{21}N_6OS$: 465.1492].

The following compounds were prepared according to the general procedure described in Example 83, substituting the appropriate aryl iodide for 1-iodo-2,3-dimethylbenzene (Step 5). The starting materials are either commercially available, known in the literature or may be prepared from commercially available reagents using conventional reactions well known in the art.

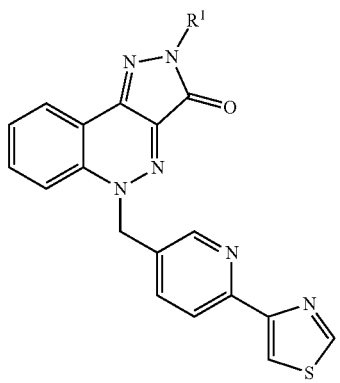

| Ex. | R[1] | HRMS/LRMS |
|---|---|---|
| 84 | (pyridine with F, Me) | C$_{24}$H$_{17}$FN$_7$OS [M + H] LRMS calc. 470.1 obs. 470.3 |
| 85 | (pyridine with F, Me) | C$_{24}$H$_{17}$FN$_7$OS [M + H] calc. 470.1194 obs. 470.1202 |

Example 86

2-(6-Fluoro-2-methylpyridin-3-yl)-5-{[6-(1-methyl-1H-pyrazol-4-yl)pyridin-3-yl]methyl}-2,5-dihydro-3H-pyrazolo[4,3-c]cinnolin-3-one

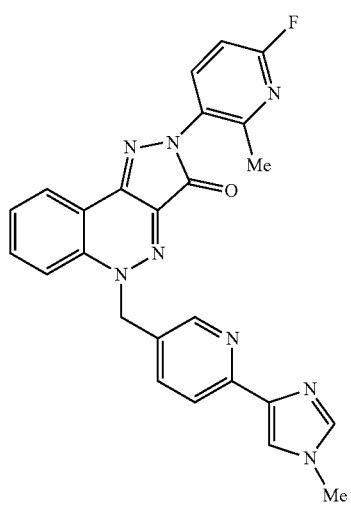 [SMILES: Cc1nc(F)ccc1-n1nc2c3ccccc3n(Cc3ccc(-c4cn(C)cn4)nc3)nc-2c1=O]

Step 1: Preparation of ethyl 1-{[6-(1-methyl-1H-pyrazol-4-yl)pyridin-3-yl]methyl}-4-oxo-1,4-dihydrocinnoline-3-carboxylate Ethyl 1-[(6-bromopyridin-3-yl)methyl]-4-oxo-1,4-dihydrocinnoline-3-carboxylate [(Example 83, Step 1), 748 mg, 1.93 mmol] and 1-methyl-4-(4,4,5,5-tetramethyl-1,3,2-dioxaborolan-2-yl)-1H-pyrazole (682 mg, 3.28 mmol, 1.7 equiv) were suspended in tetrahydrofuran (15 mL) and treated with an aqueous solution (1.5 mL) of cesium carbonate (1.26 g, 3.85 mmol, 2 equiv). The mixture was sparged under nitrogen, treated with bis(tri-tert-butylphosphine)palladium(0) (197 mg, 0.385 mmol, 0.2 equiv) and placed in an oil bath preheated to 80° C. for 1 hour. The mixture was cooled to ambient temperature, poured into sodium bicarbonate (75 mL, aqueous saturated) and extracted with ethyl acetate (2×100 mL). The combined organic extracts were dried with sodium sulfate, filtered and concentrated in vacuo. The residue was purified by silica gel gradient chromatography (100:0 to 0:100; hexanes:ethyl acetate), providing the titled compound.

Step 2: Preparation of 2-(6-Fluoro-2-methylpyridin-3-yl)-5-{[6-(1-methyl-1H-pyrazol-4-yl)pyridin-3-yl]methyl}-2,5-dihydro-3H-pyrazolo[4,3-c]cinnolin-3-one Using the procedures described in Example 85, substituting ethyl 1-{[6-(1-methyl-1H-pyrazol-4-yl)pyridin-3-yl]methyl}-4-oxo-1,4-dihydrocinnoline-3-carboxylate for ethyl 4-oxo-1-{[6-(1,3-thiazol-4-yl)pyridin-3-yl]methyl}-1,4-dihydrocinnoline-3-carboxylate (Example 83, Step 3), the titled compound was obtained: $^1$H-NMR (400 MHz, CDCl$_3$) δ 8.62 (1H, s), 8.30 (1H, d, J=7.9 Hz), 7.94-7.86 (3H, d, m), 7.68-7.57 (4H, m), 7.42 (1H, d, J=9.2 Hz), 6.92 (1H, m), 5.85 (2H, s), 3.95 (3H, s), 2.55 (3H, s) ppm; high resolution mass spectrometry (ES+) m/z 467.1756 [(M+H)$^+$; calculated for C$_{25}$H$_{20}$FN$_8$O: 467.1739].

The following compound was prepared according to the general procedure described in Example 86, substituting the appropriate aryl iodide for 6-fluoro-3-iodo-2-methylpyridine. The starting materials are either commercially available, known in the literature or may be prepared from commercially available reagents using conventional reactions well known in the art.

| Ex. | R[1] | HRMS/LRMS |
|---|---|---|
| 87 | (pyridine with F, Me) | C$_{25}$H$_{20}$FN$_8$O [M + H] calc. 467.1739 obs. 467.1756 |

Example 88

(±)-2-(trans-2-Hydroxycyclohexyl)-5-{[6-(1,3-thiazol-4-yl)pyridin-3-yl]methyl}-2,5-dihydro-3H-pyrazolo[4,3-c]cinnolin-3-one

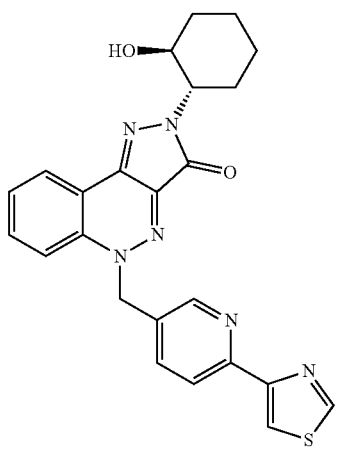 [SMILES: O=c1c2nn(Cc3ccc(-c4cscn4)nc3)c3ccccc3c-2nn1[C@H]1CCCC[C@@H]1O]

Using the procedures described in Example 83, substituting (±)-2-hydrazinylcyclohexanol for hydrazine, the titled compound was obtained: $^1$H-NMR (400 MHz, DMSO-$d_6$) δ 9.21 (1H, s), 8.73 (1H, s), 8.31 (1H, s), 8.16 (1H, d, J=7.9 Hz), 8.06 (1H, d, J=8.7 Hz), 7.98 (1H, d, J=8.7 Hz), 7.79 (1H, d, J=7.9 Hz), 7.72 (1H, t, J=7.9 Hz), 7.63 (1H, t, J=7.9 Hz), 6.00 (2H, s), 4.59 (1H, s), 4.08 (1H, t, J=10.8 Hz), 3.81 (1H, br s), 1.98 (1H, br s), 1.85-1.67 (4H, m), 1.41-1.28 (3H, m) ppm; high resolution mass spectrometry (ES+) m/z 459.1601 [(M+H)$^+$; calculated for $C_{24}H_{23}N_6O_2S$: 459.1598].

Example 89

2-(2-Methylphenyl)-5-[4-(6-methylpyridin-3-yl)benzyl]-2,5-dihydro-3H-pyrazolo[4,3-c]cinnolin-3-one

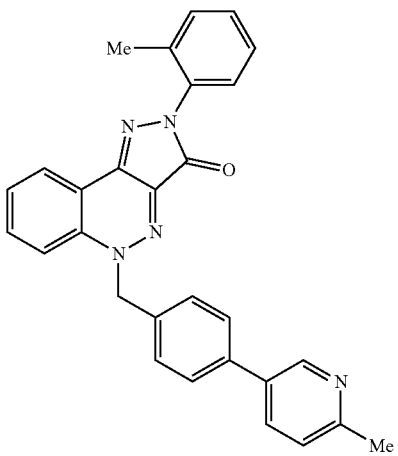 [SMILES: Cc1ccc(-c2ccc(Cn3nc4c(=O)n(-c5ccccc5C)nc-4c4ccccc43)cc2)cn1]

Using the procedures described in Example 47, substituting (2-methylphenyl)hydrazine hydrochloride for and (±)-tetrahydro-2H-pyran-3-ylhydrazine hydrochloride (Example 31, Step 7), the titled compound was obtained: $^1$H-NMR (400 MHz, DMSO-$d_6$) δ 8.96 (1H, s), 8.47 (1H, s), 8.20 (1H, d, J=8.9 Hz), 8.00 (1H, d, J=8.0 Hz), 7.81 (2H, d, J=8.0 Hz), 7.78-7.72 (2H, m), 7.68 (1H, t, J=8.0 Hz), 7.56 (2H, d, J=7.8 Hz), 7.44-7.33 (4H, m), 6.05 (2H, s), 2.65 (3H, s), 2.25 (3H, s) ppm; high resolution mass spectrometry (ES+) m/z 458.1981 [(M+H)$^+$; calculated for $C_{29}H_{24}N_5O$: 458.1975].

Example 90

2-(2,3-Dimethylphenyl)-5-[(6'-methyl-2,3'-bipyridin-5-yl)methyl]-2,5-dihydro-3H-pyrazolo[4,3-c]cinnolin-3-one

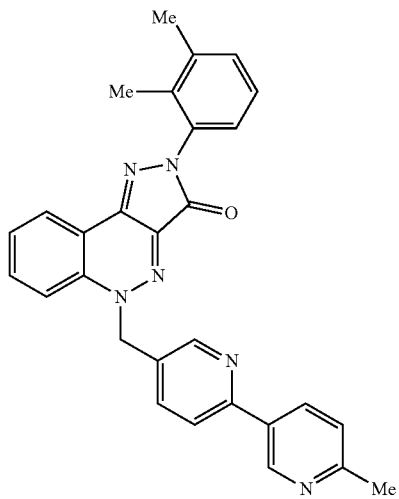 [SMILES: Cc1ccc(-c2ccc(Cn3nc4c(=O)n(-c5cccc(C)c5C)nc-4c4ccccc43)cn2)cn1]

Step 1: Preparation of 5-[(6-bromopyridin-3-yl)methyl]-2-(2,3-dimethylphenyl)-2,5-dihydro-3H-pyrazolo[4,3-c]cinnolin-3-one Using the procedures described in Example 18, substituting 2,3-dimethylphenyl hydrazine hydrochloride for 2-fluorophenyl hydrazine hydrochloride (Step 1), and substituting (6-bromopyridin-3-yl)methyl methanesulfonate for 1-[4-bromomethyl)phenyl]-1H-pyrazole (Step 3), the titled compound was obtained.

Step 2: Preparation of 2-(2,3-dimethylphenyl)-5-[(6'-methyl-2,3'-bipyridin-5-yl)methyl]-2,5-dihydro-3H-pyrazolo[4,3-c]cinnolin-3-one 5-[(6-Bromopyridin-3-yl)methyl]-2-(2,3-dimethylphenyl)-2,5-dihydro-3H-pyrazolo[4,3-c]cinnolin-3-one (0.10 g, 0.22 mmol), (6-methylpyridin-3-yl)-boronic acid (74 mg, 0.54 mmol, 2.5 equiv), palladium(II)acetate (9.7 mg, 0.043 mmol, 0.2 equiv), 1,1'-bis(diphenylphosphino)ferrocene (24 mg, 0.043 mmol, 0.2 equiv), copper(I)chloride (21 mg, 0.22 mmol, 1 equiv) and cesium carbonate (0.18 g, 0.54 mmol, 2.5 equiv) were combined in N,N-dimethylformamide (4 mL) and placed into an oil bath preheated to 100° C. for 60 minutes. The mixture was cooled to ambient temperature, poured into sodium bicarbonate (20 mL, aqueous saturated) and extracted with ethyl acetate (3×25 mL). The combined organic extracts were dried with sodium sulfate, filtered and concentrated in vacuo. The residue was purified by silica gel chromatography (100:0 to 90:10; dichloromethane:methanol), providing the titled compound as a deep red solid: $^1$H-NMR (400 MHz, CDCl$_3$) δ 9.06 (1H, d, J=2.1 Hz), 8.78 (1H, d, J=1.7 Hz), 8.32 (1H, dd, J=7.8, 1.0 Hz), 8.19 (1H, dd, J=8.1, 2.3 Hz), 7.77 (1H, dd, J=8.3, 2.4 Hz), 7.72 (1H, d, J=8.3 Hz), 7.65-7.54 (3H, m), 7.42-7.38 (1H, m), 7.30-7.22 (3H, m), 5.90 (2H, s), 2.61 (3H, s), 2.37 (3H, s), 2.20 (3H, s) ppm; high resolution mass spectrometry (ES+) m/z 473.2099 [(M+H)$^+$; calculated for C$_{29}$H$_{25}$N$_6$O: 473.2084].

The following compounds of formula (IIIB) wherein both R$^7$ are methyl were prepared according to the general procedure described in Example 90 (Step 2), substituting the appropriate boronic acid or ester for (6-methylpyridin-3-yl)-boronic acid. The starting materials are either commercially available, known in the literature or may be prepared from commercially available reagents using conventional reactions well known in the art.

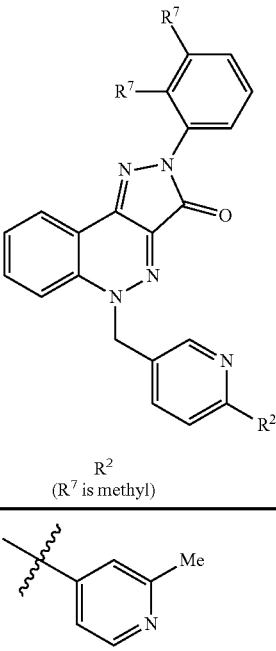

(IIIB)

| Ex. | R$^2$ (R$^7$ is methyl) | HRMS/LRMS |
|---|---|---|
| 91 | Me, pyridin-3-yl with 4-Me | C$_{29}$H$_{25}$N$_6$O [M + H] calc. 473.2084 obs. 473.2090 |
| 92 | pyridin-3-yl with 2-Me | C$_{29}$H$_{25}$N$_6$O [M + H] calc. 473.2084 obs. 473.2090 |
| 93 | pyridin-3-yl with 5-Me | C$_{29}$H$_{25}$N$_6$O [M + H] calc. 473.2084 obs. 473.2090 |
| 94 | pyridin-3-yl with 4-Me | C$_{29}$H$_{25}$N$_6$O [M + H] calc. 473.2084 obs. 473.2085 |
| 95 | pyridin-4-yl with 2-Me | C$_{29}$H$_{25}$N$_6$O [M + H] calc. 473.2084 obs. 473.2082 |

Example 96

2-(2,3-Dimethylphenyl)-5-[(6'-methyl-2,3'-bipyridin-5-yl)methyl]-2,5-dihydro-3H-pyrazolo[4,3-c]cinnolin-3-one

Preparation of 2-(2,3-dimethylphenyl)-5-[(6'-methyl-2,3'-bipyridin-5-yl)methyl]-2,5-dihydro-3H-pyrazolo[4,3-c]cinnolin-3-one 5-[(6-Bromopyridin-3-yl)methyl]-2-(2,3-dimethylphenyl)-2,5-dihydro-3H-pyrazolo[4,3-c]cinnolin-3-one (Example 90, Step 1, 25 mg, 0.054 mmol) was dissolved in tetrahydrofuran (0.5 mL), treated with tetrakis(triphenylphosphine)palladium(0) (12 mg, 0.0011 mmol) and cooled to 0° C. The mixture was treated with methylzinc chloride (42 μL, 0.081 mmol, 2 M solution in tetrahydrofuran, 1.5 equiv), warmed to ambient temperature and stirred for an additional 1 hour at ambient temperature. The mixture was treated with water (20 mL) and extracted with ethyl acetate (3×25 ml). The combined organic extracts were dried with sodium sulfate, filtered and concentrated in vacuo. The residue was purified by silica gel chromatography (100:0 to 60:40; dichloromethane:methanol containing 10% ammonium hydroxide), providing the titled compound as a deep red solid: $^1$H-NMR (400 MHz, CDCl$_3$) δ 8.60 (1H, d, J=1.6 Hz), 8.31 (1H, d, J=7.8 Hz), 7.69 (1H, d, J=7.1 Hz), 7.6 (1H, d, J=7.1 Hz), 7.63-7.53 (3H, s), 7.49-7.44 (1H, m), 7.29-7.22 (1H, m) m 7.14 (1H, d, J=8.2 Hz), 5.82 (2H, s), 2.55 (3H, s), 2.37 (3H, s), 2.20 (3H, s) ppm; high resolution mass spectrometry (ES+) m/z 396.1819 [(M+H)$^+$; calculated for C$_{24}$H$_{22}$N$_5$O: 396.1819].

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a FLIPR$^{384}$ Fluorometric Imaging Plate Reader System. The assay studies the effect of one or several concentrations of test compounds on basal or acetylcholine-stimulated Ca$^{2+}$ levels using FLIPR.

Compounds are prepared and subjected to a preincubation period of 4 min. Thereafter, a single EC$_{20}$ concentration of acetylcholine is added to each well (3 nM final). The intracellular Ca$^{2+}$ level of each sample is measured and compared to an acetylcholine control to determine any modulatory activity.

Cells: CHOnfat/hM1, hM2, hM3 or hM4 cells are plated 24 hr before the assay at a density of 18,000 cells/well (100 μL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 ug/ml hygromycin is added.

Equipment: 384 well plate, 120 μL addition plate; 96-well Whatman 2 ml Uniplate Incubator, 37° C., 5% CO$_2$; Skatron EMBLA-384 Plate Washer; Multimek Pipetting System; Genesis Freedom 200 System; Mosquito System; Temo Nanoliter Pipetting System; and FLIPR$^{384}$ Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1 N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 μM in buffer for a final concentration of 1 μM in Assay. 20% Pluronic Acid Solution stock, with concentration of 0.04% in Buffer, 0.02% in Assay.

65 μL of 2 mM Fluo-4AM are mixed with 130 μL of 20% Pluronic Acid. The resulting solution and 650 μL FBS is added to the assay buffer for a total volume of 65 mL. Positive Controls: 4-Br-A23187: 10 mM in DMSO; final concentration 10 μM. Acetylcholine: 10 mM in water, working stock at both 20 μM and 30 μM in assay buffer, final concentration of 10 μM. This is used to check the maximum stimulation of the CHOK1/hM1 cells. 20 μM (2×) acetylcholine is added in the preincubation part of the assay, and the 30 μM (3×) stock is added in the second part. (EC$_{20}$) Acetylcholine: 10 mM in water, working stock of 9 nM (3×), and final concentration in assay is 3 nM. This is used after the preincubation with test compounds. Addition of the EC$_{20}$ Acetylcholine to each well with a test compound will ascertain any modulator activity. 24 wells contain 3 nM Acetylcholine alone as a control.

Determining Activity of Putative Compounds:

Screening Plate Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanoliter Pipetting System by transferring 1 μl of serial diluted compounds to each well, and 1 mM acetylcholine (100× stock concentration) were added as a control. Using Temo, 49 μl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 μM acetylcholine control (3×) is added into control wells, and the 3× agonist plate is transferred into a 384 well plate.

Cells are washed three times with 100 μL of buffer, leaving 300 μL of buffer in each well. Using Multimek, 30 μL of Dye Loading Buffer is added into each well and incubated at 37° C., 5% CO$_2$ for up to one hr.

After 60 min, the cells are washed three times with 100 μL of buffer, leaving 30 μL of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

4 min of preincubation with the test compounds is provided to determine any agonist activity on the M1 receptor by comparison to the 1 mM acetylcholine control. After preincubation, the EC$_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 10 μM (10,000 nM) or less. The inflection point is calculated from the FLIPR values, and is a measure of activity. Such a result is indicative of the intrinsic activity of the compounds in use as M1 allosteric modulators.

IP values from the aforementioned assay for representative exemplary compounds of the invention (as described herein) are provided below in Table 1 below:

| Example | IP Value (nM) |
|---|---|
| 1 | 28 |
| 11 | 193 |
| 13 | 14 |
| 21 | 2862 |
| 23 | 748 |
| 25 | 144 |
| 61 | 42 |
| 62 | 21 |
| 63 | 593 |
| 64 | 61 |
| 65 | 1183 |
| 71 | 89 |
| 72 | 47 |
| 73 | 771 |
| 74 | 636 |
| 75 | 158 |
| 81 | 1371 |
| 86 | 225 |
| 90 | 29 |

The following abbreviations are used throughout the text:
Me: methyl
Et: ethyl
t-Bu: tert-butyl
Ar: aryl
Ph: phenyl
Bn: benzyl
DMF: dimethylformamide
Ac: acetyl
DMSO: dimethylsulfoxide
DMEM: Dulbecco's Modified Eagle Medium (High Glucose)
FBS: fetal bovine serum
rt: room temperature
aq: aqueous
HPLC: high performance liquid chromatography
MS: mass spectrometry While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

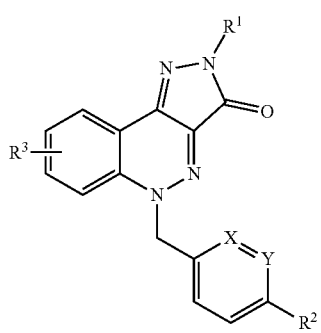

or a pharmaceutically acceptable salt thereof, wherein
—X=Y— is selected from the group consisting of:
(2) —CH=N—, or
(3) —N=CH—
$R^1$ is selected from the group consisting of
(1) aryl,
(2) a heteroaryl group which is a cyclic or polycyclic group, having from five to twelve ring atoms, said ring atoms selected from C, O, N or S, at least one of which is O, N or S,
(3) a heterocyclic group, which is a non-aromatic cyclic or polycyclic group having from three to twelve ring atoms selected from C, O, N or S, at least one of which is O, N or S,
(4) —$C_{1-6}$ alkyl,
(5) —$C_{3-8}$ cycloalkyl,
(6) —$C_{2-6}$ alkenyl
wherein said aryl, heteroaryl, heterocyclic, alkyl, alkenyl and cycloalkyl $R^1$ moiety is optionally substituted with one or more
(a) halogen,
(b) hydroxy,
(c) —O—$C_{1-6}$ alkyl,
(d) —$C_{1-6}$ alkyl, and
(e) cyano;
$R^2$ is selected from the group consisting of
(1) aryl,
(2) a heteroaryl group which is a cyclic or polycyclic group, having from five to twelve ring atoms, said ring atoms selected from C, O, N or S, at least one of which is O, N or S, or
(3) halogen,
wherein said aryl or heteroaryl $R^2$ moiety is optionally substituted with one or more
(a) halogen,
(b) hydroxy,
(c) —O—$C_{1-6}$ alkyl,
(d) —$C_{1-6}$ alkyl,
(e) —CN,
(f) —$NR^A R^B$,
(g) —NH(C=O)—$C_{1-6}$ alkyl,
wherein $R^A$ and $R^B$ are selected from the group consisting of
(i) hydrogen, or
(ii) —$C_{1-6}$ alkyl,
or $R^A$ and $R^B$ are linked together with the nitrogen to which they are both attached to form a 2-6 membered carbocyclic ring, wherein one or two of the ring carbon atoms is replaced by a nitrogen, oxygen or sulfur;
$R^3$ is optionally present at one or more of the fused phenyl ring carbons, and each $R^3$ is selected from the group consisting of
(1) —$C_{1-6}$ alkyl,
(2) halogen,
(3) cyano, and
(4) —O—$C_{1-6}$ alkyl,
wherein any alkyl $R^3$ moiety is optionally substituted with one or more halo.

2. A compound of claim 1, or a pharmaceutically acceptable salt thereof, wherein $R^1$ is phenyl which is optionally substituted by one or more
(a) halogen,
(b) hydroxy,
(c) —O—$C_{1-6}$ alkyl,
(d) —$C_{1-6}$ alkyl, and
(e) cyano.

3. A compound of claim 1, or a pharmaceutically acceptable salt thereof, wherein $R^1$ is heteroaryl, which is optionally substituted by one or more
(a) halogen (for example fluoro, chloro or bromo),
(b) hydroxy,
(c) —O—$C_{1-6}$ alkyl,
(d) —$C_{1-6}$ alkyl, and
(e) cyano.

4. A compound of claim 1, or a pharmaceutically acceptable salt thereof, wherein $R^1$ is heterocyclic, which is optionally substituted by one or more
(a) hydroxy, or
(b) —$C_{1-6}$ alkyl.

5. A compound of claim 1, or a pharmaceutically acceptable salt thereof, wherein $R^1$ is cycloalkyl, alkyl or alkenyl, each of which are optionally substituted by one or more
(a) hydroxy, or
(b) halogen.

6. A compound of claim 1, or a pharmaceutically acceptable salt thereof, wherein $R^2$ is phenyl, which is optionally substituted with one or more (a) halogen,
(b) hydroxy,
(c) —O—C$_{1-6}$ alkyl,
(d) —C$_{1-6}$ alkyl,
(e) —CN,
(f) —NR$^A$R$^B$,
(g) —NH(C=O)—C$_{1-6}$ alkyl,
wherein R$^A$ and R$^B$ are selected from the group consisting of
(i) hydrogen, or
(ii) —C$_{1-6}$ alkyl,
or R$^A$ and R$^B$ are linked together with the nitrogen to which they are both attached to form a 2-6 membered carbocyclic ring, wherein one or two of the ring carbon atoms is replaced by a nitrogen, oxygen or sulfur.

7. A compound of claim 1, or a pharmaceutically acceptable salt thereof, wherein R$^2$ is heteroaryl, which is optionally substituted with one or more
(a) halogen,
(b) hydroxy,
(c) —O—C$_{1-6}$ alkyl,
(d) —C$_{1-6}$ alkyl,
(e) —CN,
(f) —NR$^A$R$^B$,
(g) —NH(C=O)—C$_{1-6}$ alkyl,
wherein R$^A$ and R$^B$ are selected from the group consisting of
(i) hydrogen, or
(ii) —C$_{1-6}$ alkyl,
or R$^A$ and R$^B$ are linked together with the nitrogen to which they are both attached to form a 2-6 membered carbocyclic ring, wherein one or two of the ring carbon atoms is replaced by a nitrogen, oxygen or sulfur.

8. A compound of claim 1, which is selected from the group consisting of
2-(2-Methylphenyl)-5-{[6-(1H-pyrazol-1-yl)pyridine-3-yl]methyl}-2,5-dihydro-3H-pyrazolo[4,3-c]cinnolin-3-one;
2-(2-Methylphenyl)-5-{[6-(1-methyl-1H-pyrazol-4-yl)pyridine-3-yl]methyl}-2,5-dihydro-3H-pyrazolo[4,3-c]cinnolin-3-one;
(±)-6-Chloro-2-(trans-2-hydroxycyclohexyl)-5[(6'-methyl-2,3'-bipyridin-5-yl)methyl]-2,5-dihydro-3H-pyrazolo[4,3-c]cinnolin-3-one;
(±)-6-Chloro-2-(trans-2-hydroxycyclohexyl)-5[(6-methylpyridin-3-yl)methyl]-2,5-dihydro-3H-pyrazolo[4,3-c]cinnolin-3-one;
2-(2-Methylphenyl)-5-{[6-(morpholin-4-yl)pyridine-3-yl]methyl}-2,5-dihydro-3H-pyrazolo[4,3-c]cinnolin-3-one;
2-(2-Methylphenyl)-5-{[6-(1,3-thiazol-4-yl)pyridin-3-yl]methyl}-2,5-dihydro-3H-pyrazolo[4,3-c]cinnolin-3-one;
2-(2,3-Dimethylphenyl)-5-{[6-(1,3-thiazol-4-yl)pyridin-3-yl]methyl}-2,5-dihydro-3H-pyrazolo[4,3-c]cinnolin-3-one;
2-(6-Fluoro-2-methylpyridin-3-yl)-5-{[6-(1-methyl-1H-pyrazol-4-yl)pyridin-3-yl]methyl}-2,5-dihydro-3H-pyrazolo[4,3-c]cinnolin-3-one;
(±)-2-(trans-2-Hydroxycyclohexyl)-5-{[6-(1,3-thiazol-4-yl)pyridin-3-yl]methyl}-2,5-dihydro-3H-pyrazolo[4,3-c]cinnolin-3-one;
2-(2-Methylphenyl)-5-[4-(6-methylpyridin-3-yl)benzyl]-2,5-dihydro-3H-pyrazolo[4,3-c]cinnolin-3-one;
2-(2,3-Dimethylphenyl)-5-[(6'-methyl-2,3'-bipyridin-5-yl)methyl]-2,5-dihydro-3H-pyrazolo[4,3-c]cinnolin-3-one;
2-(2,3-Dimethylphenyl)-5-[(6'-methyl-2,3'-bipyridin-5-yl)methyl]-2,5-dihydro-3H-pyrazolo[4,3-c]cinnolin-3-one;
or a pharmaceutically acceptable salt thereof.

9. The compound of claim 1, wherein the compound of formula (I) is a compound of formula (III):

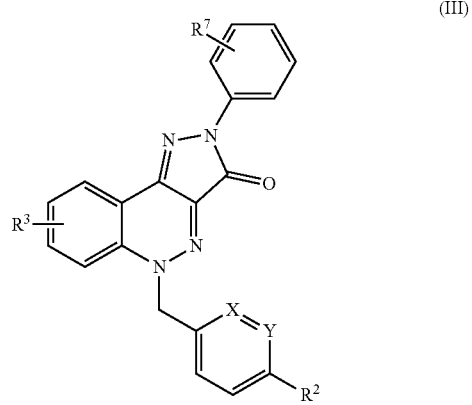

(III)

or a pharmaceutically acceptable salt thereof.

10. A compound of claim 9, or a pharmaceutically acceptable salt thereof, wherein the compound of formula (III) is a compound of formula (IIIA)

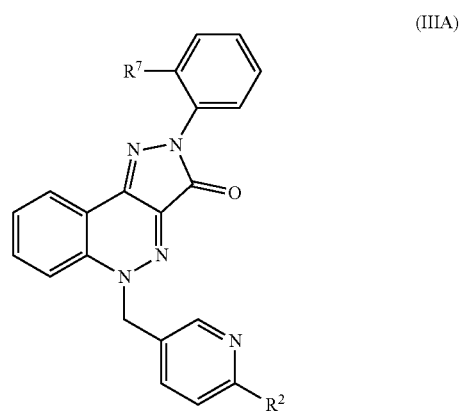

(IIIA)

wherein R$^7$ is methyl and R$^2$ is selected from the group consisting of

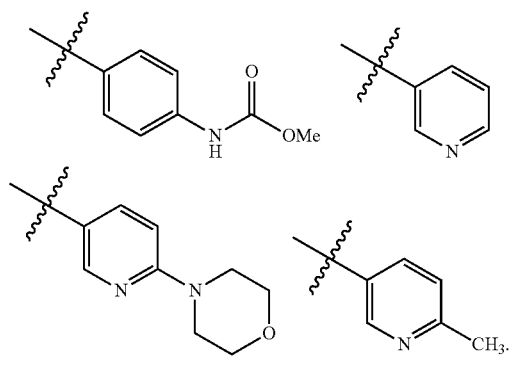

11. A compound of claim 9, or a pharmaceutically acceptable salt thereof, wherein the compound of formula (III) is a compound of formula (IIIB)

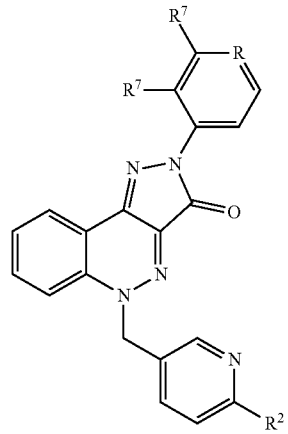
(IIIB)

and each $R^7$ is methyl, and $R^2$ is selected from the group consisting of

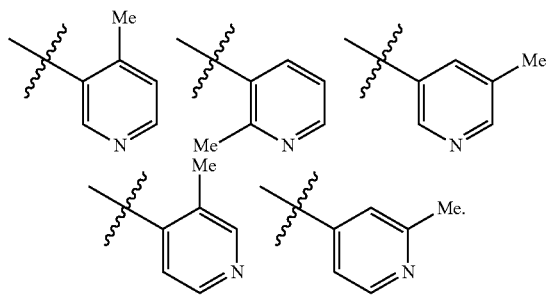

12. A compound of claim 1, or a pharmaceutically acceptable salt thereof, wherein the compound of formula (I) is a compound of formula (IV):

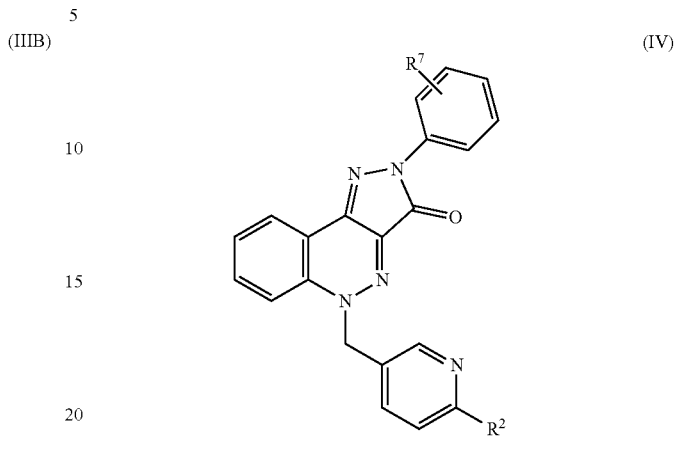
(IV)

wherein $R^7$ is optionally present at one or more of the phenyl ring carbon atoms, and each $R^7$ is selected from the group consisting of (1) halogen, (2) hydroxy, (3) —O—$C_{1-6}$ alkyl, (4) —$C_{1-6}$ alkyl, and (5) cyano.

13. A pharmaceutical composition comprising a therapeutically effective amount of a compound of any of claims 1, or a pharmaceutically acceptable salt thereof, and a pharmaceutically acceptable carrier.

\* \* \* \* \*